United States Patent
Shu et al.

(10) Patent No.: US 9,279,769 B2
(45) Date of Patent: Mar. 8, 2016

(54) PROTEINS THAT EFFICIENTLY GENERATE SINGLET OXYGEN

(75) Inventors: Xiaokun Shu, San Diego, CA (US); Roger Y. Tsien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 33 days.

(21) Appl. No.: 13/992,540

(22) PCT Filed: Dec. 7, 2011

(86) PCT No.: PCT/US2011/063841
§ 371 (c)(1),
(2), (4) Date: Aug. 20, 2013

(87) PCT Pub. No.: WO2012/078816
PCT Pub. Date: Jun. 14, 2012

(65) Prior Publication Data
US 2013/0330718 A1    Dec. 12, 2013

Related U.S. Application Data

(60) Provisional application No. 61/420,719, filed on Dec. 7, 2010.

(51) Int. Cl.
*C07K 14/00* (2006.01)
*G01N 21/64* (2006.01)
*C12N 9/12* (2006.01)

(52) U.S. Cl.
CPC .......... *G01N 21/6486* (2013.01); *C07K 14/001* (2013.01); *C12N 9/12* (2013.01); *C12Y 207/11001* (2013.01); *C07K 2319/00* (2013.01)

(58) Field of Classification Search
CPC ............ C07K 14/001; C07K 2319/00; C12Y 207/11001; G01N 21/6486
See application file for complete search history.

(56) References Cited

U.S. PATENT DOCUMENTS 5,776,689 A      7/1998  Karin et al.
2010/0304435 A1 * 12/2010 Eggert et al. ................ 435/69.1

OTHER PUBLICATIONS

Livingstone et al., CABIOS, vol. 9(6):745-756 (1993).*
Shu et al., PLoS Biol, 9(4):e1001041:1-10 (Apr. 5, 2011).*
Rost, Protein Engineering, vol. 12(2):85-89 (1999).*
Kasahara et al., The J. of Biol. Chem., vol. 285(45): 34765-34772 (Sep. 8, 2010).*
Bulina, M.E. et al., "A genetically encoded photosensitizer," *Nature Biotechnology*, Jan. 1, 2006, vol. 24, No. 1, pp. 95-99.
Buss, J.E. et al., The Six Amino-Terminal Amino Acids of $p60^{src}$ are Sufficient to Cause Myristylation of $p21^{v-ras}$ *Mol. Cell. Biol.*, 1988, vol. 8, pp. 3960-3963.

(Continued)

*Primary Examiner* — James H Alstrum Acevedo
*Assistant Examiner* — Randall L Beane
(74) *Attorney, Agent, or Firm* — Morgan, Lewis & Bockius LLP

(57) ABSTRACT

The present invention provides miniSOG proteins, polynucleotides, and methods of use. When expressed in a bacterial or mammalian cell, miniSOG proteins spontaneously incorporate flavin mononucleotide and produce fluorescence and singlet oxygen upon excitation. Uses include optical and electron microscope imaging, in vivo imaging, detection and localization of protein-protein interactions, and photoablation.

14 Claims, 18 Drawing Sheets

```
AtPhot2LOV2   IEKNFVITDPRLPDNPIIFASDSFLELTEYSREEILGRNCRFLQGPETDQATVQKIRDAI  60
miniSOG       MEKSFVITDPRLPDNPIIFASDGFLELTEYSREEILGRNCRFLQGPETDQATVQKIRDAI  60
              :**.***:********************.***************** ********************

AtPhot2LOV2   RDQREITVQLINYTKSGKKFWNLFHLQPMRDQKGELQYFIGVQLDG  106
miniSOG       RDQREITVQLINYTKSGKKFWNLLHLQPMRDQKGELQYFIGVQLDG  106
              ***********************:**********************
```

(56) References Cited

OTHER PUBLICATIONS

Chapman, S. et al., "The photoreversible fluorescent protein iLOV outperforms GFP as a reporter of plant virus infection," Dec. 16, *PNAS*, 2008, vol. 105, No. 50, pp. 20038-20043.

Crosson, S. et al., "Structure of a falvin-binding plant photoreceptor domain: Insights into light-mediated signal transduction," *PNAS*, Mar. 13, 2001, vol. 98, No. 6, pp. 2995-3000.

Crosson, S. et al., The LOV Domain Family: Photoresponsive Signaling Modules Coupled to Diverse Output Domains, *Biochemistry*, 2003, vol. 42, pp. 2-10.

Drepper, T. et al., "Reporter proteins for in vivo fluorescence without oxygen," *Nature Biotechnology*, Apr. 2007, vol. 25, No. 4, pp. 443-445.

Gaietta, G. et al., "Multicolor and Electron Microscopic Imaging of Connexin Trafficking," *Science*, Apr. 19, 2002, vol. 296, pp. 503-507.

Hancock, J.F. et al., "A CAAX or a CAAL motif an a second signal are sufficient for plasma membrane targeting of ras proteins," *The EMBO Journal*, 1991, vol. 10, No. 13, pp. 4033-4039.

Krauss, U. et al., "LOVely enzymes—towards engineering light-controllable biocatalysts," *Microbial Biotechnology*, 2010, vol. 3, No. 1, pp. 15-23.

Lostao, A. et al., "Dissecting the Energetics of the Apoflavodoxin-FMN Complex," *Journal of Biological Chemistry*, Mar. 31, 2000, vol. 275, No. 13, pp. 9518-9526.

Martin, B.R. et al., "Mammalian cell-based optimization of the biarsenical-binding tetracysteine motif for improved fluorescence and affinity," *Nature Biotechnology*, Oct. 2005, vol. 23, No. 10, pp. 1308-1314.

Möglich, A. et al., "Structural Basis for Light-dependent Signaling in the Dimeric LOV Domain of the Photosensor YtvA," *J. Mol. Biol.*, 2007, vol. 373, pp. 112-126.

Nakasako, M. et al., "Structural Basis of the LOV1 Dimerization of *Arabidopsis* Phototropins 1 and 2," *J. Mol. Biol.*, 2008, vol. 381, pp. 718-733.

Nash, A.I. et al., "Structural basis of photosensitivity in a bacterial light-oxygen-voltage/helix-turn-helix (LOV-HTH) DNA-binding protein," *PNAS*, Jun. 7, 2011, vol. 108, No. 23, pp. 9449-9454.

Powers, H.J., "Riboflavin (vitamin B-2) and health," *Am J Clin Nutr*, 2003, vol. 77, pp. 1352-1360.

Shu, X. et al., "Mammalian Expression of Infrared Fluorescent Proteins Engineered from a Bacterial Phytochrome," *Science*, May 8, 2009, vol. 324, pp. 804-807.

Vaidya, A.T. et al., "Structure of a Light-Activated LOV Protein Dimer That Regulates Transcription," *Sci. Signal*, Aug. 2, 2011, vol. 4, No. 184, pp. 1-7.

Zoltowski, B.D. et al., "Mechanism based tuning of a LOV domain photoreceptor," *Nature Chemical Biology*, Nov. 2009, vol. 5, No. 11, pp. 827-834.

Zoltowski, B.D. et al., "Conformational Switching in the Fungal Light Sensor Vivid," *Science*, May 18, 2007, vol. 316, pp. 1054-1057.

\* cited by examiner

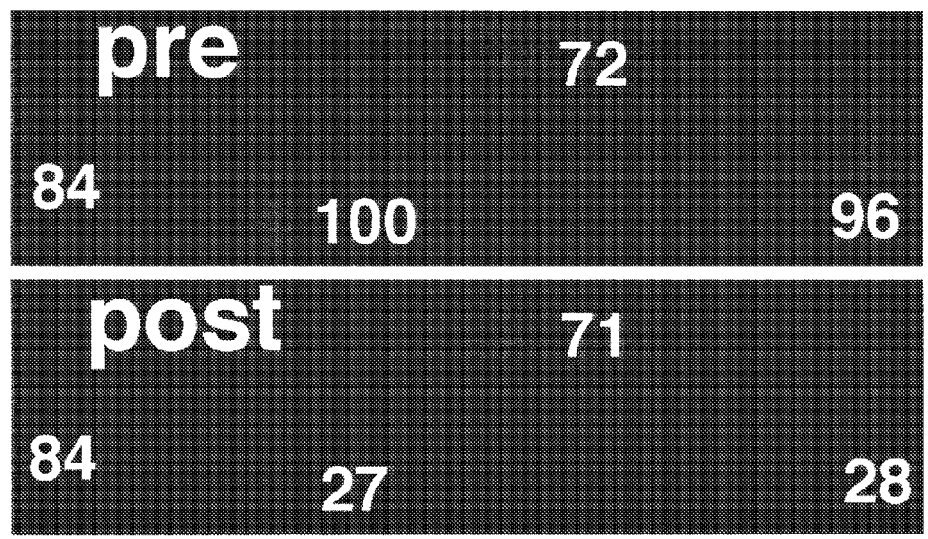
FIG. 1A
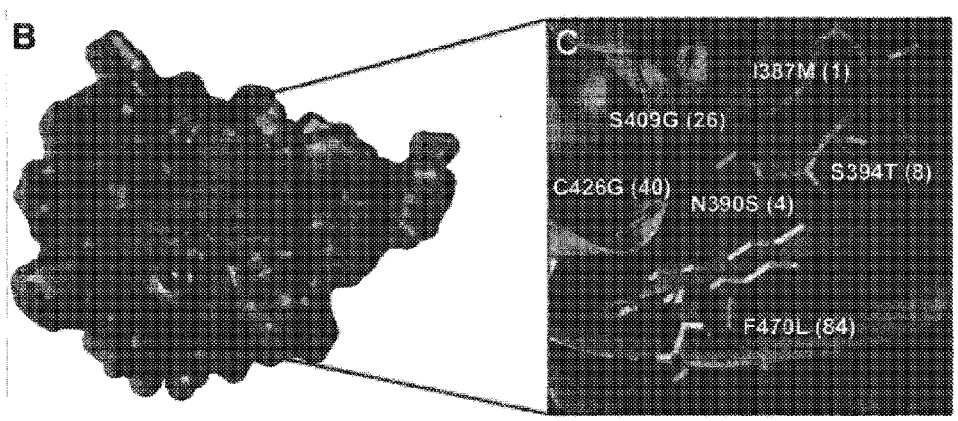
Fig. 1B
FIG. 1C

```
AtPhot2LOV2  IEKNFVITDPRLPDNPIIFASDSFLELTEYSREEILGRNCRFLQGPETDQATVQKIRDAI  60
minisOG      MEKSFVIIDPRLPDNPIIFASDGFLELTEYSREEILGRNGRFLQGPETDQATVQKIRDAI  60
              *:. ****:***************.***********:* *********************

AtPhot2LOV2  RDQREITVQLINYTKSGKKFWNLLHLQPMRDQKGELQYFIGVQLDG  106
minisOG      RDQREITVQLINYTKSGKKFWNLLHLQPMRDQKGELQYFIGVQLDG  106
             **********************************************
```

*Fig. 2*

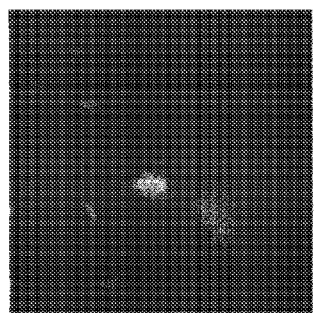 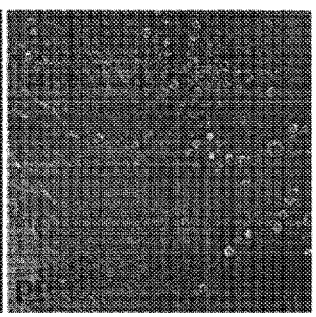 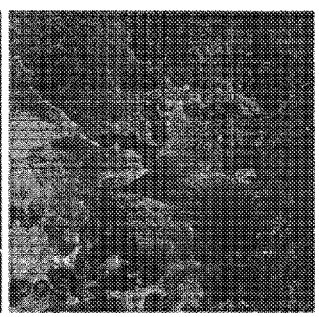
*FIG. 4A*  *FIG. 4B*  *FIG. 4C*
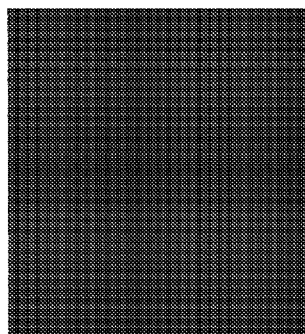 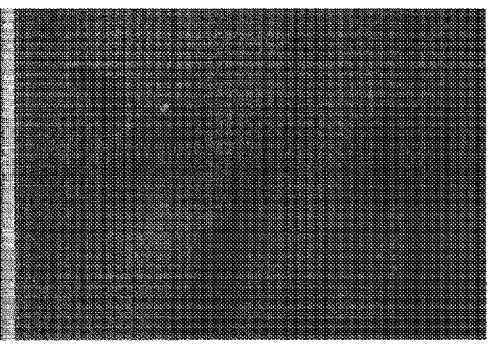
*FIG. 4D*  *FIG. 4E*

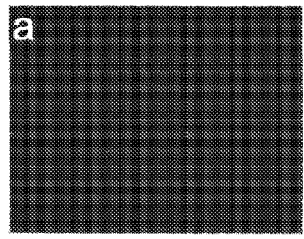
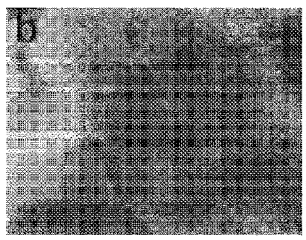
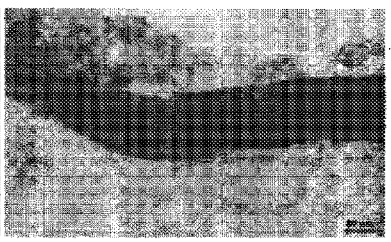
FIG. 12A
FIG. 12B
FIG. 12C
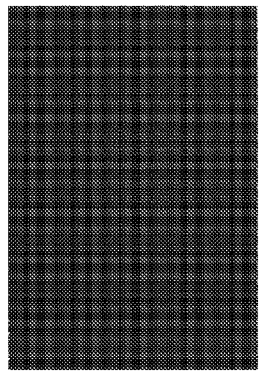
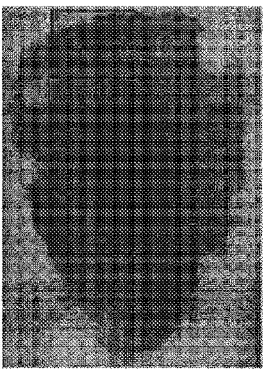
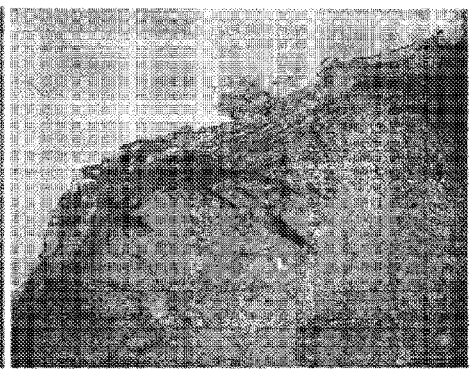
FIG. 12D
FIG. 12E
FIG. 12F
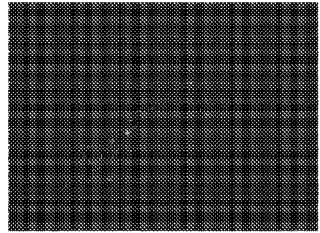
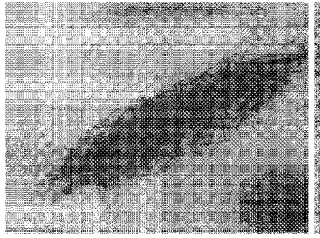
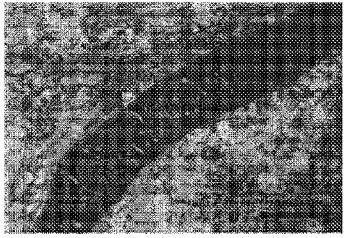
FIG. 12G
FIG. 12H
FIG. 12I

FIG. 15

PROTEINS THAT EFFICIENTLY GENERATE SINGLET OXYGEN

The present application claims the benefit of U.S. Provisional Application No. 61/420,719, filed Dec. 7, 2010, which is expressly incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with U.S. Government support under GM072033 and NS027177 awarded by the National Institutes of Health. The U.S. Government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The most general techniques for imaging specific proteins within cells and organisms rely either on antibodies or genetic tags. Electron microscopy (EM) is the standard technique for ultrastructural localization, but conventional EM immunolabeling remains challenging because of the need to develop high-affinity, high-selectivity antibodies that recognize cross-linked antigens. Furthermore, the optimal preservation of ultrastructure and visibility of cellular landmarks in EM requires strong fixation that hinders diffusibility of antibodies and gold particles. Thus the target proteins most easily labeled are those exposed at cut tissue surfaces. Replacement of bulky gold particles by eosin enables catalytic amplification via photooxidation of diaminobenzidine (DAB), but eosin-conjugated macromolecules still have limited diffusibility and need detergent permeabilization to enter cells [1]. Genetic labeling methods should overcome many of these shortcomings, just as fluorescent proteins have revolutionized light microscopic imaging in molecular and cell biology [2]. However, no analogous genetically encoded tag for EM contrast has yet proven widely applicable.

Metallothionein has been proposed as a genetic tag that can noncatalytically incorporate cadmium or gold [3], but its main applications to intact cells have been to *Escherichia coli* conditioned to tolerate 0.2 mM $CdCl_2$ for 18 h [4] or 10 mM AuCl for 3 h [4], [5]. Such high concentrations of heavy metal salts would not seem readily transferable to most multicellular organisms or their cells. Also many higher organisms express endogenous metallothionein, which would contribute background signals unless genetically deleted or knocked down [5].

Horseradish peroxidase can be a genetic label in the secretory pathway but is greatly limited by its requirements for tetramerization, glycosylation, and high $Ca^{2+}$, so that it is not functional when expressed in the cytosol [6]. Furthermore, its DAB reaction product tends to diffuse from sites of enzymatic generation, resulting in poorer resolution than immunogold or the reaction product of photogenerated singlet oxygen ($^1O_2$, the metastable excited state of $O_2$) with DAB [1], [7], [8].

Controlled local photogeneration of singlet oxygen ($^1O_2$, the metastable excited state of $O_2$) is useful for generating electron-microscopic contrast, rapidly inactivating proteins of interest, reporting protein proximities over tens of nanometers, and ablating cells by photodynamic damage. The best previous genetically targetable generator of $^1O_2$ is the biarsenical dye ReAsH, which binds to genetically appended or inserted tetracysteine motifs [9]. However, ReAsH has modest $^1O_2$ quantum yield (0.024), requires antidotes to prevent cell toxicity, needs careful precautions to reduce non-specific background signal, and has been difficult to apply to multicellular tissues and organisms [10].

Although fluorescence photooxidation using GFP has been reported [11], [12], the $^1O_2$ quantum yield of the naked GFP chromophore is extremely low (0.004), and the $^1O_2$ quantum yield of the intact protein was yet lower and unquantifiable [13], presumably because the beta-barrel of the protein shields the chromophore from oxygen. The phototoxic fluorescent protein "Killer Red" [14] is now acknowledged not to work through $^1O_2$ [15], and we have confirmed that its $^1O_2$ quantum yield is negligible.

As such, a need exists for reagents and methods that can be used to image the ultrastructural localization of proteins in cells and tissues. Specifically, there exists a need for a genetically encoded tag that can be used to enhance the EM contrast of a specific protein in a fixed tissue sample without requiring the diffusion of a large molecule, such as an antibody or gold particle, into the tissue.

BRIEF SUMMARY OF THE INVENTION

Accordingly, the present invention provides genetically encoded tags that can be used to label proteins for ultrastructural imaging via electron microscopy. The protein tags provided herein, referred to as "miniSOGs" (for mini Singlet Oxygen Generators), consist of a light, oxygen, and voltage domain of phototropin engineered to efficiently generate singlet oxygen when illuminated by blue light. Among other aspects, the present invention also provides fusion proteins comprising a miniSOG, polynucleotides encoding miniSOGs and fusion proteins thereof, and methods for imaging miniSOGs and fusion proteins thereof by light and electron microscopy.

Electron microscopy (EM) once revolutionized cell biology by revealing subcellular anatomy at resolutions of tens of nanometers, well below the diffraction limit of light microscopy. Over the past two decades, light microscopy has been revitalized by the development of spontaneously fluorescent proteins, which allow nearly any protein of interest to be specifically tagged by genetic fusion. EM has lacked comparable genetic tags that are generally applicable. Here, we introduce "miniSOG", a small (~106-residue) fluorescent flavoprotein that efficiently generates singlet oxygen when illuminated by blue light. In fixed tissue, photogenerated singlet oxygen locally polymerizes diaminobenzidine into a precipitate that is stainable with osmium and therefore can be readily imaged at high resolution by EM. Thus miniSOG is a versatile label for correlated light and electron microscopy of genetically tagged proteins in cells, tissues, and organisms including intact nematodes and mice.

We now report that *Arabidopsis* phototropin2, a blue light photoreceptor containing flavin mononucleotide (FMN) as its chromophore, can be engineered into a small (106-residue) SOG ("AtminiSOG," also referred to herein as AtminiSOG0.2; referred to as "miniSOG" in Shu X. et al., PLoS Biol. 2011 April; 9(4), the contents of which are hereby expressly incorporated by reference in their entirety for all purposes), which absorbs maximally at 448 and 473 nm with extinction coefficients of 16,700 and 13,600 $M^{-1}cm^{-1}$, respectively. Quantum yields for fluorescence and $^1O_2$ generation are 0.30 and 0.47, respectively. AtminiSOG binds endogenous FMN very tightly (dissociation constant ~$10^{-10}$ M), so bacteria and mammalian cells upregulate their total FMN to keep AtminiSOG saturated, without any obvious toxicity in the absence of illumination. Although the green fluorescence of AtminiSOG is weak and bleachable, it shows that fusions of AtminiSOG to a variety of proteins in mammalian cells appear to localize correctly, even inside organelles when appropriate. After fixation, illumination of miniSOG to generate $^1O_2$ efficiently polymerizes diaminobenzidine into an osmiophilic deposit, enabling correlative electron microscopy. Uses include detection and localization of protein-protein interactions using fluorescence or electron microscopy, use as a fusion protein, inactivation of proteins in close proximity to the miniSOG, and uses in proteomics. In a biological application, electron microscopy shows that a cell-adhesion molecule, SynCAM1, fused to miniSOG, predominantly localizes to the presynaptic side of cortical neuron synapses. This compact SOG relying only on ubiquitous endogenous FMN will greatly expand the utility of imaging and ablation techniques based on $^1O_2$.

In one aspect, the present invention provides an isolated polynucleotide encoding a miniSOG polypeptide comprising a LOV domain, wherein the LOV domain comprises a mutation at the conserved cysteine corresponding to C426 of SEQ ID NO:8.

In one embodiment of the polynucleotides described above, the LOV domain further comprises a mutation selected from the group consisting of those corresponding to I387M, N390S, S394T, S409G, and F470L of SEQ ID NO:8.

In one embodiment of the polynucleotides described above, the LOV domain is derived from a phototropin protein.

In one embodiment of the polynucleotides described above, the LOV domain comprises at least 85% identity over 100 consecutive amino acids of a sequence selected from the group consisting of SEQ ID NO:9-31.

In one embodiment of the polynucleotides described above, the LOV domain comprises at least 90% identity over 100 consecutive amino acids of a sequence selected from the group consisting of SEQ ID NO:9-31.

In one embodiment of the polynucleotides described above, the LOV domain comprises at least 95% identity over 100 consecutive amino acids of a sequence selected from the group consisting of SEQ ID NO:9-31.

In one aspect, the present invention provides an isolated polynucleotide encoding a miniSOG polypeptide comprising a LOV domain having at least 85% identity to an amino acid sequence selected from the group consisting of SEQ ID NO:1 and SEQ ID NO:2, wherein the LOV domain comprises a mutation at the conserved cysteine corresponding to C426 of SEQ ID NO:8.

In one embodiment of the polynucleotides described above, the LOV domain comprises at least 90% identity to an amino acid sequence selected from the group consisting of SEQ ID NO:1 and SEQ ID NO:2.

In one embodiment of the polynucleotides described above, the LOV domain comprises at least 95% identity to an amino acid sequence selected from the group consisting of SEQ ID NO:1 and SEQ ID NO:2.

In one embodiment of the polynucleotides described above, the miniSOG comprises an amino acid sequence selected from the group consisting of SEQ ID NO:1 and SEQ ID NO:2.

In one embodiment of the polynucleotides described above, the miniSOG polypeptide consists of from 90 to 150 amino acids.

In one embodiment of the polynucleotides described above, the miniSOG polypeptide consists of from 90 to 125 amino acids.

In one embodiment of the polynucleotides described above, the miniSOG polypeptide consists of from 90 to 110 amino acids.

In one embodiment of the polynucleotides described above, the miniSOG polypeptide consists of from 100 to 110 amino acids.

In one embodiment of the polynucleotides described above, the miniSOG polypeptide consists of 106 amino acids.

In one embodiment of the polynucleotides described above, the miniSOG polypeptide binds flavin mononucleotide with a dissociation constant of $10^{-7}$ M or less.

In one embodiment of the polynucleotides described above, the miniSOG polypeptide binds flavin mononucleotide with a dissociation constant of $10^{-8}$ M or less.

In one embodiment of the polynucleotides described above, the miniSOG polypeptide binds flavin mononucleotide with a dissociation constant of $10^{-9}$ M or less.

In one embodiment of the polynucleotides described above, the miniSOG polypeptide binds flavin mononucleotide with a dissociation constant of $10^{-10}$ M or less.

In one embodiment of the polynucleotides described above, the miniSOG polypeptide has a singlet oxygen quantum yield of 0.1 or more when bound to a flavin mononucleotide.

In one embodiment of the polynucleotides described above, the miniSOG polypeptide has a singlet oxygen quantum yield of 0.2 or more when bound to a flavin mononucleotide.

In one embodiment of the polynucleotides described above, the miniSOG polypeptide has a singlet oxygen quantum yield of 0.3 or more when bound to a flavin mononucleotide.

In one embodiment of the polynucleotides described above, the miniSOG polypeptide has a singlet oxygen quantum yield of 0.4 or more when bound to a flavin mononucleotide.

In one embodiment of the polynucleotides described above, the polynucleotide encoding the miniSOG polypeptide is codon optimized for expression in E. coli or a eukaryotic cell.

In one embodiment of the polynucleotides described above, the eukaryotic cell is a mammalian cell.

In one embodiment of the polynucleotides described above, the mammalian cell is a human cell.

In one embodiment of the polynucleotides described above, the polynucleotide comprises a nucleotide sequence selected from the group consisting of SEQ ID NOS:3-6.

In one aspect, the present invention provides a vector comprising the polynucleotide sequence of any of the polynucleotides described above.

In one aspect, the present invention provides a host cell comprising the vector of described above.

In one aspect, the present invention provides a miniSOG polypeptide encoded by any of the polynucleotides described above.

In one aspect, the present invention provides a kit comprising any of the polynucleotides described above.

In one aspect, the present invention provides a fusion protein comprising a polypeptide encoded by any of the polynucleotides described above.

In one aspect, the present invention provides a method of in vivo imaging, the method comprising the step of: expressing in a cell a fusion protein comprising a LOV domain polypeptide and a protein of interest, wherein the LOV domain polypeptide comprises a mutation at the conserved cysteine corresponding to C426 of SEQ ID NO:8.

In one embodiment of the methods described above, the cell is a bacterial or mammalian cell.

In one embodiment of the methods described above, the mammalian cell is a human cell.

In one embodiment of the methods described above, the imaging is by electron microscopy.

In one embodiment of the methods described above, the imaging is optical.

In one embodiment of the methods described above, the LOV domain polypeptide is a polypeptide of claim 30.

In one aspect, the present invention provides a method of generating singlet oxygen in a cell, the method comprising the steps of: (a) expressing in a cell a first protein comprising a LOV domain polypeptide and a protein of interest, wherein the LOV domain polypeptide comprises a mutation at the conserved cysteine corresponding to C426 of SEQ ID NO:8; and (b) irradiating the cell with blue light.

In one embodiment of the methods described above, the cell is a bacterial or mammalian cell.

In one embodiment of the methods described above, the mammalian cell is a human cell.

In one embodiment of the methods described above, the first protein is a fusion protein.

In one embodiment of the methods described above, the singlet oxygen is used to determine protein-protein proximity or protein-protein interaction.

In one embodiment of the methods described above, protein-protein proximity is detected using electron microscopy.

In one embodiment of the methods described above, protein-protein proximity is detected using optical microscopy.

In one embodiment of the methods described above, the singlet oxygen is used to cause controlled photoablation of a protein or host cell.

In one aspect, the present invention provides a method of monitoring photodynamic therapy in a subject, the method comprising the steps of administering to the subject a polynucleotide of any of claims 1 to 28 and detecting fluorescence of the singlet oxygen sensor protein encoded thereby.

BRIEF DESCRIPTION OF THE DRAWINGS

FIG. 1. (A) Infrared fluorescence of *E. coli* colonies expressing the fusion proteins before and after irradiation (480±15 nm excitation). Four colonies (pre- and post-irradiation at 480/30 nm, imaged with excitation at 685/40 nm and emission at 740/30 nm), cropped from an entire image of an agar plate with several hundred colonies covering the entire library size (=20). (B) Predicted structure of AtminiSOG by the Swiss-Model structure homology-modeling server [52]. (C) Mutations introduced into AtminiSOG0.2 compared to its parent. Numbers in bracket are based on the AtminiSOG amino acid sequence.

FIG. 2. Sequence alignment of miniSOG0.2 (miniSOG; SEQ ID NO:2) with its parent, the LOV2 domain of AtPhot2 (ATPhot2LOV2; SEQ ID NO:7). Mutations are highlighted.

FIG. 4. MiniSOG-mediated photoconversion of DAB as visualized by light microscopy. Fluorescence (A) of mammalian cells expressing cytosolic miniSOG. Matching transmitted light images before (B) and after (C) DAB photooxidation. A histone 2B-AtminiSOG0.2 fusion protein by green AtminiSOG0.2 fluorescence (D) and transmitted light after DAB photoconversion (E). Note the correspondence between fluorescence and darkening after photooxidation.

FIG. 12. Correlated fluorescence and electron microscopic imaging of various proteins and organelles using miniSOG. Fluorescence image based on the AtminiSOG0.2 fluorescence (A), transmitted light image after DAB photoconversion (B), and high-resolution electron microscopic image (C) of a AtminiSOG0.2-tagged connexin43 protein expressed in HeLa cells. Fluorescence image based on the AtminiSOG0.2 fluorescence (D), transmitted light image after DAB photoconversion (E), and high-resolution electron microscopic image (F) of a AtminiSOG0.2-tagged α-actinin protein expressed in HeLa cells. Fluorescence image based on the AtminiSOG0.2 fluorescence (G), transmitted light image after DAB photoconversion (H), and high-resolution electron microscopic image (I) of a AtminiSOG0.2-tagged cytochrome c protein expressed in HeLa cells.

DETAILED DESCRIPTION OF THE INVENTION

I. Introduction

Electron microscopy (EM) achieves the highest spatial resolution in protein localization, but specific protein EM labeling has lacked generally applicable genetically encoded tags for in situ visualization in cells and tissues. The present invention provides a fluorescent flavoprotein engineered from *Arabidopsis* phototropin 2, referred to herein as "miniSOG" (for mini Singlet Oxygen Generator). MiniSOG contains 106 amino acids, less than half the size of Green Fluorescent Protein. Illumination of miniSOG generates sufficient singlet oxygen to locally catalyze the polymerization of diaminobenzidine into an osmiophilic reaction product resolvable by EM. MiniSOG fusions to many well-characterized proteins localize correctly in mammalian cells, intact nematodes, and rodents, enabling correlated fluorescence and EM from large volumes of tissue after strong aldehyde fixation, without the need for exogenous ligands, probes, or destructive permeabilizing detergents. MiniSOG permits high quality ultrastructural preservation and 3-dimensional protein localization via electron tomography or serial section block face scanning electron microscopy.

Figure 14A:
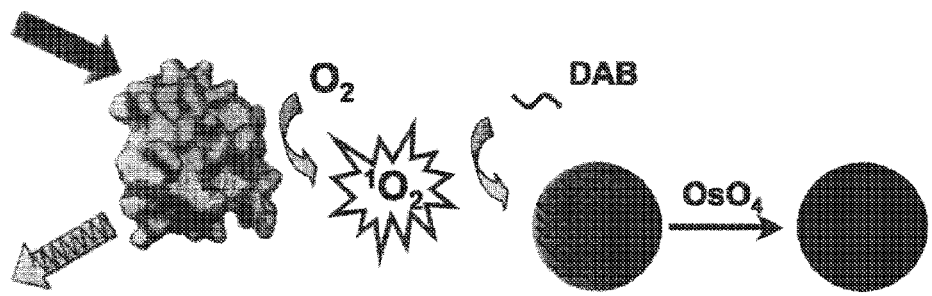
FIG. 14. (A) A cartoon showing how miniSOG generates electron-microscopic contrast. (B) Illustration of genetically targeted cell photoablation by miniSOG. (C) Images of HEK293 cells expressing mito-AtminiSOG0.2 transfected with IFP: bright-field image (upper right) fluorescent nucleus of all cells stained by Hoechst (lower left); IFP infrared fluorescence (upper-right); and fluorescence after incubation with green fluorescent dye binding to active capsases (lower-right).

Upon blue light excitation, miniSOG becomes green fluorescent and also excites molecular oxygen into singlet state (i.e. singlet oxygen). The generated singlet oxygen ($^1O_2$) oxidizes and polymerizes diaminobenzidine (DAB) into a dense, brownish precipitate, which can be stained with osmium tetroxide and then becomes visible by electron microscopy (FIG. 14A).

As a demonstration of miniSOG's capabilities, controversies about the localization of synaptic cell adhesion molecules are resolved by EM of miniSOG fusions in neuronal culture and intact mouse brain. EM shows that AtminiSOG0.2-tagged SynCAM1 is presynaptic in cultured cortical neurons, whereas AtminiSOG0.2-tagged SynCAM2 is postsynaptic in culture and in intact mice. Thus SynCAM1 and SynCAM2 could be heterophilic partners. MiniSOG may do for EM what Green Fluorescent Protein did for fluorescence microscopy.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

The term "miniSOG" protein refers to a stably-folded, non-natural protein consisting of a light, oxygen, and voltage (LOV) domain which binds to flavin mononucleotide (FMN) with high affinity and efficiently generates singlet oxygen ($^1O_2$) upon blue light excitation. Preferably, where the corresponding wild-type LOV domain contains a cysteine residue that forms a covalent cysteinyl adduct with FMN upon stimulation with blue light, the cysteine will be mutated to improve the $^1O_2$ quantum yield. MiniSOGs may contain further mutations with respect to the corresponding wild-type amino acid sequence, which may or may not improve the $^1O_2$ quantum yield. The N- and C-termini of a miniSOG protein correspond to the boundaries of the corresponding wild-type LOV domain, as described below, although the addition of up to about 10 amino acids on either or both of the termini will be well tolerated with respect to correct protein folding, FMN binding, and singlet oxygen generation upon stimulation with blue light. MiniSOG proteins generally consist of 150 amino acids or less, preferably 125 amino acids. In certain embodiments, a miniSOG protein consists of from 90 to 150 amino acids, 90 to 140 amino acids, 90 to 130 amino acids, 90 to 125 amino acids, 90 to 120 amino acids, 90 to 115 amino acids, or 90 to 110 amino acids.

The term "mutant" or "variant" is used herein in reference to a miniSOG protein that contains a mutation with respect to the sequence of its corresponding wild-type LOV domain.

The term "corresponding wild-type LOV domain" of a miniSOG is used to refer to the naturally-occurring LOV domain which was used as the starting point for the referenced miniSOG. For instance, the corresponding wild-type LOV domain of AtminiSOG0.1 refers to amino acids 387-492 of phototropin 2 from *Arabidopsis thaliana*. Thus, AtminiSOG0.1 contains I387M/C426G mutations with respect to the sequence of its corresponding wild-type LOV domain.

The term "corresponding residue" refers to an amino acid in a first LOV domain which is analogous (e.g., structurally or functionally equivalent) or homologous (e.g., evolutionarily conserved in the primary amino acid sequence) with an amino acid in a reference LOV domain. For the purposes of the present invention, the reference LOV sequence is typically residues 387 to 492 of phototropin 2 from *Arabidopsis thaliana* (i.e., the LOV2-domain of AtPhot2; SEQ ID NO:7). Accordingly, corresponding N- and C-terminal residues of a LOV domain found in a particular protein will be those which align with residues 387 and 492 of phototropin 2 from *Arabidopsis thaliana* (i.e., residues 1 and 106 of SEQ ID NO:7). Likewise, a LOV domain cysteine that forms a covalent bond with FMN is the residue corresponding to C40 of SEQ ID NO:7 or C426 of AtPhot2.

AtminiSOG0.1 and AtminiSOG0.2 are mutants of truncated phototropin 2 from *Arabidopsis thaliana*, containing amino acids 387-492, with mutations I387M/C426G and I387M/N390S/S394T/S409G/C426G/F470L, respectively. As used herein, the "AtminiSOG0.2" construct is identical to "miniSOG" construct used in Shu X. et al. (supra).

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a miniSOG protein of the invention linked to a polypeptide of interest.

The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., *EMBO J.* 10:4033-4039, 1991; Buss et al., *Mol. Cell. Biol.* 8:3960-3963, 1988; U.S. Pat. No. 5,776,689, each of which is incorporated herein by reference).

The term "operatively linked" or "operably linked" or "operatively joined" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a miniSOG protein of the present invention can be fused to a polypeptide of interest. In this case, it is preferable that the fusion molecule retains its fluorescence and ability to generate singlet oxygen, and the polypeptide of interest retains its original biological activity. In some embodiments of the present invention, the activities of either the miniSOG protein or the protein of interest can be reduced relative to their activities in isolation. Such fusions can also find use with the present invention.

As used herein, the term "singlet oxygen quantum yield" or "$^1O_2$ quantum yield" refers to the number of times a singlet oxygen is generated per photon absorbed by a fluorophore. Accordingly, the $^1O_2$ quantum yield of a miniSOG refers to the number of times a singlet oxygen is generated per photon absorbed by the FMN bound to the LOV domain. Generally, the $^1O_2$ quantum yield of a miniSOG provided herein will be at least as great as, preferably greater than, the $^1O_2$ quantum yield of the corresponding wild-type LOV domain from which the miniSOG was derived. Preferably, the maximum $^1O_2$ quantum yield of a miniSOG provided herein will be at least 0.1, preferably at least 0.2, more preferably at least 0.3, more preferably at least 0.4, most preferably at least 0.45.

The term "polypeptide" or "protein" refers to a polymer of four or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "wild-type" or "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "non-naturally occurring" is used to refer to a protein, nucleic acid molecule, cell, or other material that does not occur in nature. For example, the miniSOG proteins and fusion proteins thereof provided by the present invention are non-naturally occurring because they consist of only the LOV domain, or a variant thereof, of a protein, which is not found separate from the remainder of the naturally-occurring protein in nature.

The term "identical," when used in reference to two or more polynucleotide sequences or two or more polypeptide sequences, refers to the residues in the sequences that are the same when aligned for maximum correspondence. When percentage of sequence identity is used-in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any-well known algorithm (see, for example, Meyers and Miller, *Comp. Appl. Biol. Sci.* 4:11-17, 1988; Smith and Waterman, *Adv. Appl. Math.* 2:482, 1981; Needleman and Wunsch, *J. Mol. Biol.* 48:443, 1970; Pearson and Lipman, *Proc. Natl. Acad. Sci., USA* 85:2444 (1988); Higgins and Sharp, *Gene* 73:237-244, 1988; Higgins and Sharp, *CABIOS* 5:151-153; 1989; Corpet et al., *Nucl. Acids Res.* 16:10881-10890, 1988; Huang, et al., *Comp. Appl. Biol. Sci.* 8:155-165, 1992; Pearson et al., *Meth. Mol. Biol.*, 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid.

Conservative amino acid substitutions providing functionally similar amino acids are well known in the art. Dependent on the functionality of the particular amino acid, i.e., catalytically important, structurally important, sterically important, different groupings of amino acid may be considered conservative substitutions for each other. Table 1 provides groupings of amino acids that are considered conservative substitutions based on the charge and polarity of the amino acid, the hydrophobicity of the amino acid, the surface exposure/structural nature of the amino acid, and the secondary structure propensity of the amino acid.

TABLE 1

Groupings of conservative amino acid substitutions based on the functionality of the residue in the protein.

| Important Feature | Conservative Groupings |
|---|---|
| Charge/Polarity | 1. H, R, and K |
| | 2. D and E |
| | 3. C, T, S, G, N, Q, and Y |
| | 4. A, P, M, L, I, V, F, and W |
| Hydrophobicity | 1. D, E, N, Q, R, and K |
| | 2. C, S, T, P, G, H, and Y |
| | 3. A, M, I, L, V, F, and W |
| Structural/Surface Exposure | 1. D, E, N, Q, H, R, and K |
| | 2. C, S, T, P, A, G, W, and Y |
| | 3. M, I, L, V, and F |
| Secondary Structure Propensity | 1. A, E, Q, H, K, M, L, and R |
| | 2. C, T, I, V, F, Y, and W |
| | 3. S, G, P, D, and N |
| Evolutionary Conservation | 1. D and E |
| | 2. H, K, and R |
| | 3. N and Q |
| | 4. S and T |
| | 5. L, I, and V |
| | 6. F, Y, and W |
| | 7. A and G |
| | 8. M and C |

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity. In certain embodiments, substantially similar sequences will have at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset of codons from among the set of codons encoding an amino acid that are most frequently used in proteins expressed in mammalian cells as chosen from the following list: Gly (GGC, GGG); Glu (GAG); Asp (GAC); Val (GUG, GUC); Ala (GCC, GCU); Ser (AGC, UCC); Lys (AAG); Asn (AAC); Met (AUG); Ile (AUC); Thr (ACC); Trp (UGG); Cys (UGC); Tyr (UAU, UAC); Leu (CUG); Phe (UUC); Arg (CGC, AGG, AGA); Gln (CAG); His (CAC); and Pro (CCC).

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present invention. In general, a fluorescent protein useful for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of *Aequorea* GFP can be derived from the naturally occurring GFP by engineering mutations such as amino acid substitutions into the reference GFP protein.

Many cnidarians use green fluorescent proteins as energy transfer acceptors in bioluminescence. The term "green fluorescent protein" is used broadly herein to refer to a protein that fluoresces green light, for example, *Aequorea* GFP. GFPs have been isolated from the Pacific Northwest jellyfish, *Aequorea victoria*, the sea pansy, *Renilla reniformis*, and *Phialidium gregarium* (Ward et al., *Photochem. Photobiol.* 35:803-808, 1982; Levine et al., *Comp. Biochem. Physiol.* 72B:77-85, 1982, each of which is incorporated herein by reference). Similarly, reference is made herein to "red fluorescent proteins", which fluoresce red, "cyan fluorescent proteins," which fluoresce cyan, and the like. RFPs, for example, have been isolated from the corallimorph *Discosoma* (Matz et al., *Nature Biotechnology* 17:969-973 [1999]). The term "red fluorescent protein," or "RFP" is used in the broadest sense and specifically covers the *Discosoma* RFP (DsRed), and red fluorescent proteins from any other species, such as coral and sea anemone, as well as variants thereof as long as they retain the ability to fluoresce red light.

III. Sequences

MiniSOG0.1 Amino Acid Sequence:

(SEQ ID NO: 1)
MEKNEVISDPRLPDNPIIFASDSFLELTEYSREEILGRNGRFLQGPET

DQATVQKIRDAIRDQREITVQLINYTKSGKKFWNLFHLQPMRDQKGEL

QYFIGVQLDG.

MiniSOG (MiniSOG0.2) Amino Acid Sequence:

(SEQ ID NO: 2)
MEKSFVITDPRLPDNPIIFASDGFLELTEYSREEILGRNGRFLQGPET

DQATVQKIRDAIRDQREITVQLINYTKSGKKFWNLLHLQPMRDQKGEL

QYFIGVQLDG

Nucleic Acid Sequence Encoding MiniSOG0.1 (Codon Optimized for Expression in *E. coli*):

(SEQ ID NO: 3)
ATGGAAAAAAACTTCGTGATTTCTGACCCGCGCCTGCCGGATAATCCG

ATCATCTTCGCCTCCGATAGCTTCCTGGAACTGACTGAATACAGCCGT

GAGGAAATTCTGGGTCGTAATGGCCGTTTCCTGCAGGGCCCGGAAACC

-continued
GATCAAGCAACTGTTCAGAAAATTCGTGATGCAATCCGTGATCAACGT

GAAATCACCGTGCAGCTGATTAACTATACCAAAAGCGGCAAGAAATTC

TGGAACCTGTTTCACCTGCAGCCGATGCGCGATCAGAAAGGTGAGCTG

CAGTACTTCATCGGCGTTCAGCTGGATGGT.

Nucleic Acid Sequence Encoding MiniSOG0.1 (Codon Optimized for Expression in Human Cells):

(SEQ ID NO: 4)
ATGGAGAAAAATTTCGTGATAAGTGATCCACGGCTGCCAGACAATCCC

ATCATCTTCGCATCCGATTCCTTCCTGGAGCTGACCGAGTATTCCAGA

GAGGAGATCCTGGGCCGCAATGGCCGCTTTCTGCAGGGACCAGAGACA

GACCAGGCCACAGTGCAGAAGATTCGCGATGCCATTAGAGATCAGCGC

GAGATTACCGTGCAGCTGATAAACTACACAAAAAGCGGGAAGAAATTC

TGGAACCTCTTTCACCTCCAGCCCATGAGGGACCAGAAGGGTGAGCTC

CAGTATTTCATCGGAGTGCAGCTGGATGGA.

Nucleic Acid Sequence Encoding MiniSOG (MiniSOG0.2; Codon Optimized for Expression in *E. coli*):

(SEQ ID NO: 5)
ATGGAAAAAAGCTTCGTGATTACTGACCCGCGCCTGCCGGATAATCCG

ATCATCTTCGCCTCCGATGGCTTCCTGGAACTGACTGAATACAGCCGT

GAGGAAATTCTGGGTCGTAATGGCCGTTTCCTGCAGGGCCCGGAAACC

GATCAAGCAACTGTTCAGAAAATTCGTGATGCAATCCGTGATCAACGT

GAAATCACCGTGCAGCTGATTAACTATACCAAAAGCGGCAAGAAATTC

TGGAACCTGTTGCACCTGCAGCCGATGCGCGATCAGAAAGGTGAGCTG

CAGTACTTCATCGGGGTTCAGCTGGATGGT.

Nucleic Acid Sequence Encoding MiniSOG (miniSOG0.2; Codon Optimized for Expression in Human Cells):

(SEQ ID NO: 6)
ATGGAGAAAAGTTTCGTGATAACTGATCCACGGCTGCCAGACAATCCC

ATCATCTTCGCATCCGATGGCTTCCTGGAGCTGACCGAGTATTCCAGA

GAGGAGATCCTGGGCCGCAATGGCCGCTTTCTGCAGGGACCAGAGACA

GACCAGGCCACAGTGCAGAAGATTCGCGATGCCATTAGAGATCAGCGC

GAGATTACCGTGCAGCTGATAAACTACACAAAAAGCGGGAAGAAATTC

TGGAACCTCCTGCACCTCCAGCCCATGAGGGACCAGAAGGGTGAGCTC

CAGTATTTCATCGGAGTGCAGCTGGATGGA

*Arabidopsis Thaliana* Phototropin-2 (AtPhot2) Amino Acid Sequence:

(SEQ ID NO: 8)
MERPRAPPSPLNDAESLSERRSLEIFNPSSGKETHGSTSSSSKPPLDG

NNKGSSSKWMEFQDSAKITERTAEWGLSAVKPDSGDDGISFKLSSEVE

RSKNMSRRSSEESTSSESGAFPRVSQELKTALSTLQQTFVVSDATQPH

CPIVYASSGFFTMTGYSSKEIVGRNCRFLQGPDTDKNEVAKIRDCVKN

GKSYCGRLLNYKKDGTPFWNLLTVTPIKDDQGNTIKFIGMQVEVSKYT

EGVNDKALRPNGLSKSLIRYDARQKEKALDSITEVVQTIRHRKSQVQE

SVSNDTMVKPDSSTTPTPGRQTRQSDEASKSFRTPGRVSTPTGSKLKS

SNNRHEDLLRMEPEELMLSTEVIGQRDSWDLSDRERDIRQGIDLATTL

ERIEKNFVISDPRLPDNPIIFASDSFLELTEYSREEILGRNCRFLQGP

ETDQATVQKIRDAIRDQREITVQLINYTKSGKKFWNLFHLQPMRDQKG

ELQYFIGVQLDGSDHVEPLQNRLSERTEMQSSKLVKATATNVDEAVRE

LPDANTRPEDLWAAHSKPVYPLPHNKESTSWKAIKKIQASGETVGLHH

FKPIKPLGSGDTGSVHLVELKGTGELYAMKAMEKTMMLNRNKAHRACI

EREIISLLDHPFLPTLYASFQTSTHVCLITDFCPGGELFALLDRQPMK

HCLGIVYRDLKPENILLKKDGHIVLADFDLSFMTTCTPQLIIPAAPSK

RRRSKSQPLPTFVAEPSTQSNSFVGTEEYIAPEIITGAGHTSAIDWWA

LGILLYEMLYGRTPFRGKNRQKTFANILHKDLTFPSSIPVSLVGRQLI

NTLLNRDPSSRLGSKGGANEIKQHAFFRGINWPLIRGMSPPPLDAPLS

IIEKDPNAKDIKWEDDGVLVNSTDLDIDLF

IV. Light, Oxygen, and Voltage (LOV) Domains

Light, oxygen, and Voltage (LOV) domains function as blue light-sensing protein modules in photoreceptor proteins identified across a wide range of organisms in nature, including plants, fungi, algae, and bacteria. LOV domains bind a flavin mononucleotide (FMN), which becomes energetically excited upon absorption of blue light. In nature, the energy absorbed from photons of blue light is then used to form a covalent bond between the carbon (C4) atom of the flavin isoalloxazine ring and a conserved cysteine molecule found in the core of the LOV domain. This conformation where FMN is covalently bound to the LOV domain, which has been referred to as the "signaling state" of the system (Krauss et al., Microbial Biotechnolgy (2010) 3(1), 15-23), then decomposes over time returning the system to the "dark state," where relaxed FMN is again non-covalently bound to the LOV domain.

LOV domains belong to the Per-ARNT-Sim (PAS) domain superfamily and adopt a canonical PAS domain fold consisting of a five-stranded antiparallel β-sheet (Crosson and Moffat, PNAS U.S.A. (2001) March 13; 98(6):2995-3000). Crystollographic molecular structures have been determined for LOV domains from a diverse range of proteins and host proteins, including: *Adiantum* sp. Phy3 protein (PDB IDs: 1G28 and 1JNU; Crosson and Moffat, supra); *Neurospora crassa* Vvd protein (PDB IDs: 2PD7, 2PD8, 2PDR, and 2PDT; Zoltowski B. D. et al., Science (2007) 316:1054-1057; PDB IDs: 3HJI and 3HLK; Zoltowski B. D. et al., Nat. Chem. Biol. (2009) 5:827-834; and PDB ID NO:3RH8; Vaidya et al., Sci. Signal. (2011) 4:ra50-ra50); *Bacillus subtilis* YtvA protein (PDB IDs: 2PR5 and 2PR6; Moglich and Moffat, J. Mol. Biol. (2007) 373:112-126); *Arabidopsis thaliana* Phot1 and Phot2 proteins (PDB IDs: 2Z6C and 2Z6D; Nakasako M. et al., J. Mol. Biol. (2008) 381:718-733); and *Erythrobacter litoralis* E1222 protein (PDB ID NO:3P7N; McNulty and Luecke, PNAS U.S.A. (2011) 108:9499-9454), the disclosures of which are hereby expressly incorporated by reference in their entireties for all purposes.

Available structural and biochemical information on various LOV domains have identified conserved residues that are important for FMN binding and putative residues involved in intra- and/or inter-molecular communication. An alignment of several LOV domains is provided in FIG. 15. By using various techniques known in the art, one of skill will readily be able to generate LOV domain constructs suitable for use in the methods provided herein. Steps in the construction of a suitable LOV domain construct include, but are limited to, identification of a LOV domain in a protein, selection of suitable N- and C-termini for the construct, mutation of residues that increase the singlet oxygen quantum yield (e.g., mutation of the conserved cysteine involved in the covalent attachment to FMN upon stimulation with blue light and mutations in residues that increase access of FMN to environmental $O_2$ to increase efficient energy transfer) and/or change the fluorescent characteristics of the molecule (e.g., increase or decrease the brightness of fluorescence or tune the excitation or emission spectra of fluorescence).

Representative techniques useful in the generation of LOV domains (i.e., miniSOGs) include, but are not limited to, protein order/disorder prediction models (e.g., PONDR-FIT (Xue B. et al., Biochim Biophys Acta. 2010 April; 1804(4): 996-1010) or Disprot (Vucetic, S. et al., Structure, Function, and Genetics, 52 (4), 573-584)), generation of multiple sequence alignments (e.g., MUSCLE (Edgar R. C. Nuc. Acid. Res. (2004) 32(5):1792-97) or T-Coffee (Notredame C. et al., J Mol. Biol. (2000) September 8; 302(1):205-17)), and structural modeling (e.g., Swiss-Model structure homology-modeling server [52] or HHpred (Söding J. et al., Nucleic Acids Res. (2005) July 1; 33)).

Accordingly, the structural information available for LOV domains can be used in conjunction with the these and other techniques to design LOV domains (i.e., miniSOGs) suitable for use in the present invention. Furthermore, the structural and functional data available for LOV domains can be used to mutate residues within the resulting miniSOG constructs, while providing confidence that FMN binding and singlet oxygen ($^1O_2$) quantum yield will not be significantly perturbed. Mutation of residues not directly involved in the interaction with FMN, especially residues with solvent exposed side-chains, are generally well tolerated in LOV domains (i.e., miniSOGs) used in conjunction with the present invention.

It is preferable that miniSOGs derived from a wild-type LOV domain containing a cysteine residue that forms a cysteinyl adduct with FMN upon stimulation with blue light will contain a mutation at that cysteine residue, which does not significantly disrupt FMN binding. These cysteine-mutant miniSOG proteins will have $^1O_2$ quantum yield of a miniSOG provided herein will be greater than the $^1O_2$ quantum yield of the corresponding wild-type LOV domain.

V. MiniSOG Polypeptides

MiniSOG polypeptides are stably-folded, non-natural polypeptides consisting of a light, oxygen, and voltage (LOV) domain which binds to flavin mononucleotide (FMN) with high affinity and efficiently generates singlet oxygen ($^1O_2$) upon blue light excitation. Optionally, miniSOG proteins include a short N- and/or C-terminus peptide that enhances expression, localization, and/or secretion, i.e., an N-terminal methionine, signaling peptide, pre-pre-peptide, or residual amino acids left after the removal of a signaling or pre-propeptide.

The cofactor FMN itself is a well-known efficient singlet oxygen generator (SOG). The engineered LOV domains provided herein bind to FMN and the whole complex photo-generates singlet oxygen efficiently, whereas the corresponding wild type LOV domain with FMN does not photo-generate singlet oxygen because the absorbed light energy is consumed by formation of the covalent bond with the conserved cysteine (corresponding to Cys426 of *Arabidopsis thaliana* Phototropin 2) of the LOV domain. The key mutation, C426G in *Arabidopsis thaliana* Phototropin 2 or equivalent, is responsible in converting the wild type LOV domain from an inefficient SOG to an efficient one because it diverts the use of absorbed light energy. Other mutations may be introduces to improve the protein folding, stability, solubility, and/or fluorescence.

Generally, a miniSOG polypeptide consists of 150 or less amino acids, preferably 125 or less amino acids. In one embodiment, a miniSOG protein consists of from 90 to 150 amino acids. In another embodiment, a miniSOG polypeptide consists of from 90 to 145 amino acids. In another embodiment, a miniSOG polypeptide consists of from 90 to 140 amino acids. In another embodiment, a miniSOG polypeptide consists of from 90 to 135 amino acids. In another embodiment, a miniSOG polypeptide consists of from 90 to 130 amino acids. In another embodiment, a miniSOG polypeptide consists of from 90 to 125 amino acids. In another embodiment, a miniSOG polypeptide consists of from 90 to 120 amino acids. In another embodiment, a miniSOG polypeptide consists of from 90 to 115 amino acids. In another embodiment, a miniSOG polypeptide consists of from 90 to 110 amino acids. In another embodiment, a miniSOG polypeptide consists of 106 amino acids. In another embodiment, a miniSOG polypeptide consists of from 100 to 110 amino acids.

In yet other embodiments, a miniSOG polypeptide consists of 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 amino acids.

The N- and C-termini of a miniSOG protein correspond to the boundaries of the corresponding wild-type LOV domain, although the addition of up to about 10 amino acids on either or both of the termini will be well tolerated with respect to correct protein folding, FMN binding, and singlet oxygen generation upon stimulation with blue light. One of skill will readily be able to determine suitable boundaries for the N- and C-terminus of a miniSOG protein. In one embodiment, the N- and C-termini of a miniSOG protein corresponds to residues 387 and 492 of phototropin 2 from *Arabidopsis thaliana*, respectively.

Preferably, where the corresponding wild-type LOV domain contains a cysteine residue corresponding to C426 of AtPhot2 (C40 of SEQ ID NO:7) that forms a covalent cysteinyl adduct with FMN upon stimulation with blue light, the cysteine will be mutated to improve the $^1O_2$ quantum yield. In other embodiments, where the corresponding wild-type LOV domain does not contain a cysteine at the position corresponding to C426 of AtPhot2, the LOV domain may not need to be mutated in order to achieve efficient $^1O_2$ quantum yield.

MiniSOGs may contain further mutations with respect to the corresponding wild-type amino acid sequence, which may or may not improve the $^1O_2$ quantum yield, brightness of fluorescence, or tune the excitation or emission spectra of the miniSOG. In certain embodiments, one or more mutations are made at a residue corresponding to I387, N390, S394, S409, and F470, of AtPhot2, i.e., at a residue corresponding to I1, N4, S8, S23, C426, and F84 of SEQ ID NO:7.

Other proteins containing LOV domains suitable for use in the inventions described herein (e.g., phototropins, YtvA, LOV-histidine kinases, etc.) can be found in plants, fungi, algae, and bacteria, including, but not limited to the genera

*Arabidopsis, Populus, Phaseolus, Glycine, Spinacia, Medicago, Solanum, Vitis, Oryza, Physcomitrella, Bacillus, Brucella, Erythrobacter, Pseudomonas*, etc.

In one embodiment, the present invention provides a miniSOG protein consisting of the LOV2 domain of the AtPhot2 protein, wherein the protein comprises at least a mutation at residue C426. In one embodiment, the mutation is selected from C426G, C426A, C426S, C426T, and C426P. In a preferred embodiment, the mutation is, C426G.

As described above, the N- and C-termini of miniSOG provided herein do not need to correspond to any particular residue defined as the first or last residue of a particular LOV-domain. In one embodiment, the N-terminal residue of an AtminiSOG is amino acid 387 of the AtPhot2 protein (SEQ ID NO:8). In other embodiments, the N-terminal residue of an AtminiSOG is amino acid 377, 378, 379, 380, 381, 382, 383, 384, 385, 386, 388, 389, 390, or 391 of the AtPhot2 protein (SEQ ID NO:8). Likewise in one embodiment, the C-terminal residue of an AtminiSOG is amino acid 492 of the AtPhot2 protein (SEQ ID NO:8). In other embodiments, the N-terminal residue of an AtminiSOG is amino acid 488, 489, 490, 491, 493, 494, 495, 496, 497, 498, 499, 500, 501, or 502 of the AtPhot2 protein (SEQ ID NO:8).

In one embodiment, the present invention provides a miniSOG polypeptide comprising at least 80% identity to an amino acid sequence of SEQ ID NO:1. In another embodiment, the polypeptide comprises at least 85% sequence identity to SEQ ID NO:1. In another embodiment, the polypeptide comprises at least 90% sequence identity to SEQ ID NO:1. In another embodiment, the polypeptide comprises at least 95% sequence identity to SEQ ID NO:1. In yet another embodiment, the polypeptide has the amino acid sequence of SEQ ID NO:1. In yet other embodiments, the polypeptide comprises at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1.

In one embodiment, the present invention provides a miniSOG polypeptide comprising at least 80% identity to an amino acid sequence of SEQ ID NO:2. In another embodiment, the polypeptide comprises at least 85% sequence identity to SEQ ID NO:2. In another embodiment, the polypeptide comprises at least 90% sequence identity to SEQ ID NO:2. In another embodiment, the polypeptide comprises at least 95% sequence identity to SEQ ID NO:2. In yet another embodiment, the polypeptide has the amino acid sequence of SEQ ID NO:2. In yet other embodiments, the polypeptide comprises at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:2.

In one embodiment, the present invention provides a miniSOG polypeptide comprising at least 80% identity over at least 100 consecutive amino acids of a sequence selected from SEQ ID NOS:9 to 31, wherein the polypeptide comprises at least one mutation at residue C52. In a particular embodiment, the miniSOG polypeptide comprises amino acids 13-118 of a sequence selected from SEQ ID NOS:9 to 31. In another embodiment, the polypeptide comprises at least 85% sequence identity over at least 100 consecutive amino acids of a sequence selected from SEQ ID NOS:9 to 31. In another embodiment, the polypeptide comprises at least 90% sequence identity over at least 100 consecutive amino acids of a sequence selected from SEQ ID NOS:9 to 31. In another embodiment, the polypeptide comprises at least 95% sequence identity over at least 100 consecutive amino acids of a sequence selected from SEQ ID NOS:9 to 31. In another embodiment, the polypeptide comprises at least 98% sequence identity over at least 100 consecutive amino acids of a sequence selected from SEQ ID NOS:9 to 31. In yet other embodiments, the polypeptide comprises at least 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100 consecutive amino acids of a sequence selected from SEQ ID NOS:9 to 31. The miniSOG polypeptides having homology to SEQ ID NOS:9 to 31 bind FMN with high affinity and efficiently generate singlet oxygen upon stimulation with blue light.

In one embodiment, a miniSOG protein has at least 80% identity to at least 100-110 consecutive amino acids of a corresponding LOV domain. In another embodiment, the miniSOG protein a miniSOG protein has at least 85% identity to at least 100-110 consecutive amino acids of a corresponding LOV domain. In another embodiment, the miniSOG protein a miniSOG protein has at least 90% identity to at least 100-110 consecutive amino acids of a corresponding LOV domain. In another embodiment, the miniSOG protein a miniSOG protein has at least 95% identity to at least 100-110 consecutive amino acids of a corresponding LOV domain.

In one embodiment, the miniSOG polypeptides of the invention further comprise a mutation at one or more residues corresponding to I1, N4, S8, S23, and F84 of SEQ ID NO:7. In one embodiment, the mutation is selected from those corresponding to I1M, N4S, S8T, S23G, and F84L of SEQ ID NO:7. In a specific embodiment, the miniSOG comprises I1M/C40G mutations with respect to SEQ ID NO:7. In another specific embodiment, the miniSOG polypeptide comprises I1M/C40G mutations with respect to SEQ ID NO:7.

In one embodiment, a miniSOG protein further comprises a mutation at a residue corresponding to I387 of SEQ ID NO:8. In a specific embodiment, the miniSOG comprises a Met residue at a position corresponding to I387 of SEQ ID NO:8. In one embodiment, a miniSOG comprises a Gly residue at a position corresponding to C426 and a Met residue at a position corresponding to I387 of SEQ ID NO:8.

In one embodiment, a miniSOG protein further comprises a mutation at a residue corresponding to N390 of SEQ ID NO:8. In a specific embodiment, the miniSOG comprises a Ser residue at a position corresponding to N390 of SEQ ID NO:8. In one embodiment, a miniSOG comprises a Gly residue at a position corresponding to C426 and a Ser residue at a position corresponding to N390 of SEQ ID NO:8.

In one embodiment, a miniSOG protein further comprises a mutation at a residue corresponding to S394 of SEQ ID NO:8. In a specific embodiment, the miniSOG comprises a Thr residue at a position corresponding to N394 of SEQ ID NO:8. In one embodiment, a miniSOG comprises a Gly residue at a position corresponding to C426 and a Thr residue at a position corresponding to N394 of SEQ ID NO:8.

In one embodiment, a miniSOG protein further comprises a mutation at a residue corresponding to S409 of SEQ ID NO:8. In a specific embodiment, the miniSOG comprises a Gly residue at a position corresponding to S409 of SEQ ID NO:8. In one embodiment, a miniSOG comprises a Gly residue at a position corresponding to C426 and a Gly residue at a position corresponding to S409 of SEQ ID NO:8.

In one embodiment, a miniSOG protein further comprises a mutation at a residue corresponding to F470 of SEQ ID NO:8. In a specific embodiment, the miniSOG comprises a Leu residue at a position corresponding to F470 of SEQ ID NO:8. In one embodiment, a miniSOG comprises a Gly residue at a position corresponding to C426 and a Leu residue at a position corresponding to F470 of SEQ ID NO:8.

In one embodiment, a miniSOG comprises mutations corresponding to I387M/N390S/S394T/S409G/C426G/F470L of SEQ ID NO:8.

Figure 15:
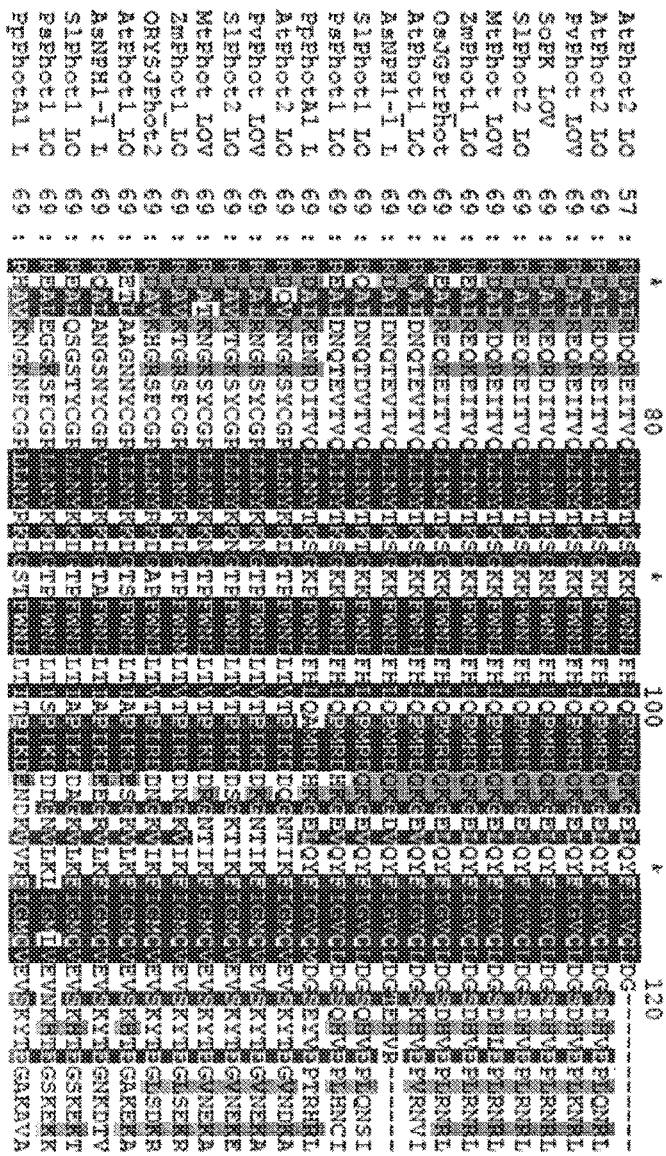
FIG. 15. Sequence alignment of LOV domains from various proteins and organisms. AtPhot2_LOV2 (387-492)=*Arabidopsis thaliana* Phototropin 2 LOV domain 2 (SEQ ID NO:7); AtPhot2_LOV2=*Arabidopsis thaliana* Phototropin 2 LOV domain 2 (SEQ ID NO:9); PvPhot_LOV2=*Phaseolus vulgaris* Phototropin LOV domain 2 (SEQ ID NO:10); SoPK_LOV=*Spinacia oleracea* Protein Kinase LOV domain (SEQ ID NO:11); SlPhot2_LOV2=*Solanum lycopersicum* Phototropin 2 LOV domain 2 (SEQ ID NO:12); MtPhot_LOV2=*Medicago truncatula* Phototropin LOV domain 2 (SEQ ID NO:13); ZmPhot1_LOV2=*Zea mays* Phototropin 1 LOV domain 2 (SEQ ID NO:14); OsJGPrPhot1_LOV2=*Oryza sativa* Japonica Group predicted Phototropin 1 LOV domain 2 (SEQ ID NO:15); AtPhot1_LOV2=*Arabidopsis thaliana* Phototropin 1 LOV domain 2 (SEQ ID NO:16); AsNPH1-1_LOV2=*Avena sativa* NPH1-1 LOV domain 2 (SEQ ID NO:17); SlPhot1_LOV2=*Solanum lycopersicum* Phototropin 1 LOV domain 2 (SEQ ID NO:18); PsPhot1_LOV2=*Pisum sativum* Phototropin 1 LOV domain 2 (SEQ ID NO:19); PpPhotA1_LOV2=*Physcomitrella patens* Phototropin A1 LOV domain 2 (SEQ ID NO:20); AtPhot2_LOV1=*Arabidopsis thaliana* Phototropin 2 LOV domain 1 (SEQ ID NO:21); PvPhot_LOV1=*Phaseolus vulgaris* Phototropin LOV domain 1 (SEQ ID NO:22); SlPhot2_LOV1=*Solanum lycopersicum* Phototropin 2 LOV domain 1 (SEQ ID NO:23); MtPhotLOV1=*Medicago truncatula* Phototropin LOV domain 1 (SEQ ID NO:24); ZmPhot1_LOV1=*Zea mays* Phototropin 1 LOV domain 1 (SEQ ID NO:25); ORYSJPhot2 LOV1=*Oryza sativa* Japonica Group Phototropin 2 LOV domain 1 (SEQ ID NO:26); AtPhot1_LOV1=*Arabidopsis thaliana* Phototropin 1 LOV domain 1 (SEQ ID NO:27); AsNPH1-1_LOV1=*Avena sativa* NPH1-1 LOV domain 1 (SEQ ID NO:28); SlPhot1_LOV1=*Solanum lycopersicum* Phototropin 1 LOV domain 1 (SEQ ID NO:29); PsPhot1_LOV1=*Pisum sativum* Phototropin 1 LOV domain 1 (SEQ ID NO:30); PpPhotA1_LOV1=*Physcomitrella patens* Phototropin A1 LOV domain 1 (SEQ ID NO:31).
Figure 16:
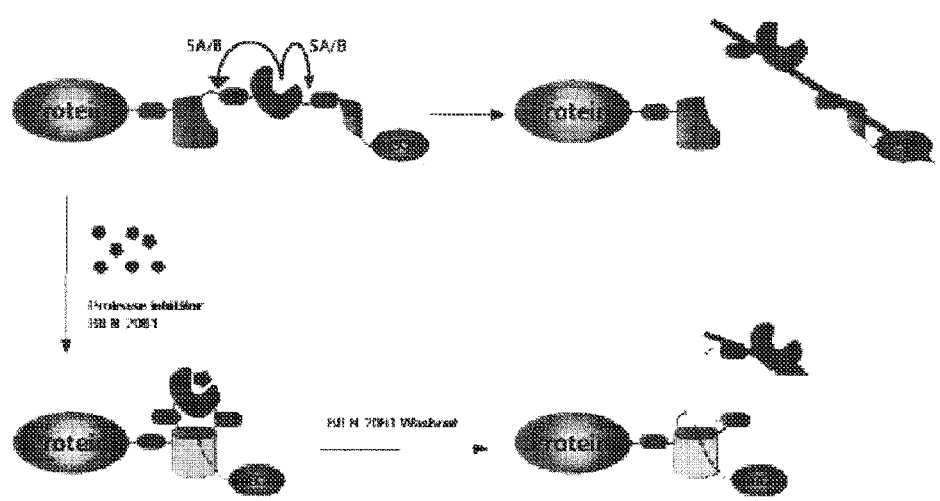
FIG. 16. Old copes of a chosen protein can be imaged after drug washout, enabling pulse chase labeling. Venus complementation, which is irreversible, is employed in a variation where a miniSOG is fused directly to the C-terminal fragment of Venus. After drug washout, both Venus and miniSOG remain attached to the protein of interest, allowing visualization by both fluorescence and electron microscopy.
Figure 17:
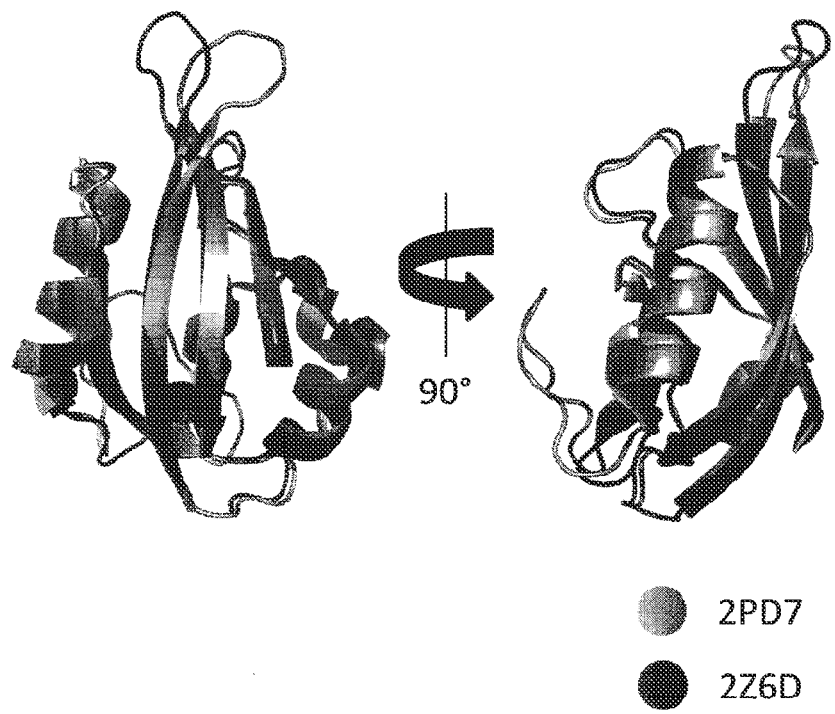
FIG. 17. Superposition of the peptide backbones of LOV2 domain from *Neurospora crassa* blue-light photoreceptor Vivid (PDB ID: 2PD7; Zoltowski et al., supra) and LOV1 domain from *Arabidopsis thaliana* Phot2 protein (PDB IDs: 2Z6D; Nakasako M. et al., supra). The superpositions were generated by aligning the Cα atoms of 2PD7 (residues 72-184) and 2Z6D (residues 134-235); rsmd=0.96 Å.

In one embodiment, a miniSOG protein comprises 106 amino acids, spanning residues 387-492 of *Arabidopsis thaliana* Phototropin 2. In another embodiment, a miniSOG protein comprises 106 amino acids of a LOV domain isolated from a phototropin protein of the same or different species, having homologous (i.e., the same) boundaries to residues 387-492 of *Arabidopsis thaliana* Phototropin 2. In another embodiment, a miniSOG protein comprises 106 amino acids of a LOV domain isolated from a non-phototropin protein of the same or different species, having homologous (i.e., the same) boundaries to residues 387-492 of *Arabidopsis thaliana* Phototropin 2. One of skill in the art will be able to determine homologous boundaries in any LOV domain, for example, by preparing a sequence alignment as is shown in FIG. 15. In one embodiment, the non-phototropin protein is a bacterial blue light receptor. In a specific embodiment, the non-phototropin protein is *Bacillus subtilis* YtvA or a homologue thereof. In another embodiment, the non-phototropin protein having a LOV domain is a LOV-histidine kinase. In a specific embodiment, the non-phototropin protein having a LOV domain is *Ostreococcus tauri* LOV-HK. In another embodiment, the non-photoropin protein having a LOV domain is a fungal photoreceptor. In a specific embodiment, the non-phototropin protein is *Neurospora crassa* Vivid (VVD) protein or a homologue thereof.

In another embodiment, the N- and C-terminal boundaries of the miniSOG may be shifted by from 1 to 10 amino acids to increase or decrease the size of the miniSOG, with respect to the corresponding wild type LOV domain. In a specific embodiment, a miniSOG is provided spanning from a residue selected from residues 377-397 to a residue selected from residues 482-502 of *Arabidopsis thaliana* Phototropin 2. In another embodiment, a miniSOG is provided comprising a LOV domain isolated from a phototropin protein of the same or different species, spanning from a residue selected from residues homologous to 377-397 to a residue selected from residues homologous to 482-502 of *Arabidopsis thaliana* Phototropin 2. In yet another embodiment, a miniSOG is provided comprising a LOV domain isolated from a non-phototropin protein of the same or different species, spanning from a residue selected from residues homologous to 377-397 to a residue selected from residues homologous to 482-502 of *Arabidopsis thaliana* Phototropin 2. In one embodiment, the non-phototropin protein is a bacterial blue light receptor. In a specific embodiment, the non-phototropin protein is *Bacillus subtilis* YtvA or a homologue thereof.

In another embodiment, the non-phototropin protein having a LOV domain is a LOV-histidine kinase. In a specific embodiment, the non-phototropin protein having a LOV domain is *Ostreococcus tauri* LOV-HK. In another embodiment, the non-photoropin protein having a LOV domain is a fungal photoreceptor. In a specific embodiment, the non-phototropin protein is *Neurospora crassa* Vivid (VVD) protein or a homologue thereof.

In another embodiment, the N- and C-terminal boundaries of the miniSOG may be shifted by from 1 to 5 amino acids to increase or decrease the size of the miniSOG, with respect to the corresponding wild type LOV domain. In a specific embodiment, a miniSOG is provided spanning from a residue selected from residues 382-392 to a residue selected from residues 487-497 of *Arabidopsis thaliana* Phototropin 2. In another embodiment, a miniSOG is provided comprising a LOV domain isolated from a phototropin protein of the same or different species, spanning from a residue selected from residues homologous to 382-392 to a residue selected from residues homologous to 487-497 of *Arabidopsis thaliana* Phototropin 2. In yet another embodiment, a miniSOG is provided comprising a LOV domain isolated from a non-phototropin protein of the same or different species, spanning from a residue selected from residues homologous to 382-392 to a residue selected from residues homologous to 487-497 of *Arabidopsis thaliana* Phototropin 2. In one embodiment, the non-phototropin protein is a bacterial blue light receptor. In a specific embodiment, the non-phototropin protein is *Bacillus subtilis* YtvA or a homologue thereof. In another embodiment, the non-phototropin protein having a LOV domain is a LOV-histidine kinase. In a specific embodiment, the non-phototropin protein having a LOV domain is *Ostreococcus tauri* LOV-HK. In another embodiment, the non-photoropin protein having a LOV domain is a fungal photoreceptor. In a specific embodiment, the non-phototropin protein is *Neurospora crassa* Vivid (VVD) protein or a homologue thereof.

In another embodiment, a miniSOG protein comprises a LOV domain spanning at least 100 consecutive amino acids of SEQ ID NO:9. In a specific embodiment, a miniSOG protein comprises a LOV domain spanning at least 106 consecutive residues of SEQ ID NO:9. In a more specific embodiment, a miniSOG protein comprises a LOV domain spanning at least residues 13 to 118 of SEQ ID NO:9.

In a related embodiment, a miniSOG protein comprises a LOV domain isolated from a phototropin protein of the same or different species, spanning at least 100 amino acids homologous to those of SEQ ID NO:9. In a specific embodiment, a miniSOG protein comprises a LOV domain isolated from a phototropin protein of the same or different species, spanning at least 106 amino acids homologous to those of SEQ ID NO:9. In a more specific embodiment, a miniSOG protein comprises a LOV domain isolated from a phototropin protein of the same or different species, spanning at least the residues homologous to residues 13 to 118 of SEQ ID NO:9.

In a related embodiment, a miniSOG protein comprises a LOV domain isolated from a non-phototropin protein of the same or different species, spanning at least 100 amino acids homologous to those of SEQ ID NO:9. In a specific embodiment, a miniSOG protein comprises a LOV domain isolated from a non-phototropin protein of the same or different species, spanning at least 106 amino acids homologous to those of SEQ ID NO:9. In a more specific embodiment, a miniSOG protein comprises a LOV domain isolated from a non-phototropin protein of the same or different species, spanning at least the residues homologous to residues 13 to 118 of SEQ ID NO:9. In one embodiment, the non-phototropin protein is a bacterial blue light receptor. In a specific embodiment, the non-phototropin protein is *Bacillus subtilis* YtvA or a homologue thereof. In another embodiment, the non-phototropin protein having a LOV domain is a LOV-histidine kinase. In a specific embodiment, the non-phototropin protein having a LOV domain is *Ostreococcus tauri* LOV-HK. In another embodiment, the non-photoropin protein having a LOV domain is a fungal photoreceptor. In a specific embodiment, the non-phototropin protein is *Neurospora crassa* Vivid (VVD) protein or a homologue thereof.

, the N- and C-terminus of a miniSOG protein can be variable. For example, as shown in an alignment of LOV domains from a variety of species (FIG. 15), amino acid sequences directly flanking the LOV domains on both the N- and C-terminal side have high levels of homology. One of skill in the art will easily be able to determine appropriate boundaries.

Likewise, the highly conserved nature of the primary, secondary, and tertiary structures of LOV domains across a wide range of species allow the use of any LOV domain in the construction of a miniSOG protein according to the present invention. The only limitations are that (i) the LOV domain must tightly bind to FMN, and (ii) that the LOV domain is engineered to efficiently generate singlet oxygen upon stimulation of the LOV domain-FMN complex with blue light. The second requirement can be met by mutating the conserved cysteine residue (corresponding to Cys 426 of AtPhot2) that forms a covalent bond with the FMN upon stimulation. As shown in FIG. 15, this cysteine, corresponding to residue 40 of the *Arabidopsis thaliana* Phototropin 2 LOV domain 2 (SEQ ID NO:7) and residue 52 of the other sequences present in FIG. 15, is well conserved. However, wild-type LOV domains exist with a glycine at this position. Provided these LOV domains bind FMN tightly, or may be engineered to do so, these LOV domains may also be used for the construction of a miniSOG as provided herein.

A. MiniSOG Fusion Proteins

The functional miniSOG polypeptides of this invention are useful to identify the ultrastructural location of proteins in cells. In this embodiment, a nucleic acid molecule encoding a miniSOG polypeptide is fused in frame to a nucleic acid molecule encoding a protein of interest in an expression vector. Upon expression inside the cell, the protein of interest can be localized based on fluorescence or EM microscopy. Typically the protein of interest is coupled to the miniSOG polypeptide via a flexible linker to ensure that both the target protein and miniSOG polypeptide functioned correctly and were efficiently folded. Methods for constructing and introducing such fusion proteins are well known in the art and are also discussed above.

Thus in one aspect, the present invention provides fusion proteins comprising a miniSOG polypeptide fused to a polypeptide of interest. In one embodiment, the fusion protein comprises the LOV2 domain of the AtPhot2 protein fused to a polypeptide of interest, wherein the LOV2 domain comprises at least a mutation at residue C426. In one embodiment, the mutation is selected from C426G, C426A, C426S, C426T, and C426P. In a preferred embodiment, the mutation is, C426G.

The LOV domain of a miniSOG fusion protein may contain further mutations with respect to the corresponding wild-type amino acid sequence, which may or may not improve the $^1O_2$ quantum yield, brightness of fluorescence, or tune the excitation or emission spectra of the miniSOG. In certain embodiments, one or more mutations are made at a residue corresponding to I387, N390, S394, S409, and F470, of AtPhot2, i.e., at a residue corresponding to I1, N4, S8, S23, C426, and F84 of SEQ ID NO:7.

Other proteins containing LOV domains suitable for use in miniSOG fusion proteins described herein can be found in plants, fungi, algae, and bacteria, including, but not limited to the genera *Arabidopsis, Populus, Phaseolus, Glycine, Spinacia, Medicago, Solanum, Vitis, Oryza, Physcomitrella, Bacillus, Brucella, Erythrobacter, Pseudomonas*, etc.

In one embodiment, the present invention provides a miniSOG fusion protein comprising a LOV domain having at least 80% identity to an amino acid sequence of SEQ ID NO:1 fused to a protein of interest. In another embodiment, the miniSOG fusion protein comprises a LOV domain having at least 85% identity to an amino acid sequence of SEQ ID NO:1 fused to a protein of interest. In another embodiment, the miniSOG fusion protein comprises a LOV domain having at least 90% identity to an amino acid sequence of SEQ ID NO:1 fused to a protein of interest. In another embodiment, the miniSOG fusion protein comprises a LOV domain having at least 95% identity to an amino acid sequence of SEQ ID NO:1 fused to a protein of interest. In yet another embodiment, In another embodiment, the miniSOG fusion protein comprises a LOV domain of SEQ ID NO:1 fused to a protein of interest. In yet other embodiments, the miniSOG fusion protein comprises a LOV domain having at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1 fused to a protein of interest.

In one embodiment, the present invention provides a miniSOG fusion protein comprising a LOV domain having at least 80% identity to an amino acid sequence of SEQ ID NO:2 fused to a protein of interest. In another embodiment, the miniSOG fusion protein comprises a LOV domain having at least 85% identity to an amino acid sequence of SEQ ID NO:2 fused to a protein of interest. In another embodiment, the miniSOG fusion protein comprises a LOV domain having at least 90% identity to an amino acid sequence of SEQ ID NO:2 fused to a protein of interest. In another embodiment, the miniSOG fusion protein comprises a LOV domain having at least 95% identity to an amino acid sequence of SEQ ID NO:2 fused to a protein of interest. In yet another embodiment, In another embodiment, the miniSOG fusion protein comprises a LOV domain of SEQ ID NO:2 fused to a protein of interest. In yet other embodiments, the miniSOG fusion protein comprises a LOV domain having at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:2 fused to a protein of interest.

In one embodiment, the present invention provides a miniSOG fusion protein comprising a LOV domain having at least 80% identity over at least 100 consecutive amino acids of a sequence selected from SEQ ID NOS:9 to 31 fused to a protein of interest, wherein the polypeptide comprises at least one mutation at the residue corresponding to C426 of AtPhot2 (i.e., C426 of SEQ ID NO:8 or C40 of SEQ ID NO:1). In a particular embodiment, the LOV domain of the miniSOG fusion protein comprises amino acids F-G of a sequence selected from SEQ ID NOS:9 to 31. In another embodiment, the miniSOG fusion protein comprises a LOV domain having at least 85% identity over at least 100 consecutive amino acids of a sequence selected from SEQ ID NOS:9 to 31 fused to a protein of interest. In another embodiment, the miniSOG fusion protein comprises a LOV domain having at least 90% identity over at least 100 consecutive amino acids of a sequence selected from SEQ ID NOS:9 to 31 fused to a protein of interest. In another embodiment, the miniSOG fusion protein comprises a LOV domain having at least 95% identity over at least 100 consecutive amino acids of a sequence selected from SEQ ID NOS:9 to 31 fused to a protein of interest.

In another embodiment, the miniSOG fusion protein comprises a LOV domain having at least 98% identity over at least 100 consecutive amino acids of a sequence selected from SEQ ID NOS:9 to 31 fused to a protein of interest. In yet other embodiments, the miniSOG fusion protein comprises a LOV domain having at least 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100 consecutive amino acids of a sequence selected from SEQ ID NOS:9 to 31 fused to a protein of interest. The miniSOG LOV domains having homology to SEQ ID NOS:9 to 31 bind FMN with high affinity and efficiently generate singlet oxygen upon stimulation with blue light.

In one embodiment, the miniSOG fusion proteins of the invention further comprise a mutation in their LOV domain at one or more residues corresponding to I1, N4, S8, S23, and F84 of SEQ ID NO:7. In one embodiment, the mutation is selected from those corresponding to DM, N4S, S8T, S23G, and F84L of SEQ ID NO:7. In a specific embodiment, the miniSOG LOV domain comprises I1M/C40G mutations with respect to SEQ ID NO:7. In another specific embodiment, the miniSOG LOV domain comprises I1M/C40G mutations with respect to SEQ ID NO:7.

VI. MiniSOG Polynucleotides

This invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

Oligonucleotides can also be chemically synthesized according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides can be achieved by isolation after agarose or native acrylamide gel electrophoresis or by anion-exchange HPLC as described in Pearson & Reanier, J. Chrom. 255:137-149 (1983). The sequence of the cloned genes and synthetic oligonucleotides can be verified after cloning using sequencing methods well known in the art.

Expression in prokaryotes and eukaryotes. To obtain high level expression of a cloned gene, such as those encoding miniSOG polypeptides of the invention, one typically subclones the polyncleotide encoding miniSOG into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al., supra. Bacterial expression systems for expressing proteins are available in, e.g., E. coli, Bacillus sp., and Salmonella (Palva et al., Gene 22:229-235 (1983); Mosbach et al., Nature 302:543-545 (1983)). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function. In one embodiment, when using a miniSOG polypeptide as a tag to localize a protein of interest by fluorescent or EM microscopy, especially during in vivo imaging or protein/cell ablation experiments, the nucleic acid encoding the fusion protein may be placed under the control of a native promoter for the protein of interest.

In addition to the promoter, the expression vector typically contains a transcription unit or expression cassette that contains all the additional elements required for the expression of the miniSOG-encoding nucleic acid in host cells. A typical expression cassette thus contains a promoter operably linked to the nucleic acid sequence encoding IFP and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMT010/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can also be regulated using inducible promoters. With inducible promoters, expression levels are tied to the concentration of inducing agents, such as tetracycline or ecdysone, by the incorporation of response elements for these agents into the promoter. Generally, high-level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high-yield expression systems not involving gene amplification are also suitable, such as using a baculovirus vector in insect cells, with an IFP-encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods can be used to produce bacterial, mammalian, yeast or insect cell lines that express large quantities of miniSOG or a fusion protein thereof, which may be purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the miniSOG or fusion protein thereof.

After the expression vector is introduced into the cells, the transfected cells are cultured under conditions favoring expression of miniSOG or the fusion protein thereof, which is recovered from the culture using standard techniques identified below.

In one aspect, the present invention provides polynucleotides encoding a miniSOG polypeptide. In one embodiment, the miniSOG polypeptide encoded by the nucleic acid consists of the LOV2 domain of the AtPhot2 protein, wherein the protein comprises at least a mutation at residue C426. In one embodiment, the mutation is selected from C426G, C426A, C426S, C426T, and C426P. In a preferred embodiment, the mutation is, C426G.

In one embodiment, the present invention provides a polynucleotide encoding a miniSOG polypeptide comprising at least 80% identity to an amino acid sequence of SEQ ID NO:1. In another embodiment, the polypeptide comprises at least 85% sequence identity to SEQ ID NO:1. In another embodiment, the polypeptide comprises at least 90% sequence identity to SEQ ID NO:1. In another embodiment, the polypeptide comprises at least 95% sequence identity to SEQ ID NO:1. In yet another embodiment, the polypeptide has the amino acid sequence of SEQ ID NO:1. In yet other embodiments, the polypeptide comprises at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1.

In one embodiment, the present invention provides a polynucleotide encoding a miniSOG polypeptide comprising at least 80% identity to an amino acid sequence of SEQ ID NO:2. In another embodiment, the polypeptide comprises at least 85% sequence identity to SEQ ID NO:2. In another embodiment, the polypeptide comprises at least 90% sequence identity to SEQ ID NO:2. In another embodiment, the polypeptide comprises at least 95% sequence identity to SEQ ID NO:2. In yet another embodiment, the polypeptide has the amino acid sequence of SEQ ID NO:2. In yet other embodiments, the polypeptide comprises at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:2.

In one embodiment, the present invention provides a polynucleotide encoding a miniSOG polypeptide comprising at least 80% identity over at least 100 consecutive amino acids of a sequence selected from SEQ ID NOS:9 to 31, wherein the polypeptide comprises at least one mutation at the residue corresponding to C426 of AtPhot2 (i.e., C426 of SEQ ID NO:8 or C40 of SEQ ID NO:1). In a particular embodiment, the miniSOG polypeptide comprises amino acids F-G of a sequence selected from SEQ ID NOS:9 to 31. In another embodiment, the polypeptide comprises at least 85% sequence identity over at least 100 consecutive amino acids of a sequence selected from SEQ ID NOS:9 to 31. In another embodiment, the polypeptide comprises at least 90% sequence identity over at least 100 consecutive amino acids of a sequence selected from SEQ ID NOS:9 to 31. In another embodiment, the polypeptide comprises at least 95% sequence identity over at least 100 consecutive amino acids of a sequence selected from SEQ ID NOS:9 to 31. In another embodiment, the polypeptide comprises at least 98% sequence identity over at least 100 consecutive amino acids of a sequence selected from SEQ ID NOS:9 to 31. In yet other embodiments, the polypeptide comprises at least 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100 consecutive amino acids of a sequence selected from SEQ ID NOS:9 to 31. The miniSOG polypeptides having homology to SEQ ID NOS:9 to 31 bind FMN with high affinity and efficiently generate singlet oxygen upon stimulation with blue light.

In one embodiment, the miniSOG polypeptides encoded by the nucleic acids provided herein further comprise a mutation at one or more residues corresponding to I1, N4, S8, S23, and F84 of SEQ ID NO:7. In one embodiment, the mutation is selected from those corresponding to DM, N4S, S8T, S23G, and F84L of SEQ ID NO:7. In a specific embodiment, the miniSOG comprises I1M/C40G mutations with respect to SEQ ID NO:7. In another specific embodiment, the miniSOG polypeptide comprises I1M/C40G mutations with respect to SEQ ID NO:7.

In one embodiment, the polynucleotide sequence encoding a miniSOG polypeptide is codon optimized for expression in a bacterial host cell, e.g., *E. coli*. In a particular embodiment, the nucleic acid comprises the sequence of SEQ ID NO:3 or 5. In another embodiment, the polynucleotide sequence encoding a miniSOG polypeptide is codon optimized for expression in a eukaryotic host cell or organism, e.g., a fungi, yeast, worm, mouse, rat, hamster, guinea pig, monkey, or human. In yet another embodiment, the polynucleotide sequence encoding a miniSOG polypeptide is codon optimized for expression in a mammalian host cell or organism, e.g., a mouse, rat, hamster, guinea pig, monkey. In a particular embodiment, the nucleic acid comprises the sequence of SEQ ID NO:4 or 6.

In one embodiment, the present invention provides a polynucleotide encoding a fusion protein, wherein the fusion protein comprises a miniSOG polypeptide of the invention fused to a protein of interest.

In one embodiment, the invention provides an expression vector, comprising; expression control sequences operatively linked to a nucleic acid molecule encoding a functional miniSOG polypeptide. In one embodiment, the expression vector encodes a fusion protein comprising a functional miniSOG polypeptide fused to a protein of interest.

In another embodiment, the invention includes a recombinant host cell, comprising; a nucleic acid molecule encoding a functional miniSOG polypeptide. In one embodiment, the nucleic acid molecule encodes a fusion protein comprising a functional miniSOG polypeptide fused to a protein of interest.

VII. Kits of the Invention

The present invention also provides kits to facilitate and/or standardize use of compositions provided by the present invention, as well as facilitate the methods of the present invention. Materials and reagents to carry out these various methods can be provided in kits to facilitate execution of the methods. As used herein, the term "kit" is used in reference to a combination of articles that facilitate a process, assay, analysis or manipulation.

Kits can contain chemical reagents (e.g., polypeptides or polynucleotides) as well as other components. In addition, kits of the present invention can also include, for example but not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and safe shipping, for example, in a box having a lid.

In some embodiments, for example, kits of the present invention can provide a miniSOG polypeptide of the invention, a miniSOG fusion protein of the invention, a polynucleotide vector (e.g., a plasmid) encoding a miniSOG polypeptide of the invention, bacterial cell strains suitable for propagating the vector, and reagents for performing assays of the invention (e.g., EM imaging, fluorescent imaging, protein ablation assays, etc.). Alternatively, a kit of the present invention can provide the reagents necessary to conduct mutagenesis of an LOV domain or miniSOG polypeptide to generate a protein variant having increased singlet oxygen quantum yield or modified fluorescence.

A kit can contain one or more compositions of the invention, for example, one or a plurality of miniSOG polypeptides, which can be a portion of a fusion protein, or one or a plurality of polynucleotides that encode the polypeptides. The miniSOG polypeptides can be a mutated polypeptide having increased singlet oxygen quantum yield or modified fluorescence or a fusion protein thereof. Where the kit comprises a plurality of miniSOG polypeptides, the plurality can be a plurality of the mutated polypeptides, fusion proteins thereof, or a combination thereof.

A kit of the invention also can contain one or a plurality of recombinant nucleic acid molecules, which encode miniSOG polypeptides, which can be the same or different, and can further include, for example, an operatively linked second polynucleotide containing or encoding a restriction endonuclease recognition site or a recombinase recognition site, or any polypeptide of interest. In addition, the kit can contain instructions for using the components of the kit, particularly the compositions of the invention that are contained in the kit.

Such kits can be particularly useful where they provide a plurality of different miniSOG polypeptides because the artisan can conveniently select one or more proteins having the singlet oxygen generation or fluorescent properties desired for a particular, application. Similarly, a kit containing a plurality of polynucleotides encoding different miniSOG polypeptides provides numerous advantages. For example, the polynucleotides can be engineered to contain convenient restriction endonuclease or recombinase recognition sites, thus facilitating operative linkage of the polynucleotide to a regulatory element or to a polynucleotide encoding a polypeptide of interest.

VIII. Uses of MiniSOGs

Among other uses, miniSOGs are versatile labels for correlated light and electron microscopy of genetically tagged proteins in cells, tissues, and organisms including intact nematodes and mice. In one aspect, miniSOGS can be used for the detection and localization of protein-protein interactions using fluorescence or electron microscopy. In another aspect, miniSOGs can be used as a fusion protein. In another aspect, miniSOGs can be used for photoablation experiments through the inactivation of proteins in close proximity to the miniSOG. In yet other aspects, miniSOGs can be used in proteomics, for example, for the determination of protein-protein proximities.

A. Protein Imaging by Fluorescence Microscopy

The miniSOG polypeptides provided by the present invention are useful for imaging a protein of interest in a cell, tissue, or whole organism by fluorescence or electron microscopy. Methods for imaging fluorescent proteins in cells, tissues, and whole organisms are well known in the art and include, without limitation, super-resolution microscopy (reviewed in Patterson G et al., Annu Rev Phys Chem. (2010) March; 61:345-67) intravital multiphoton microscopy (Piatkevich K D et al., Proc Natl Acad Sci U.S.A. (2010) March 23; 107 (12):5369-74), image and fluorescence correlation spectroscopy (Kolin D, Wiseman P. Cell Biochemistry and Biophysics. Humana Press Inc; (2007) pp. 141-164.), and fluorescent resonance energy transfer (FRET; reviewed in Jares-Erijman E A, Jovin T M, Nat. Biotechnol. (2003) November; 21(11): 1387-95). Any one of the techniques described in the above references (the disclosures of which are hereby expressly incorporated by reference in their entirety for all purposes) are suitable for use with the methods of the present invention.

In one embodiment, a miniSOG polypeptide is imaged by expressing the miniSOG polypeptide in a cell, exciting the polypeptide with a wavelength of light found in the excitation spectra of the miniSOG protein, and detecting the fluorescence of the miniSOG protein at a wavelength found in the emission spectra of the miniSOG protein. While various miniSOG proteins will have different excitation and emission spectra, the skilled artisan will readily be able to determine suitable wavelengths for exciting and detecting the fluorescence of a particular miniSOG polypeptide. Exemplary excitation and emission spectra for AtminiSOG0.2 are provided in FIG. 3B. In a preferred embodiment, the miniSOG polypeptide is excited at an excitation maximum wavelength and fluorescence is detected at an emission maximum wavelength.

In one embodiment, a protein of interest is imaged by expressing a fusion protein comprising a miniSOG polypeptide fused to the protein of interest in a cell, exciting the polypeptide with a wavelength of light found in the excitation spectra of the miniSOG protein, and detecting the fluorescence of the miniSOG protein at a wavelength found in the emission spectra of the miniSOG protein.

B. Protein Imaging by Electron Microscopy

The miniSOG polypeptides of the invention have been engineered to increase the production of singlet oxygen generation upon stimulation with blue light by eliminating the covalent attachment of FMN to a conserved cysteine residue situated in the core of the LOV. Singlet oxygen generated by the miniSOG proteins can be used to oxidize and polymerize diaminobenzidine (DAB) into a dense, brownish precipitate, which can be stained with osmium tetroxide and then becomes visible by electron microscopy (FIG. 14A). Detailed protocols for performing fluorescence photooxidation of DAB are known in the art (see, [2] and [6]). Accordingly, in one aspect, a miniSOG polypeptide enhances the EM contrast of a specific protein in a fixed tissue sample.

In one embodiment, a miniSOG polypeptide is imaged by expressing the miniSOG polypeptide in a cell, tissue, or organism, fixing the cell, tissue, or section of the organism (i.e., the sample), contacting the fixed cell, tissue, or organism with diaminobenzidine (DAB), polymerizing and precipitating the DAB by exciting the miniSOG polypeptide with blue light, staining the DAB polymer by contacting the polymer with osmium, and imaging the osmium stained cell, tissue or organism using electron microscopy.

In one embodiment, a protein of interest in a cell, tissue, or organism is imaged by expressing a fusion protein comprising a LOV domain polypeptide (i.e., a miniSOG polypeptide)

fused to the protein of interest, wherein the LOV domain polypeptide binds a flavin mononucleotide (FMN) with high affinity and efficiently generates singlet oxygen upon stimulation with blue light; contacting the fixed cell, tissue, or organism with diaminobenzidine (DAB); polymerizing and precipitating the DAB by exciting the LOV domain polypeptide with blue light; staining the DAB polymer by contacting the polymer with osmium, and imaging the osmium stained cell, tissue or organism using electron microscopy. In one embodiment, the method comprises ultrastructural 3-dimensional localization of the protein of interest via electron tomography or serial section block face scanning electron microscopy.

In one embodiment, miniSOGs can be used to generate a correlated light and electron microscopy image (i.e., localization) of genetically tagged proteins in cells, tissues, and organisms including intact nematodes and mice.

C. Detection and Localization of Protein-Protein Interactions

FRET is a general, non-destructive, spectroscopic effect that occurs under certain circumstances when two fluorophores (a donor fluorophore and acceptor fluorophore) approach closer than about 100 Å. The efficiency of FRET between the two fluorophores is highly distant dependent, and this fact can be exploited to monitor the dynamic association of the fluorophores, or two fluorophore tagged macromolecules. By monitoring FRET between one or more fluorescent proteins it is possible to develop sensitive, non-invasive, cell based assays for a range of activities including proteolysis (see, U.S. Pat. No. 5,981,200), analyte determinations (see U.S. Pat. No. 5,998,204) and protein-protein interactions. FRET is most readily determined by measuring the relative emissions of the donor and acceptor fluorophore and then by calculating the emission ratio of these two values. A high degree of FRET is indicted by a high value of the ratio of [acceptor emission/donor emission], and a low degree of FRET is indicated by a low value of this ratio. FRET may also may determined by measuring the degree of donor fluorescence quenching, a measurement method that has the important advantage over emission ratioing in that this value is dependent of the concentration the acceptor.

In one embodiment the functional miniSOG polypeptides are useful for FRET based assays for detecting protein-protein interactions. This approach enables an additional range of post-translational activities to be assayed. In this embodiment, a first protein is typically covalently coupled to donor fluorescent protein (such as a miniSOG polypeptide of the invention), and a second protein is covalently coupled to the acceptor fluorescent protein (such as a fluorescent protein with an excitation spectra that overlaps the emission spectra of the miniSOG polypeptide). As previously, the donor and acceptor fluorescent proteins are selected to optimize the degree of FRET. Binding of the first protein to the second protein results in the association of the donor and acceptor fluorescent proteins resulting in an enhancement of the degree of FRET between them. This results in a measurable change in the donor and acceptor emission ratio. This approach thus enables the identification and detection of protein-protein interactions between defined proteins, as well as the ability to detect post-translational modifications that influence these protein-protein interactions.

To identify and characterize the interaction of two test proteins, the method would typically involve; 1) the creation of a first fusion protein comprising the first test protein coupled to the miniSOG polypeptide, and a second fusion protein comprising the second test protein coupled to an acceptor fluorescent protein; 2) the introduction of the fusion proteins in combination into a cell, tissue, or organism, and optionally the introduction of the donor and acceptor fluorescent proteins (without fusion proteins) into a control cells, tissue, or organism; 3) the measurement of the donor and acceptor emission ratios in the cell, tissue, or organism and optionally in the control cell, tissue, or organism; and optionally 4) comparison of the emission ratio in the control cells, compared to the emission ratio in the test cells. In one embodiment, the method comprises localization of the interaction by fluorescent imaging methods.

If the cells expressing the fusion proteins exhibits an emission ratio with a significantly altered value compared to the control cells containing the fluorescent proteins alone, then the results indicate that the two proteins do interact under the experimental conditions chosen. Conversely, if the emission ratios in the control cells, and in the test cells are approximately the same (after taking into account differences in relative expression of the fluorescent proteins), then the results indicate that the proteins probably don't interact strongly under the test conditions.

The method also enables the detection and characterization of stimuli (such as receptor stimulation) that cause two proteins to alter their degree of interaction. In this case, a cell line is created that expresses the first and second fusion proteins, as described above, comprising interaction domains that exhibit, or are believed to exhibit post-translational regulated interactions. For example, post-translational modification by phosphorylated of serine or threonine residues can modulate 14-3-3 domain interactions, tyrosine phosphorylated can influence SH2 domain interactions, the redox state can influence disulfide bond formation. The cell line is then exposed to a test stimulus to determine whether the stimulus regulates the interaction of the two proteins. If the stimulus does regulate the interaction of the two proteins, then this will result in a modulation of the coupling of the two fluorescent proteins, subsequently resulting in a modulation of the degree of FRET and hence fluorescence emission ratio in the treated cells, compared to the non-treated cells.

The invention is also readily amenable to identifying new protein-protein interactions. For example, where a first protein is known, but the protein(s) with which it interacts are unknown. In this case, a first fusion protein is made between the first protein and the donor fluorescent protein (or acceptor fluorescent protein) and cloned into a suitable, expression vector. Second, a library of test proteins, for example isolated from a cDNA expression library, is fused in frame to the acceptor fluorescent protein (or donor fluorescent protein) and subcloned into a second expression vector. Typically the first fusion protein would be then be introduced into a population of test cells and single clones identified that stably expressed the fusion protein. The library of test proteins (typically in the form of expression vectors) would be introduced into the clonal cells, stably expressing the first fusion protein. The resulting transformed cells would then be screened to identify cells with altered FRET compared to the control cells. Suitable clones expressing the fusion proteins with modulated FRET, (i.e., altered emission ratios) may then be identified, isolated and characterized, for example by fluorescence activated cell sorting (FACS™). To confirm that the altered emission ratio was indeed the result of FRET, and not due to alterations in the expression level of the acceptor fluorescent protein, secondary measurements of donor emission quenching in the presence and absence of the acceptor would usually be completed. This could be achieved, for example, by measuring donor emission before and after photobleaching of the acceptor. Those library members that display fusion proteins with larger relative changes in emission ratio may then be identified by the degree to which emission ratio is altered for each library member after exposure to the library of test fusion proteins.

Likewise, protein-protein interactions can be detected by bleaching a fluorescent protein using singlet oxygen generated by the excitation of a miniSOG using blue light. In this regard, a first fusion protein comprising a miniSOG polypeptide (i.e., a LOV domain engineered for the efficient generation of singlet oxygen upon stimulation with blue light) conjugated to a first protein of interest and a second fusion protein comprising a fluorophore readily bleached by singlet oxygen fused to a second protein of interest are expressed in a cell, tissue, or organism; singlet oxygen is generated by exciting the miniSOG with blue light; and the fluorescence of the fluorophore fused to the second protein of interest is determined. If the fluorescence is decreased after exposure of blue light, then the second protein of interest is present in close proximity to the first protein of interest. The extent of the fluorophore bleaching after exposure to blue light is proportional to the proximity of the first and second fusion proteins, i.e., the greater the extent of the bleaching, the closer the two proteins are in the cell, tissue, or organism.

D. Chromophore Assisted Light Inactivation (CALI) of Proteins

Fluorophores that generate reactive oxygen species (e.g., singlet oxygen) can be used as photosensitizers to inactivate proteins in close proximity to the fluorophore, a process known as chromophore assisted light inactivation (CALI; reviewed in Wombacher and Cornish, J Biophotonics (2011) June; 4(6):391-402. In this regard, the miniSOG polypeptides of the invention have been engineered to efficiently generate singlet oxygen species upon activation with blue light. Accordingly, in one aspect, the present invention provides a method for the photoablation of a protein of interest through the stimulation of a miniSOG protein with blue light.

In one embodiment, a method is provided for inactivating a protein of interest in a cell, tissue, or organism, the method comprising the steps of: expressing a fusion protein comprising a miniSOG polypeptide (i.e., a LOV domain engineered for the efficient generation of singlet oxygen upon stimulation with blue light) conjugated to the protein of interest in a cell, tissue, or organism; and stimulating the generation of singlet oxygen by irradiating the cell, tissue, or organism with blue light.

In certain embodiments, the method can be used in conjunction with a functional assay or imaging set-up to determine the effects of inactivating the protein of interest. In one embodiment, the fusion protein is expressed in a cell that otherwise lacks expression of the protein of interest, in order to simulate complete loss of the activity provided by the protein of interest.

E. Photoablation of Cells

Figure 14B:
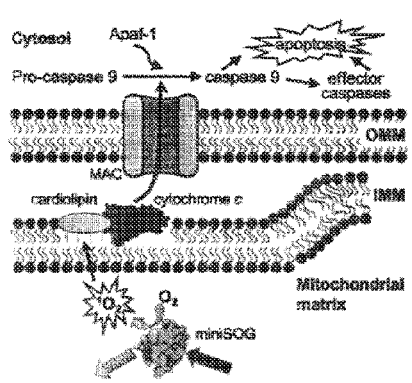
Figure 14C:
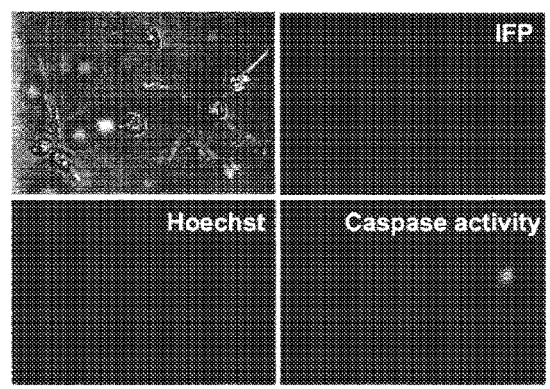

In one aspect, the present invention provides a method for photoablating a cell by expressing a miniSOG fusion protein comprising a miniSOG fused to a mitochondrial protein or a polypeptide that localizes to mitochondria; and irradiating the cell with blue light. Upon blue light excitation, the miniSOG fusion protein generates singlet oxygen in the matrix of mitochondria, which oxidizes cardiolipin. Cytochrome c is then released from oxidized cardiolipin and translocates to cytosol and activates Apaf-1, which leads to activation of initiator caspase 9. Active caspase 9 then triggers caspase cascade by activating effector caspases, leading to apoptosis. (FIG. 14C).

Genetically-targeted cell photoablation can be used to study cell lineages in intact organisms with high spatiotemporal resolution. Current well-established methods for such application are laser ablation and physical surgery. Both methods are labor-intensive and time-consuming, with poor reproducibility. Newer methods like using toxic genes for genetically-targeted cell ablation suffer from unintended cell killing due to minimal leakiness of gene expression, with poor spatiotemporal resolution. Accordingly, in one embodiment, the miniSOG fusion protein is placed under the control of a cell lineage-dependent promoter.

In certain embodiments, the cell expressing the miniSOG fusion protein is grown in cell or tissue culture. In another embodiment, the miniSOG fusion protein is expressed in a cell of an intact organism.

IX. Methods of Engineering a MiniSOG

In one aspect, the present invention provides a method for engineering a miniSOG polypeptide by mutating a wild-type LOV domain polypeptide to redirect the energy captured by a bound FMN from its wild-type use in generating a covalent bond to the generation of singlet oxygen species. In one embodiment, the method comprises the steps of: providing a polynucleotide encoding a LOV domain polypeptide capable of binding FMN with high affinity; and mutating the polynucleotide such that the encoded LOV domain polypeptide is not capable of forming a covalent bond with FMN upon stimulation with blue light, thereby forming a miniSOG polypeptide capable of generating singlet oxygen upon stimulation with blue light.

Further mutation of the miniSOG amino acid sequence may be performed to increase the singlet oxygen quantum yield and/or alter the fluorescent properties of the miniSOG polypeptide. Mutations in residues that are not strictly conserved in nature and residues whose side-chains are surface exposed or known to contribute to protein-protein interactions, rather than protein-FMN interactions, will be highly tolerated in a miniSOG polypeptide.

In one embodiment, mutations are introduced into the polynucleotide encoding the miniSOG polypeptide by rational design. In one embodiment, the well known crystallographic structure of LOV domains may be used to select residues for further mutation. Where the molecular structure of a particular LOV domain is not available, the primary sequence may modeled onto a known LOV structure or composite of LOV structures, for example by threading the sequence. In order to increase the singlet oxygen quantum yield of the miniSOG, mutations may be made at residues proximal to, but not critical to the interaction between the LOV domain and FMN. In this regard, access of oxygen to the FMN may be increased without perturbing the high affinity of the LOV domain-FMN interaction.

In another embodiment, random or semi-random mutations are introduced into the encoded polypeptide sequence and the resulting miniSOG polypeptides are screened for a desired characteristic. For example, mutated miniSOG polypeptides may be screened for increased singlet oxygen quantum yield, increased fluorescent brightness, shifted fluorescent excitation or emission spectra, etc.

For example, mutated miniSOG polypeptides may be screened for increased singlet oxygen generation (i.e., an increased quantum yield) by: (i) mutating a plurality of polynucleotides encoding miniSOGs, (ii) fusing the mutated sequences to polynucleotides encoding a fluorophore readily bleached by singlet oxygen, for example an infrared fluorescent protein (IFP; see, U.S. Patent Application Publication No.: 2011/0177003); (iii) expressing the fusion polypeptides in a host cell (e.g., *E. coli*); and (iv) screening for *E. coli* colonies with decreased fluorescence from the fluorophore after exposure to blue light.

X. Discussion of Experimental Results

Figure 10:
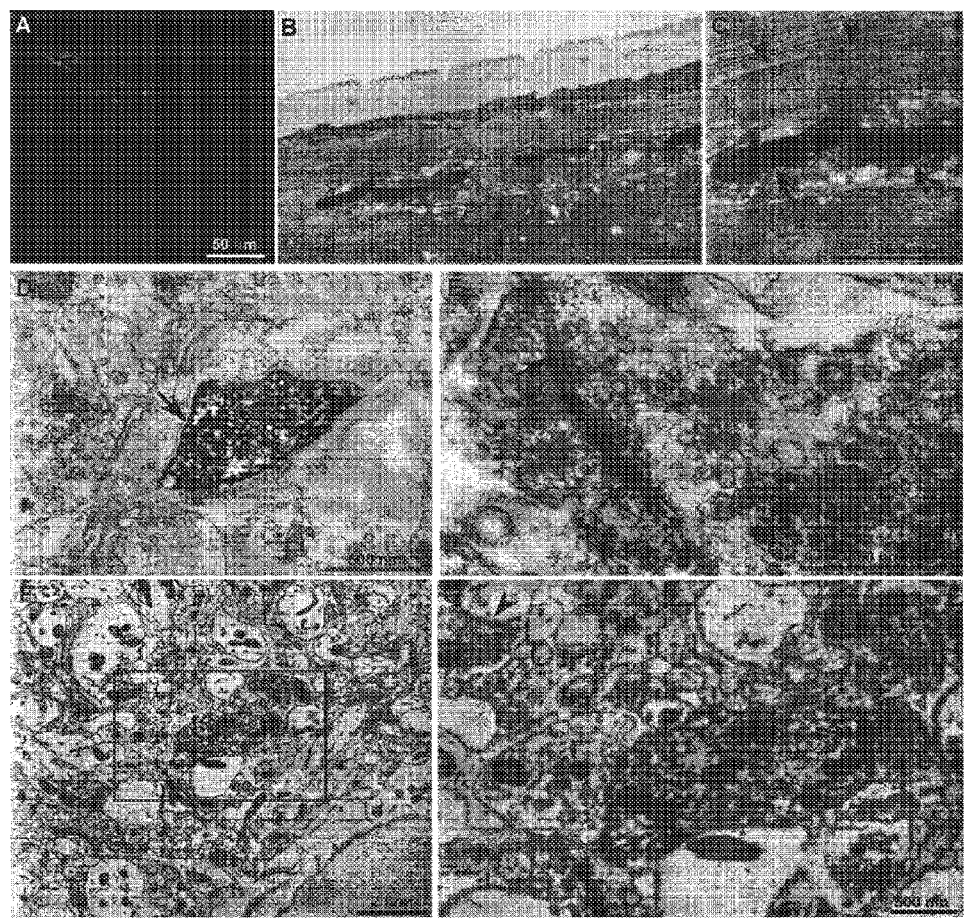
FIG. 10. (A) Confocal fluorescence image of miniSOG targeted to the mitochondria in body wall muscles of *C. elegans*. (B-C) Thin section EM images of a portion of *C. elegans* showing a subset of labeled mitochondria in the body wall muscle (arrow) and adjacent unlabeled mitochondria in a different cell type (arrowheads). (D-E) Ultrastructural localization of AtminiSOG0.2-labeled synaptic cell-adhesion molecules (SynCAMs) in cultured cortical neurons. (D) SynCAM1 fusion reveals uniform membrane labeling at the presynaptic apposition (arrow). (E) SynCAM2 fusion shows postsynaptic membrane labeling (pointed by arrow). Ultrastructural details including synaptic vesicles and nerve terminal substructure were well preserved in both (D) and (E). (F-G) Ultrastructural localization of AtminiSOG0.2-labeled synaptic cell-adhesion molecule 2 (SynCAM2) in intact mouse brain. (F) A large area (~14 μm×14 μm) of one of the tissue sections imaged by serial block-face scanning electron microscopy. (G) Enlargement of the region boxed in (A) reveals postsynaptic membrane labeling (pointed by arrow) apposing a presynaptic bouton containing vesicles. Ultrastructural details including synaptic vesicles and membrane-bound structures of synapses were well preserved and easily recognizable (e.g., arrowhead in the upper left). Bar A, 50 microns; B-C, 500 nm; D-E, 500 nm; F, 2 microns; G, 500 nm.

The successful localization of a variety of proteins by light and EM in cultured cells as well as mitochondria in *C. elegans* and SynCAM2 in intact mouse brain demonstrates the value of miniSOG for correlated light and EM localization of specific proteins in cells and multicellular organisms. MiniSOG is advantageous over conventional immuno-gold staining because the protein of interest is genetically tagged before fixation and all subsequent components ($O_2$, DAB, and $OsO_4$) are small molecules that easily permeate tissues. Tissues or cells can be fixed using established methods for good preservation of ultrastructure without concern for retention of antigenicity. Thus, permeabilizing detergents such as Triton X-100 that degrade membranes to facilitate the diffusion of bulky antibodies and secondary labels are unnecessary. This is demonstrated by the well-preserved ultrastructure in SynCAM-AtminiSOG0.2 labeled mice where unlabeled synapses (arrowhead), nonsynaptic plasma membrane, and synaptic vesicles are clearly observed (FIG. 10). Such landmarks were essential to assign the precise location of the SynCAMs. While super-resolution fluorescence techniques [38]-[40] could provide improved localizations, each landmark of interest would need to be labeled with fluorophores emitting at different color.

MiniSOG probes have several advantages over other correlated LM/EM probes. MiniSOG needs no exogenous cofactors and produces $^1O_2$ with about 20 times higher quantum efficiency than ReAsH on a tetracysteine motif. Therefore, miniSOG photooxidation has considerably better sensitivity and lower background than ReAsH labeling. MiniSOG is much smaller than GFP, and unlike GFP can mature and become fluorescent in the absence of $O_2$. GFP-based photooxidation is very difficult due to its extremely low $^1O_2$ quantum yield [13]. Genetically encoded horseradish peroxidase is tetrameric and far larger than GFP, only becomes functional inside the secretory pathway [6], and produces relatively diffuse precipitates [1], [7], [8]. Metallothionein fusions would seem most appropriate for purified macromolecules [3], because imaging of intact cells requires them to survive prolonged incubation in high concentrations of $Cd^{2+}$ or $Au^+$ [4], [5] and not to express endogenous metallothionein.

Our results with miniSOG fusions demonstrate that SynCAM1 and SynCAM2 are localized to pre- and post-synaptic membranes, respectively, and these observations are consistent with the reported strong heterophilic interaction between SynCAM1 and SynCAM2 in the formation of trans-synaptic structures [41]. The presynaptic membrane localization of SynCAM1 is also consistent with the recent report that SynCAM1 is expressed in growth cones in the early developmental stages of mouse brain and is involved in shaping the growth cones and the assembly of axo-dendritic contact [41]. Analogous trans-synaptic pairs include neurexinlneuroligin [42], EphrinB/EphB, and netrinG/netrin-G ligand (NGL). New synaptic proteins continue to be reported, such as leucine rich repeat transmembrane proteins (LRRTMs), NGL-3, and leukocyte common antigen-related (LAR) [43], [44]. The large variety of these molecules may be necessary to establish and support the great diversity of neuronal synapses; dissecting their locations within synapses will be a complex task.

As demonstrated here, our miniSOG-based photooxidation technique provides a method to determine the detailed distribution of these and other important macromolecules. In combination with SBFSEM, miniSOG fusion proteins should find wide applications in the ultrastructural localization of proteins, including 3-d reconstruction of neuronal circuits by large scale automated SBFSEM to mark cells of interest and trace them across large numbers of sections [37]. Additionally, a logical next step will be to further enhance the preservation of cellular ultrastructure in these types of specimens by combining chemical fixation and high pressure freezing [45] with photooxidation using miniSOG.

Spatiotemporally controlled local photogeneration of $^1O_2$ should also be useful for rapidly inactivating proteins of interest [46], reporting protein proximities over tens of nanometers [47] by $^1O_2$ transfer from a SOG to a $^1O_2$ sensitive fluorescent protein (e.g., IFP1.4) and ablating cells by photodynamic damage. Thus, further development and application of miniSOG using $^1O_2$ generation should greatly expand its utility in imaging and functional studies.

EXAMPLES

Example 1

Structure Based Design of MiniSOG

The LOV (light, oxygen, and voltage) domain of phototropin (a blue light photoreceptor) binds flavin mononucleotide (FMN) [16], [17], which by itself is an efficient singlet oxygen photosensitizer [18]. FMN is ubiquitous in cells and performs indispensable biological functions such as mitochondrial electron transport, fatty acid oxidation, and vitamin metabolism [19].

In phototropin, the excited state energy of FMN is consumed to form a covalent bond with a cysteine [20]. To divert this energy into $^1O_2$ generation, we carried out saturation mutagenesis of the relevant cysteine (Cys426) of the LOV2 domain of *Arabidopsis thaliana* phototropin 2 (AtPhot2). To screen for optimal $^1O_2$ production, these site-specific mutants were fused to an infrared fluorescent protein, IFP1.4, which is readily bleached by $^1O_2$ [21]. Colonies of *E. coli* expressing the fusion proteins were imaged in the IFP channel (ex 684/em 708 nm) before and after blue light (488 nm) illumination (FIG. 1A). Irradiation of *E. coli* colonies expressing the fusion library at 480/30 nm led us to identify two colonies both containing the mutant C426G, based on significantly decreased IFP1.4 brightness from 100 and 96 to 27 and 28 respectively. Several colonies showed a decrease of IFP fluorescence from wild-type colonies and two with the largest decrease (~70%) had the single site substitution of Cys426 to Gly. The small side chain of the glycine residue may provide space around the cofactor that would allow $O_2$ close apposition to FMN for efficient energy transfer.

Figure 3A:
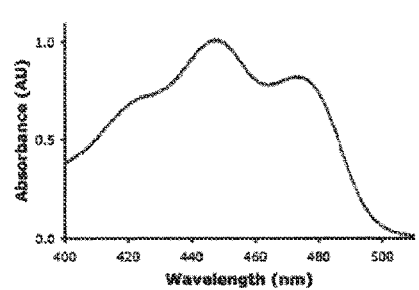
FIG. 3. (A) Absorbance spectrum of miniSOG0.2 determined between 400 nm and 500 nm (B) Normalized absorbance (left) and emission (right) spectra of miniSOG0.2. The fluorescence quantum yield of miniSOG0.2 was determined to be 0.30. (C) ADPA degradation by miniSOG0.2. ADPA was mixed with miniSOG0.2 in PBS and illuminated at 480/30 nm. ADPA emission spectra taken after indicated illumination times. (D) Degradation of ADPA by illumination of miniSOG0.2 (▲) or free FMN (♦). Flavin mononucleotide (FMN) was used as the standard for the quantum yield measurement. The data represents one typical measurement. The averaged absorbance intensity of FMN and miniSOG0.2 in this measurement is 0.064 and 0.070 respectively in arbitrary units. Singlet-oxygen-generation quantum yield of miniSOG0.2 was determined to be 0.47±0.05 (from three independent measurements).
Figure 3B:
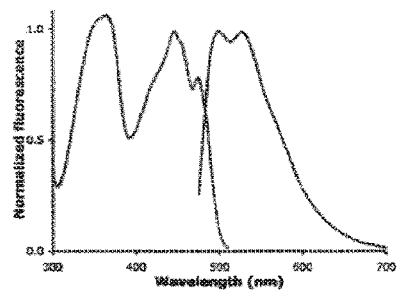
Figure 3C:
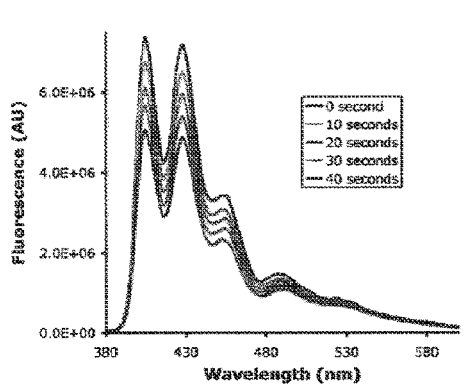
Figure 3D:
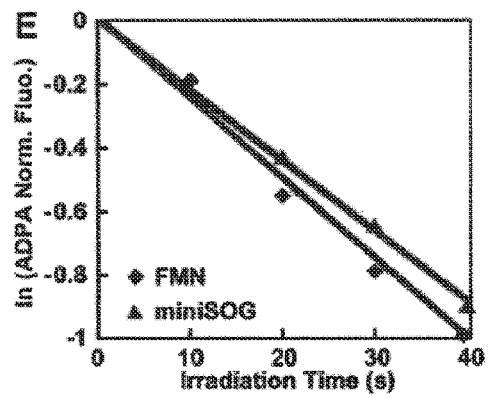

To increase the brightness of the C426G mutant, we also performed saturation mutagenesis of other residues surrounding the chromophore binding site. DNA shuffling of the improved mutants plus random mutagenesis led to a new protein, AtminiSOG0.2 (106-residue) (FIGS. 1B and C, FIG. 2), which absorbs maximally at 448 nm with a shoulder at 473 nm with extinction coefficients $(16.7±0.7)×10^3$ and $(13.6±0.5)×10^3$ $M^{-1}cm^{-1}$, respectively (FIGS. 3A and B). Excitation of AtminiSOG0.2 leads to green emission with two peaks at 500 and 528 nm (FIG. 3B). The $^1O_2$ quantum yield of miniSOG0.2 (0.47±0.05) was measured using anthracene-9,10-dipropionic acid (ADPA) as a $^1O_2$ sensor (FIG. 1E) [22]. Free FMN was used as the standard for the measurement of $^1O_2$ generation (quantum yield 0.51) [10].

Example 2

Characterization of MiniSOG

AtminiSOG0.2 was determined by light scattering to be monomeric in solution, with a molecular weight of 13.9±0.4 kDa, close to the theoretical value of 15.3 kDa. Absence of oligomerization was further supported by the good separation by gel filtration of AtminiSOG0.2 from its tandem dimer (td-miniSOG). Mass spectrometry confirmed that the flavin cofactor is FMN. Equilibrium dialysis reported a dissociation constant of 170±8 pM (Table 2), similar to values for some flavoproteins (e.g., 260±60 pM for a flavodoxin [23]) and consistent with the crystal structures of LOV domains, which show FMN deeply buried inside the protein core [24].

TABLE 2

MiniSOG equilibrium dialysis.

| Dialysis time (hrs) | [apo] * [FMN]/[holo] ($10^{-12}$M) |
|---|---|
| 24 | 123.8 ± 5.7 |
| 48 | 173.6 ± 5.3 |
| 72 | 170.3 ± 8.4 |

Furthermore, overexpression of AtminiSOG0.2 in HEK293 cells caused the FMN content to increase ~3-fold, presumably to keep miniSOG nearly saturated with FMN, but caused no obvious toxicity in the absence of light (Table 3). Feedback pathways involving enzymes such as riboflavin kinase (EC 2.7.1.26) and FAD (flavin adenine dinucleotide) diphosphatase (EC 3.6.1.18) probably regulate intracellular FMN to titrate endogenous flavoproteins and miniSOG [25]. Riboflavin kinase phosphorylates riboflavin into FMN, while FAD diphosphatase catalyzes the production of FMN from FAD.

TABLE 3

Growth rate of HEK293 cells.

| | Cell number ($10^3$) | | |
|---|---|---|---|
| | Day 0 | Day 1 | Day 2 |
| miniSOG | 200 | 390 | 940 |
| EGFP | 200 | 400 | 920 |
| untransfected | 200 | 400 | 930 |

*transfection efficiency >90%

Transfected CHO cells expressing AtminiSOG0.2 (FIG. 4) are brightly green fluorescent (FIG. 4A). After irradiation at 480/30 nm, DAB was photoconverted showing darkened color in the transmitted light image (FIG. 4C), compared to that before irradiation (FIG. 4B). The green fluorescence is well correlated with DAB photoconversion, demonstrating that it is the singlet oxygen generated from miniSOG that oxidizes and polymerizes DAB into dense precipitate shown by the darkened color. The top arrow in FIGS. 4B and C show a tranfected CHO cell with correlated green fluorescence and DAB photoconversion, while the bottom arrow indicates an untransfected cell with no green fluorescence and no DAB photoconversion.

Expression of AtminiSOG0.2 in nucleus of HeLa cells by histone (H2B) fusion demonstrates correlated green fluorescence (FIG. 4D) and DAB photoconversion (FIG. 4E) in nucleus. No or little green fluorescence was observed outside nucleus, indicating that the concentration of free FMN outside nucleus was not increased after overexpression of miniSOG, which incorporates endogenous FMN as the chromophore. This is well correlated with the fact that no or little DAB photoconversion occurred outside the nucleus. This observation indicates that there is no or little background in DAB photoconversion using miniSOG.

Example 3

Figure 5:
FIG. 5. High resolution image of an adhesion protein SynCAM1-AtminiSOG0.2 fusion protein by electron microscopy.

Correlated Fluorescence and Electron Microscopic Imaging of Various Proteins and Organelles Using miniSOG High resolution image of an adhesion protein SynCAM1 by electron microscopy. SynCAM1 was fused to AtminiSOG0.2 and expressed in cortical neurons, followed by DAB photoconversion upon 480/30 nm irradiation. The sample was then post-fixed with 1% osmium tetroxide, sectioned and imaged under electron microscopy. The resulting image is shown in FIG. 5.

Figure 11:
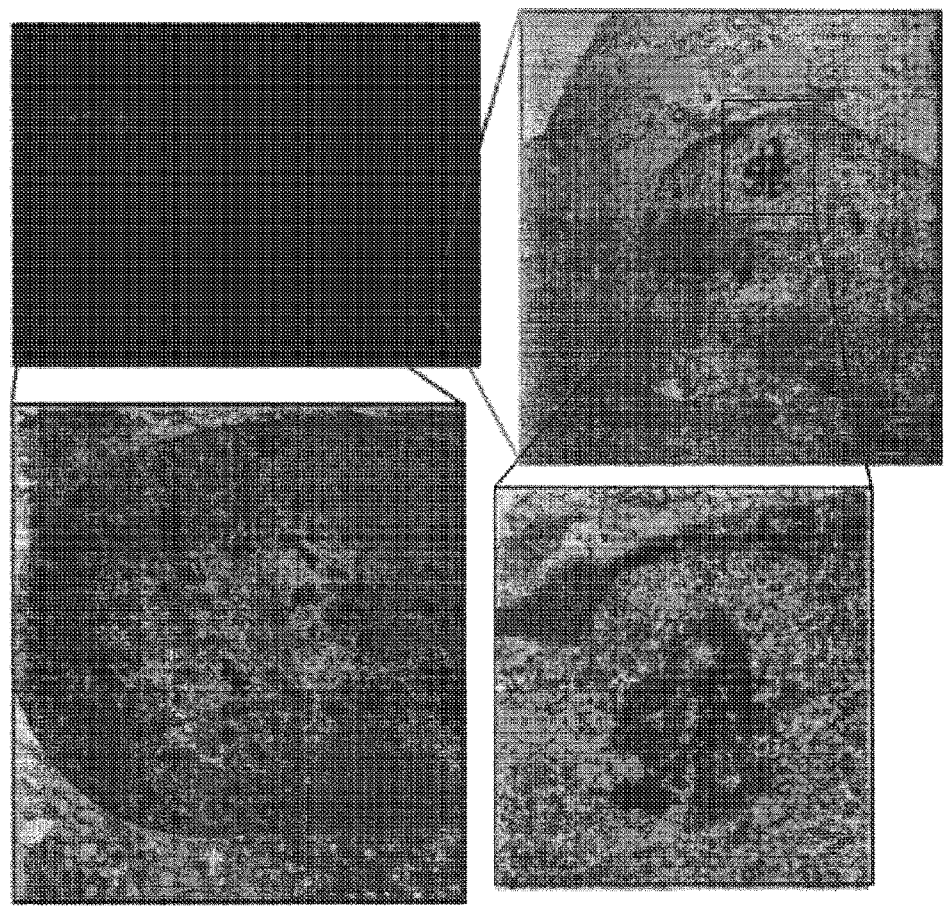
FIG. 11. Correlated fluorescence and electron microscopic imaging of various proteins and organelles using AtminiSOG0.2.

Histone H2B was fused to AtminiSOG0.2 and expressed in HeLa cells. The fluorescence image showing the nucleus can be correlated with high resolution electron microscopic images showing more detailed chromatin structures. The resulting image is shown in FIG. 11.

Overexpressed AtminiSOG0.2-tagged connexin43 successfully forms gap junctions in HeLa cells as observed from the fluorescence image (FIG. 12A) based on the miniSOG fluorescence, and transmitted light image (FIG. 12B) after DAB photoconversion. The electron microscopy image (FIG. 12C) shows the gap junctions at ultrahigh resolution. No other method has achieved such high resolution and quality in gap junction imaging.

AtminiSOG0.2-tagged α-actinin successfully binds to actin filaments in HeLa cells as observed from the fluorescence image (FIG. 12D) based on the miniSOG fluorescence, and transmitted light image (FIG. 12E) after DAB photoconversion. The electron microscopic image (FIG. 12F) shows the actin-filament-bound α-actinin.

MiniSOG was then fused to mitochondria-targeting sequence of cytochrome c which resides in the matrix. Overexpression of the fusion protein in HeLa cells shows successful labeling of mitochondria from the fluorescence image (FIG. 12G) based on the miniSOG fluorescence, and transmitted light image (FIG. 12H) after DAB photoconversion. The high-resolution electron microscopic image (FIG. 12I) shows well-preserved mitochondrial structure.

Example 4

Figure 13A:
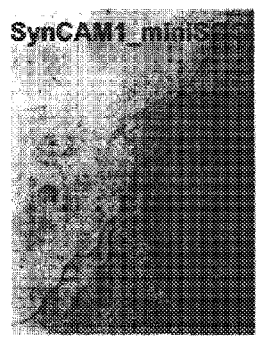
FIG. 13. Application of AtminiSOG0.2 in imaging SynCAM1 (A) and SynCAM2 (B and C) proteins in intact mice by electron microscopy.
Figure 13B:
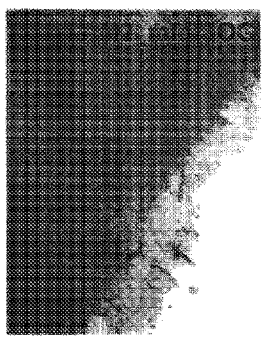
Figure 13C:

Application of miniSOG in Imaging Proteins in Intact Mice by Electron Microscopy Synaptic cell adhesion molecules (SynCAM 1 and SynCAM2) were fused to AtminiSOG0.2 and both fusion genes (SynCAM1-miniSOG and SynCAM2-miniSOG) were expressed in mice using in utero electroporation method. The transmitted light images show successful DAB photoconversion and neuron labeling of sectioned brain tissues expressing SynCAM1-AtminiSOG0.2 (FIG. 13A) and SynCAM2-AtminiSOG0.2 (FIG. 13B). The high-resolution electron microscopic image (FIG. 13C) shows postsynaptic localization of SynCAM2. These results demonstrate that miniSOG can be used to image proteins expressed in intact mice then processed for electron microscopy.

Example 5

Genetically Targeted Cell Photoablation by miniSOG

Cells expressing mitochondria-targeted miniSOG (mito-miniSOG) undergo apoptosis after light illumination (480±15 nm, 50 mW/cm$^2$ for 40 minutes). The cartoon shown in FIG. 14B illustrates a basic mechanism of how genetically targeted cell photoablation is achieved. Upon blue light excitation, miniSOG generates singlet oxygen in the matrix of mitochondria, which oxidizes cardiolipin. Cytochrome c is then released from oxidized cardiolipin and translocates to cytosol and activates Apaf-1, which leads to activation of initiator caspase 9. Active caspase 9 then triggers caspase cascade by activating effector caspases, leading to apoptosis.

FIG. 14C shows experimental results of apoptosis induced by illumination of mitochondrial miniSOG in mammalian cells. In detail, the upper-left panel shows the bright-field image of HEK293 cells. The lower-left panel shows fluorescent nucleus of all cells stained by Hoechst. The upper-right panel indicates mito-AtminiSOG0.2 transfected cells as shown by the IFP infrared fluorescence since the cells were co-transfected with IFP. The lower-right panel shows strong green fluorescence of transfected cells after incubation with green fluorescent dye which only binds to active caspases, indicating high caspase activity after light illumination. Those untransfected cells which are identified in the bright-field and also by the Hoechst staining but don't fluoresce infrared, are not green fluorescent, indicating no caspase activity. These results demonstrate that mitochondria-targeted miniSOG triggers cell apoptosis upon photoexcitation by activating caspases. Genetically-targeted cell photoablation can be used to study cell lineages in intact organisms with high spatiotemporal resolution. Current well-established methods for such application are laser ablation and physical surgery. Both methods are labor-intensive and time-consuming, with poor reproducibility. Newer methods like using toxic genes for genetically-targeted cell ablation suffer from unintended cell killing due to minimal leakiness of gene expression, with poor spatiotemporal resolution.

Example 6

Figure 6:
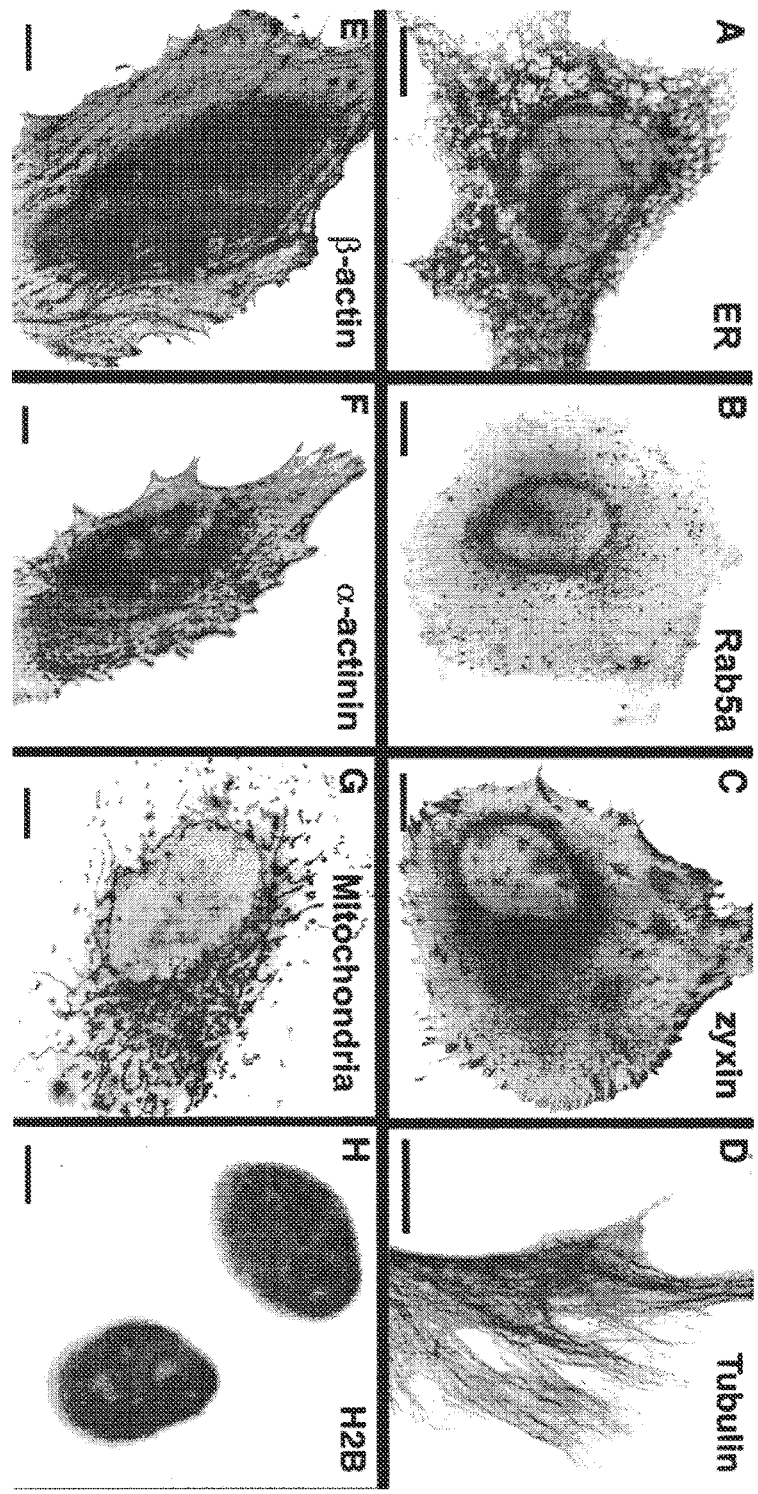
FIG. 6. Confocal fluorescence images of AtminiSOG0.2-targeted endoplasmic reticulum (A), Rab5a (B), zyxin (C), tubulin (D), β-actin (E), α-actinin (F), mitochondria (G), and histone 2B (H) in HeLa cells; scale bars, 10 um. For ease of printing, contrast has been inverted, i.e. dark regions correspond to bright fluorescence.

Correct Localization of Well-Understood Proteins Tagged with MiniSOG in Tissue Culture Cells We used the fluorescence from miniSOG fusion proteins to successfully localize a wide variety of proteins and organelles in cultured mammalian cells (FIG. 6). Its green fluorescence, while modest compared to GFP (quantum yield of 0.37 versus 0.6), revealed that labeled components appeared to have correct localizations (FIG. 6A-H).

FIG. 6A shows ER-targeted AtminiSOG0.2, indicating that miniSOG can work within the secretory pathway. FIG. 6B-F show Rab5a, zyxin, tubulin, β-actin, and α-actinin as examples of proteins tagged in cytosolic compartments. Mitochondrial targeting and nuclear histone 2B-fusions (FIGS. 6G,H) show that miniSOG expresses within those organelles. Using the fluorescence and photo-generated $^1O_2$ from miniSOG for fluorescence photooxidation of DAB (FIG. 7A), correlated confocal and EM imaging could be performed with several miniSOG fusion proteins (FIG. 7B-E), producing excellent EM contrast, efficient labeling, and good preservation of ultrastructure.

Fluorescence imaging, photooxidation, and EM preparation of transfected cultured cells were performed as follows. Transfected cells cultured on glass bottom culture dishes (P35G-0-14-C, MatTek Corp., Ashland, Mass.) were fixed with 2% glutaraldehyde (Electron Microscopy Sciences, Hatfield, Pa.) in pH 7.4 0.1 M sodium cacodylate buffer (Ted Pella Inc., Redding, Calif.) for 30-60 min, rinsed several times in chilled buffer, and treated for 30 min in blocking buffer (50 mM glycine, 10 mM KCN, and 5 mM aminotriazole) to reduce nonspecific background reaction of diaminobenzidine (DAB). Confocal images were taken with minimum exposure using a BioRad MRC-1024 inverted confocal microscope or similar inverted fluorescence microscope to identify transfected cells and for correlative light microscopic imaging.

Detailed protocols for performing fluorescence photooxidation of DAB have been published [2], [6]. It is important to use an inverted microscope to ensure direct open access to the DAB solution. An objective of numerical aperture≥0.7 is desirable to maximize illumination intensity. For photooxidation, diaminobenzidine tetrahydrochloride (Sigma-Aldrich, St. Louis, Mo.) was freshly diluted to 1 mg/ml in 0.1 M sodium cacodylate buffer, pH 7.4, filtered through a 0.22 micron syringe filter (Millipore), and placed on ice and added to the cells.

The region of interest was identified by the fluorescence and an image recorded with care not to bleach the area. A small tube attached to an oxygen tank was placed near the top of the dish and a stream of pure oxygen was gently blown continuously over the top of the solution. Alternately, the DAB solution on ice was bubbled with oxygen and the solution in the dish refreshed every few minutes. The samples were then illuminated using a standard FITC filter set (EX470/40, DM510, BA520) with intense light from a 150W xenon lamp. Illumination was stopped as soon as a very light brown reaction product began to appear in place of the green fluorescence as monitored by transmitted light (typically 2-10 min, depending on the initial fluorescence intensity, the brightness of the illumination, and the optics used). Care was taken to avoid overreacting the samples, as this can lead to overstaining and the degradation of ultrastructure in the region of photooxidation. Multiple areas on a single dish could be reacted if the solution was refreshed every few minutes.

The cells were then removed from the microscope and washed in chilled buffer (5×2 min) and post-fixed in 1% osmium tetroxide (Electron Microscopy Sciences) in 0.1 M sodium cacodylate buffer for 30 min on ice. Cells were washed in chilled buffer twice and rinsed in distilled water, then en bloc stained with 2% aqueous uranyl acetate (Ted Pella Inc.) for 1 h to overnight at 4° C. The samples were then dehydrated in a cold graded ethanol series (20%, 50%, 70%, 90%, 100%, 100%) 2 min each, rinsed once in room temperature anhydrous ethanol, and infiltrated in Durcupan ACM resin (Electron Microscopy Sciences) using 1:1 anhydrous ethanol and resin for 30 min, then 100% resin 2×1 h, then into fresh resin and polymerized in a vacuum oven at 60° C. for 48 h.

α-Actinin cross-links actin bundles and attaches actin filaments to focal adhesions (FA) [26]. EM images of stained miniSOG fusion proteins expressed in HeLa cells contained fibrous densities consistent with published observations associating α-actinin with actin bundles in the cell cortex adjacent to the plasma membrane FA-like structures (FIGS. 7B-E, 8C-D). The higher contrast between cells expressing AtminiSOG0.2 tagged α-actinin versus non-expressing cells is clearly evident in the cytosol in these electron micrographs (FIG. 8A).

Figure 7:
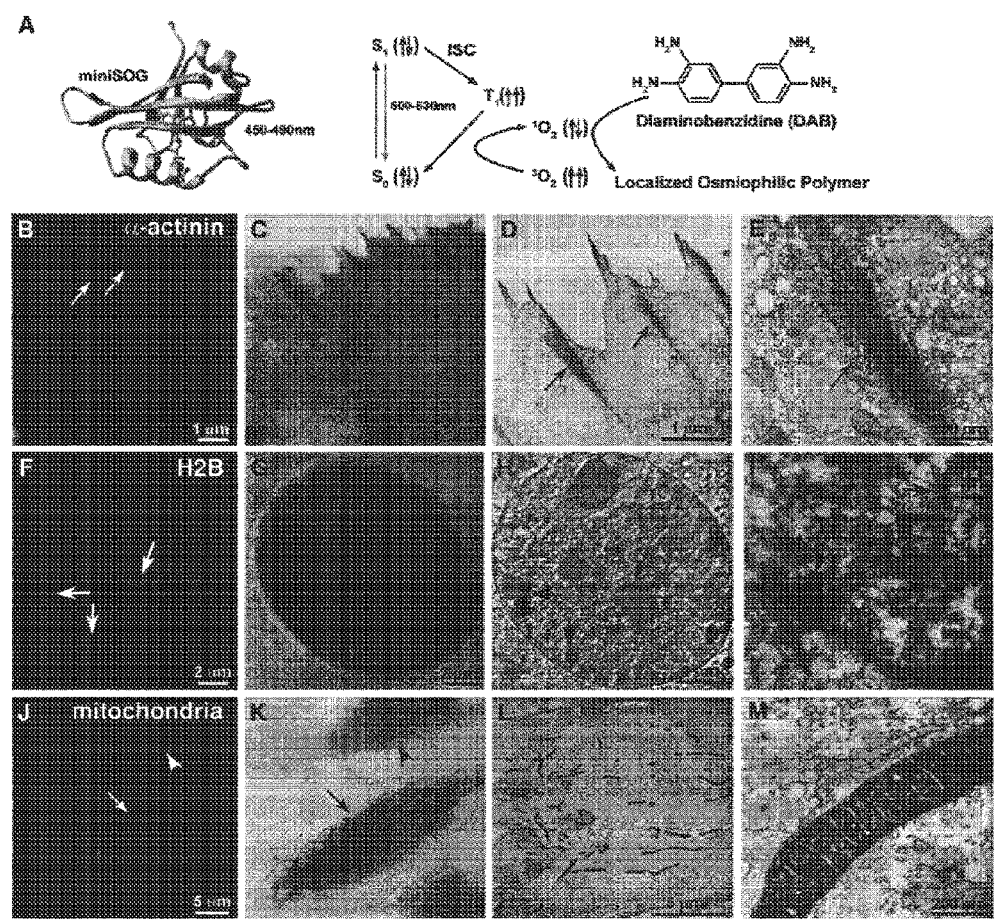
FIG. 7. (A) Schematic diagram of how miniSOG produces EM contrast upon blue-light illumination. Spin states are depicted by the arrows. ISC, intersystem crossing. Correlated confocal fluorescence (B,F,J), transmitted light (C,G,K), and electron microscopic (D,E,H,I,L,M) imaging of a variety of proteins. (B-E) HeLa cells expressing AtminiSOG0.2 labeled α-actinin. Arrows denote correlated structures. (F-I) Histone 2B. Panel H is a 3 nm thick computed slice from an electron tomogram. Panel I is a high magnification thin section electron micrograph showing labeled chromatin fibers near the nuclear envelope (arrows) and a nuclear pore (arrowhead). (J-M) Mitochondrial targeted miniSOG. Panels J and K show a confocal image prior to photooxidation and a transmitted light image following photooxidation, respectively. The differential contrast generated between a transfected (arrows) and non-transfected cell (arrowheads) is evident. Bars B-D, 1 micron; E, 200 nm; F-H, 2 microns; I,100 nm; J-L, 5 microns; M, 200 nm.
Figure 8A:
FIG. 8. AtminiSOG0.2 produces EM contrast in labeled organelles and proteins in cells. (A) Adjacent HeLa cells showing differential contrast between photooxidized cells expressing AtminiSOG0.2 tagged alpha-actinin (arrows) versus a non-expressing cell (arrowheads). (B) Adjacent HeLa cells showing differential contrast between a photooxidized cell expressing miniSOG-targeted mitochondria (arrows) versus a non-expressing cell (arrowheads). (C, D) Low and high magnification showing alpha-actinin tagged with AtminiSOG0.2. Bars, 500 nm.

AtminiSOG0.2-tagged H2B revealed large-scale organizations of chromatin fibers in the perinucleolar and intranuclear regions [27] as imaged by confocal fluorescence, transmitted light after photooxidation, and correlated thin section and electron tomography (arrows, FIG. 7F-H). The tomographic slice demonstrates the utility of miniSOG labeling for 3-dimensional EM analysis. Fibrillar chromatin structures near the nuclear envelope and nuclear pores were also observable at high resolution (arrows and arrowhead, respectively; FIG.

7I). The H2B fusion seemed to have no deleterious effects when incorporated into chromosomes since H2B-AtminiSOG0.2 expressing cells can be found in several stages of mitosis.

Figure 8B:
Figure 8C:
Figure 8D:
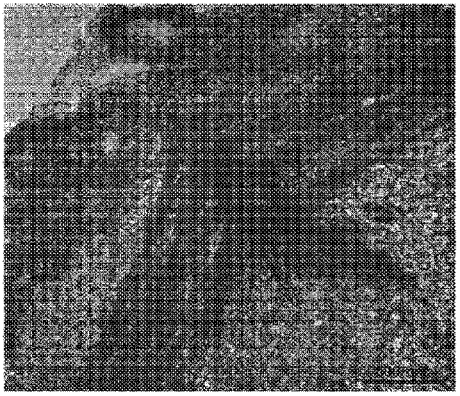

Mitochondria containing cytochrome C-targeted AtminiSOG0.2 fusions had well-preserved morphology of outer and inner membranes and cristae with a strong EM signal present in the mitochondrial matrix consistent with the targeting (FIGS. 7L and M). The contrast differential between mitochondria in cells expressing targeted miniSOG and photooxidized compared to adjacent cells not expressing miniSOG is apparent by both LM (FIGS. 7J and K) and EM (FIG. 8B).

Figure 9:
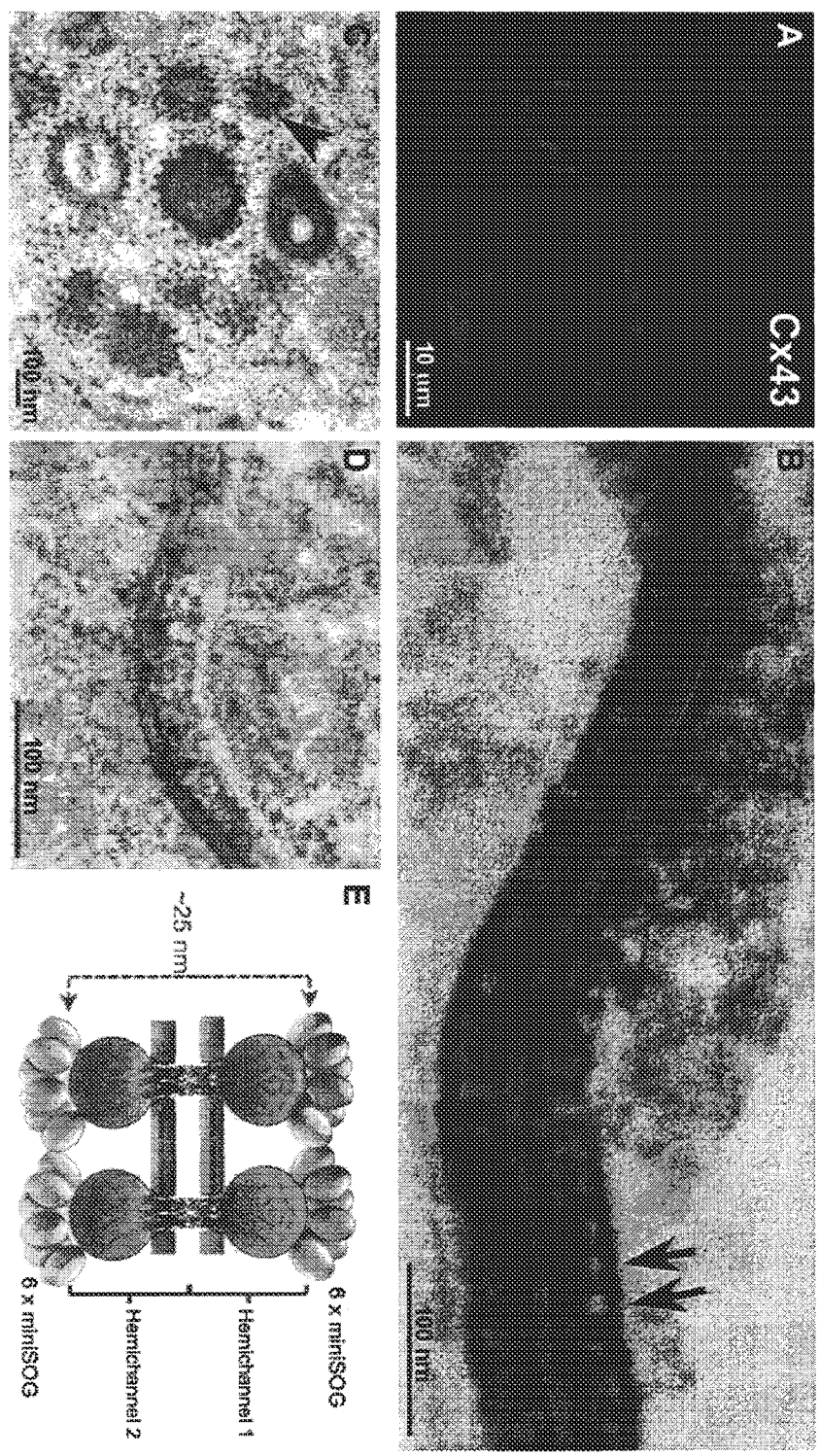
FIG. 9. (A) The green fluorescence of miniSOG reveals gap junctions and transporting vesicles. (B) Electron microscopy indicates negatively stained structures of appropriate size and spacing to be gap junction channels (arrows). (C) Studs on the membranes of trafficking vesicles suggest single connexons. The arrowhead points to two dots with a center-to-center distance ~14 nm (D) A high-quality immunogold image showing a randomly labeled fraction of densely packed Cx43 gap junctions. This figure is reproduced from FIG. 4D of Gaietta et al. [9]. (E) A cartoon showing miniSOG-labeled Cx43 gap junctions. Bar A, 10 microns; B-D, 100 nm.

Cx43 forms gap junction channels. EM of the Cx43-AtminiSOG0.2 fusion showed densely stained DAB photooxidation reaction product outlining structures (FIG. 9B) roughly corresponding in size to gap junction channels each composed of 12 connexins (six in each hemichannel). A cartoon (FIG. 9E) based on the x-ray crystal structure of the transmembrane and extracellular domains of Cx26, which shares 46% sequence identity with that of Cx43 [28], and the NMR structure of the carboxy-terminal domain of Cx43 [29] is shown for interpretation of the EM. Furthermore, we speculate that the black dots studded on the outside of trafficking vesicles (black dots, FIG. 9C) may represent single connexons [30]-[32]. As a comparison, EM of densely packed Cx43 gap junctions using immunogold showed much sparser, more random labeling (FIG. 9D).

Example 7

Localization of MiniSOG in Tissues of Multicellular Organisms

We expressed AtminiSOG0.2 in the matrix of body wall muscle mitochondria using a cytochrome c targeting sequence in *C. elegans* to explore the usefulness of miniSOG for correlated fluorescence and EM in multicellular organisms. In transgenic worms the green fluorescence of miniSOG showed labeled mitochondria in body wall muscle cells (FIG. 10A) while EM revealed a subset of stained mitochondria with well-preserved morphology (FIGS. 10B and C).

Transgenic worms were made by injection of cDNAs of mitochondrially targeted AtminiSOG0.2 driven by myo-3 promoter at 50 ng/μl. The worms were chemically fixed with 2% glutaraldehyde, washed, and blocked as described above. The cuticle was sharply cut to allow diffusion of DAB into the inner body for photooxidation. After confocal imaging and fluorescence photooxidation, the worms were processed for EM imaging as described above.

To ascertain if miniSOG could reveal new molecular details of the organization of neuronal synapses, we expressed AtminiSOG0.2 attached to two isoforms of SynCAM to determine their locations in synapses of mouse neurons. SynCAMs are cell-adhesion molecules involved in synapse formation, maturation, and plasticity whose extensive expression throughout the brain suggests important functions [33]. SynCAMs play an important role in establishing and stabilizing synapses through $Ca^{2+}$-independent interactions, in contrast to $Ca^{2+}$-dependent neurexin-neuroligin interactions [34]. In spite of their recognized role in synapse assembly, the specific localization of SynCAMs had not been accomplished previously. A prior EM study suggested both pre- and post-synaptic membrane localization of SynCAM1 using antibodies raised against its C-terminus, but ambiguity remained because these antibodies cross-react with SynCAM2 and SynCAM3 [33], [34]. To overcome this limitation, we separately examined the synaptic distribution of SynCAM1 and SynCAM2 fusions to AtminiSOG0.2, initially in cultured cortical neurons. SynCAM1-miniSOG was found only at presynaptic terminals, identified by the presence of synaptic vesicles, confirming a presynaptic localization (FIG. 10D). This presynaptic targeting of SynCAM1-miniSOG was also observed in transfected single neurons forming synapses onto themselves in a micro-island culture system [35], ruling out the possibility that postsynaptic neurons are more difficult to identify or transfect. In contrast, SynCAM2 localized to postsynaptic sites in cultured cortical neurons, identified by postsynaptic densities and by the opposition of these terminals to presynaptic boutons bearing synaptic vesicles (FIG. 10E).

Next, we introduced these fusion proteins into prenatal mouse brains by in utero electroporation in order to study their localizations. Endotoxin-free DNA (~3 μg) of the SynCAM2-AtminiSOG0.2 fusion construct was delivered into the lateral ventricle of embryos by in utero electroporation [50]. The offspring at p7 or p21 were anesthetized and fixed by vascular perfusion as previously described [51] with Ringer's solution followed by 4% formaldehyde made fresh from paraformaldehyde (Electron Microscopy Sciences) in 0.15 M cacodylate buffer. Brains were removed and placed in the same fixative at 4° C. for 1 h for p21 and overnight for p7. In this case we avoided glutaraldehyde in combination with paraformaldehyde due to the increased autofluorescence that occurs with glutaraldehyde. The autofluorescence obscured miniSOG fluorescence and made it impossible to locate transfected neurons in the brain slices for photooxidation. Brains were then sliced to 100 μm sections using a vibratome (Leica). Areas of interest were identified by confocal microscopy. The sections were then postfixed with 2% glutaraldehyde for 30 min, rinsed in cold buffer, blocked, and then photooxidized as described above. Subsequent procedures for EM processing were similar to those described above except the vibratome sections were resin embedded between two liquid release agent coated glass slides (Electron Microscopy Sciences).

Because neurons expressing miniSOG fusion proteins may be sparse, we turned to serial block-face scanning electron microscopy (SBFSEM), a relatively new method that facilitates large-scale 3-D reconstruction of tissue to help systematically find synapses from the few transfected neurons within the brains of young adults. The instrument consists of an ultramicrotome fitted within a backscatter-detector equipped scanning electron microscope. In an automated process, the ultramicrotome removes an ultra-thin section of tissue with an oscillating diamond knife and the region of interest is imaged. This sequence is repeated hundreds or thousands of times until the desired volume of tissue is traversed. This method potentially enables the reconstruction of microns to tenths of millimeters of volumes of tissue at a level of resolution better than that obtainable by light microscopy [36], [37]. However, optimal backscatter signal is dependent on very strong scattering from heavy metal stains. The photooxidation of AtminiSOG0.2 generated a strongly osmiophilic reaction product that in combination with en bloc uranyl acetate staining provided a specific and strong backscatter electron signal, which confirmed that the fusion to SynCAM2 was postsynaptic in intact mouse brain (FIGS. 10F and G). Thus, the combination of miniSOG fusion proteins and SBF-SEM provides a method to correlate the location of specific molecules throughout large 3-D volumes and with good preservation of ultrastructure.

Example 8

Gene Synthesis, Mutagenesis, Screening, and Chimera Construction

A gene encoding LOV2 domain of Phototropin 2 with codons optimized for E. coif was synthesized by overlap extension PCR [48]. Genetic libraries were constructed by saturation and random mutagenesis and DNA shuffling [21]. Mutants were fused to IFP1.4 by overlap extension PCR and cloned into a modified pBAD vector containing the heme oxygenase-1 gene from cyanobacteria [21]. Libraries were expressed in *E. coli* strain TOP10 and screened by imaging the agar plates with colonies in the IFP channel before and after blue light illumination [21]. Protein purification and spectroscopic characterization experiments were done as described [49].

DNA encoding miniSOG with codons optimized for mammals was synthesized by overlap extension PCR [48]. MiniSOG fusions were cloned into pcDNA3.1 vector. HEK293 and HeLa cells were transfected with miniSOG or chimera cDNAs using Fugene, then imaged 24-48 h later. Cultured cortical neurons were transfected by Amaxa electroporation (Lonza AG, Germany) and imaged 1-2 wk later.

Example 9

Electron Microscopy

Photooxidized areas of embedded cultured cells were identified by transmitted light and the areas of interest were sawed out using a jeweler's saw and mounted on dummy acrylic blocks with cyanoacrylic adhesive. The coverslip was carefully removed, ultrathin sections were cut using an ultramicrotome, and electron micrographs recorded using a 1200 TEM (JEOL) operating at 80 keV. For tissue sections, one of the glass coverslips was removed using a razorblade and the area of interest identified by transmitted light microscopy. The tissue was removed from the slide, mounted, sectioned, and imaged as above. For electron tomography, 0.5 micron thick sections of cells expressing photooxidized H2B-miniSOG were cut and imaged using a 4000 IVEM (JEOL) operated at 400 keV. Images were tilted and recorded every 2° from +60° to −60°. The image stack was aligned and reconstructions were obtained using R-weighed back projection methods with the IMOD tomography package. For serial block face scanning electron microscopy, a 3View system (Gatan Inc., Pleasanton, Calif.) mounted in a Quanta FEG scanning electron microscope (FEI Company, Eindhoven, The Netherlands) was employed. Imaging was performed as previously described [37]. Individual image planes were hand segmented to outline the plasma membrane of the target neuron and denote labeled post-synaptic densities, then thresholded and projected using Amira (Visage Imaging, Germany).

References

1. Deerinck T. J, Martone M. E, Lev-Ram V, Green D. P, Tsien R. Y, et al. (1994) Fluorescence photooxidation with eosin: a method for high resolution immunolocalization and in situ hybridization detection for light and electron microscopy. J Cell Biol 126: 901-910.
2. Tsien R. Y (2009) Constructing and exploiting the fluorescent protein paintbox (Nobel Lecture). Angew Chem Int Ed Eng 148: 5612-5626.
3. Mercogliano C. P, DeRosier D. J (2007) Concatenated metallothionein as a clonable gold label for electron microscopy. J Struct Biol 160(1): 70-82.
4. Nishino Y, Yasunaga T, Miyazawa A (2007) A genetically encoded metallothionein tag enabling efficient protein detection by electron microscopy. J Electron Microsc (Tokyo) 56(3): 93-101.
5. Diestra E, Fontana J, Guichard P, Marco S, Risco C (2009) Visualization of proteins in intact cells with a clonable tag for electron microscopy. J Struct Biol 165(3): 157-168.
6. Hopkins C, Gibson A, Stinchcombe J, Futter C (2000) Chimeric molecules employing horseradish peroxidase as reporter enzyme for protein localization in the electron microscope. Applications of Chimeric Genes and Hybrid Proteins Pt B 327: 35-45.
7. De Mey J, Moeremans M, Geuens G, Nuydens R, De Brabander M (1981) High resolution light and electron microscopic localization of tubulin with the IGS (immuno gold staining) method. Cell Biol Int Rep 5: 889-899.
8. Porter K. R, Stearns M. E (1981) Stereomicroscopy of whole cells. Methods Cell Biol 22: 53-75.
9. Gaietta G, Deerinck T. J, Adams S. R, Bouwer J, Tour 0, et al. (2002) Multicolor and electron microscopic imaging of connexin trafficking. Science 296: 503-507.
10. Hoffmann C, Gaietta G, Zürn A, Adams S. R, Terrillon S, et al. (2010) Fluorescent labeling of tetracysteine-tagged proteins in intact cells. Nat Protoc 5(10): 1666-1677.
11. Grabenbauer M, Geerts W. J, Femadez-Rodriguez J, Hoenger A, Koster A. J, Nilsson T (2005) Correlative microscopy and electron tomography of GFP through photooxidation. Nat Methods 2(11): 857-862.
12. Meisslitzer-Ruppitsch C, Röhrl C, Neumüller J, Pavelka M, Ellinger A (2009) Photooxidation technology for correlated light and electron microscopy. J Microsc 235(3): 322-335.
13. Jimenez-Banzo A, Nonell S, Hofkens J, Flors C (2008) Singlet oxygen photosensitization by EGFP and its chromophore HBDI, Biophys J 94: 168-172.
14. Bulina M. E, Chudakov D. M, Britanova O. V, Yanushevich Y. G, Staroverov D. B, et al. (2006) A genetically encoded photosensitizer. Nat Biotechnol 24(1): 95-99.
15. Pletnev S, Gurskaya N. G, Pletneva N. V, Lukyanov K. A, Chudakov D. M, et al. (2009) Structural basis for phototoxicity of the genetically encoded photosensitizer killerred. Journal of Biological Chemistry 284: 32028-32039.
16. Jarillo J. A, Gabrys H, Capel J, Alonso J. M, Ecker J. R, et al. (2001) Phototropin-related NPL1 controls chloroplast relocation induced by blue light. Nature 410: 952-954.
17. Kagawa T, Sakai T, Suetsugu N, Oikawa K, Ishiguro S, et al. (2001) *Arabidopsis* NPL1: a phototropin homolog controlling the chloroplast high-light avoidance response. Science 291: 2138-2141.
18. Baier J, Maisch T, Maier M, Engel E, Landthaler M, et al. (2006) Singlet oxygen generation by UVA light exposure of endogenous photosensitizers. Biophys J 91: 1452-1459.
19, Massey V (2000) The chemical and biological versatility of riboflavin. Biochem Soc Trans 28: 283-296.
20. Swartz T. E, Corchnoy S. B, Christie J. M, Lewis J. W, Szundi I, et al. (2001) The photocycle of a flavin-binding domain of the blue light photoreceptor phototropin. J Biol Chem 276: 36493-36500.
21. Shu X, Royant A, Lin M. Z, Aguilera T. A, Lev-Ram V, et al. (2009) Mammalian expression of infrared fluorescent proteins engineered from a bacterial phytochrome. Science 324: 804-807.
22. Hoebeke M, Damoiseau X (2002) Determination of the singlet oxygen quantum yield of bacteriochlorin a: a comparative study in phosphate buffer and aqueous dispersion of dimiristoyl-L-alpha-phosphatidylcholine liposomes. Photochem Photobiol Sci 1: 283-287.

23. Lostao A, El Harrous M, Daoudi F, Romero A, Parody-Morreale A, et al. (2000) Dissecting the energetics of the apoflavodoxin-FMN complex. Journal of Biological Chemistry 275: 9518-9526.

24. Crosson S, Rajagopal S, Moffat K (2003) The LOV domain family: photoresponsive signaling modules coupled to diverse output domains. Biochemistry 42: 2-10.

25. Powers H. J (2003) Riboflavin (vitamin B-2) and health. Am J Clin Nutr 77: 1352-1360.

26. Hu K, Ji L, Applegate K. T, Danuser G, Waterman-Storer C. M (2007) Differential transmission of actin motion within focal adhesions. Science 315: 111-115.

27. Sadoni N, Sullivan K. F, Weinzierl P, Stelzer E. H, Zink D (2001) Large-scale chromatin fibers of living cells display a discontinuous functional organization. Chromosoma 110: 39-51.

28. Maeda S, Nakagawa S, Suga M, Yamashita E, Oshima A, et al. (2009) Structure of the connexin 26 gap junction channel at 3.5 A resolution. Nature 458: 597-602.

29. Sorgen P. L, Duffy H. S, Sahoo P, Coombs W, Delmar M, et al. (2004) Structural changes in the carboxyl terminus of the gap junction protein connexin43 indicates signaling between binding domains for c-Src and zonula occludens-1. Journal of Biological Chemistry 279: 54695-54701.

30. Peracchia C (1977) Gap junctions. Structural changes after uncoupling procedures. J Cell Biol 72: 628-641.

31. Caspar D. L, Goodenough D. A, Makowski L, Phillips W. C (1977) Gap junction structures. I. Correlated electron microscopy and x-ray diffraction. J Cell Biol 74: 605-628.

32. Sosinsky G. E, Nicholson B. J (2005) Structural organization of gap junction channels. Biochim Biophys Acta 1711: 99-125.

33. Fogel A. I, Akins M. R, Krupp A. J, Stagi M, Stein V, et al. (2007) SynCAMs organize synapses through heterophilic adhesion. J Neurosci 27: 12516-12530.

34. Biederer T, Sara Y, Mozhayeva M, Atasoy D, Liu X, et al. (2002) SynCAM, a synaptic adhesion molecule that drives synapse assembly. Science 297: 1525-1531.

35. Hama H, Hara C, Yamaguchi K, Miyawaki A (2004) PKC signaling mediates global enhancement of excitatory synaptogenesis in neurons triggered by local contact with astrocytes. Neuron 41: 405-415.

36. Denk W, Horstmann H (2004) Serial block-face scanning electron microscopy to reconstruct three-dimensional tissue nanostructure. PLoS Biol 2(11): e329. doi:10.1371/journal.pbio.0020329.

37. Jurrus E, Hardy M, Tasdizen T, Fletcher P. T, Koshevoy P, et al. (2009) Axon tracking in serial block-face scanning electron microscopy. Med Image Anal 13: 180-188.

38. Hell S. W (2007) Far-field optical nanoscopy. Science 316: 1153-1158.

39. Huang B, Bates M, Zhuang X (2009) Super-resolution fluorescence microscopy. Annu Rev Biochem 78: 993-1016.

40. Lippincott-Schwartz J, Manley S (2009) Putting super-resolution fluorescence microscopy to work. Nat Methods 6: 21-23.

41. Sudhof T. C (2008) Neuroligins and neurexins link synaptic function to cognitive disease. Nature 455: 903-911.

42. Stagi M, Fogel A. I, Biederer T (2010) SynCAM 1 participates in axo-dendritic contact assembly and shapes neuronal growth cones. Proc Natl Acad Sci USA 107: 7568-7573.

43. Linhoff M. W, Lauren J, Cassidy R. M, Dobie F. A, Takahashi H, et al. (2009) An unbiased expression screen for synaptogenic proteins identifies the LRRTM protein family as synaptic organizers. Neuron 61: 734-749.

44. Woo J, Kwon S. K, Choi S, Kim S, Lee J. R, et al. (2009) Trans-synaptic adhesion between NGL-3 and LAR regulates the formation of excitatory synapses. Nat Neurosci 12: 428-437.

45. Sosinsky G. E, Crum J, Jones Y. Z, Lanman J, Smarr B, et al. (2008) The combination of chemical fixation procedures with high pressure freezing and freeze substitution preserves highly labile tissue ultrastructure for electron tomography applications. Journal of Structural Biology 161: 359-371.

46. Tour 0, Meijer R. M, Zacharias D. A, Adams S. R, Tsien R. Y (2003) Genetically targeted chromophore-assisted light inactivation. Nature Biotechnology 21: 1505-1508.

47. Glickman J. F, Wu X, Mercuri R, Illy C, Bowen B. R, et al. (2002) A comparison of ALPHAScreen, TR-FRET, and TRF as assay methods for FXR nuclear receptors. J Biomol Screen 7: 3-10.

48. Stemmer W. P. C, Crameri A, Ha K. D, Brennan T. M, Heyneker H. L (1995) Single-step assembly of a gene and entire plasmid from large numbers of oligodeoxyribonucleotides. Gene 164: 49-53.

49. Shaner N. C, Campbell R. E, Steinbach P. A, Giepmans B. N. G, Palmer A. E, et al. (2004) Improved monomeric red, orange and yellow fluorescent proteins derived from *Discosoma* sp red fluorescent protein. Nature Biotechnology 22: 1567-1572.

50. Walantus W, Castaneda D, Elias L, Kriegstein A (2007) In utero intraventricular injection and electroporation of E15 mouse embryos. J V is Exp 239.

51. Hayat M. A (2000) Principles and techniques of electron microscopy: biological applications. Cambridge University Press, 4th Ed. pp. 63-73.

52. Arnold K, Bordoli L, Kopp J, Schwede T (2006) The SWISS-MODEL workspace: a web-based environment for protein structure homology modelling. Bioinformatics 22: 195-201.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. An isolated polynucleotide encoding a miniSOG polypeptide comprising an amino acid sequence selected from the group consisting of SEQ ID NO:1 and SEQ ID NO:2.

2. The isolated polynucleotide of claim 1, wherein the miniSOG comprises an amino acid sequence of SEQ ID NO:1.

3. The isolated polynucleotide of claim 1, wherein the miniSOG polypeptide consists of 106 amino acids.

4. The isolated polynucleotide of claim 1, wherein the miniSOG polypeptide has a singlet oxygen quantum yield of 0.47±0.05 or more when bound to a flavin mononucleotide.

5. The isolated polynucleotide of claim 1, wherein the polynucleotide encoding the miniSOG polypeptide is codon optimized for expression in *E. coli* or a eukaryotic cell.

6. The isolated polynucleotide of claim 5, wherein the eukaryotic cell is a mammalian cell.

7. The isolated polynucleotide of claim 5, wherein the mammalian cell is a human cell.

8. A vector comprising the polynucleotide sequence of claim 1.

9. A host cell comprising the vector of claim 8.

10. A miniSOG polypeptide encoded by the polynucleotide of claim 1.

11. A kit comprising the polynucleotide of claim 1.

12. A fusion protein comprising a polypeptide encoded by the polynucleotide of claim 1.

13. A method of expressing in a cell a fusion protein, the method comprising the step of: expressing in a cell a fusion protein comprising i) a polypeptide having an amino acid sequence selected from the group consisting of SEQ ID NO:1 and SEQ ID NO:2 and ii) a protein if interest.

14. The isolated polynucleotide of claim 1, wherein the miniSOG comprises an amino acid sequence of SEQ ID NO:2.

* * * * *

SEQUENCE LISTING

```
<160> NUMBER OF SEQ ID NOS: 31

<210> SEQ ID NO 1
<211> LENGTH: 106
<212> TYPE: PRT
<213> ORGANISM: Artificial Sequence
<220> FEATURE:
<223> OTHER INFORMATION: protein tag
```

<400> SEQUENCE: 1

Met Glu Lys Asn Phe Val Ile Ser Asp Pro Arg Leu Pro Asp Asn Pro
1               5                   10                  15

Ile Ile Phe Ala Ser Asp Ser Phe Leu Glu Leu Thr Glu Tyr Ser Arg
            20                  25                  30

Glu Glu Ile Leu Gly Arg Asn Gly Arg Phe Leu Gln Gly Pro Glu Thr
        35                  40                  45

Asp Gln Ala Thr Val Gln Lys Ile Arg Asp Ala Ile Arg Asp Gln Arg
    50                  55                  60

Glu Ile Thr Val Gln Leu Ile Asn Tyr Thr Lys Ser Gly Lys Lys Phe
65                  70                  75                  80

Trp Asn Leu Phe His Leu Gln Pro Met Arg Asp Gln Lys Gly Glu Leu
                85                  90                  95

Gln Tyr Phe Ile Gly Val Gln Leu Asp Gly
            100                 105

<210> SEQ ID NO 2
<211> LENGTH: 106
<212> TYPE: PRT
<213> ORGANISM: Artificial Sequence
<220> FEATURE:
<223> OTHER INFORMATION: protein tag

<400> SEQUENCE: 2

Met Glu Lys Ser Phe Val Ile Thr Asp Pro Arg Leu Pro Asp Asn Pro
1               5                   10                  15

Ile Ile Phe Ala Ser Asp Gly Phe Leu Glu Leu Thr Glu Tyr Ser Arg
            20                  25                  30

Glu Glu Ile Leu Gly Arg Asn Gly Arg Phe Leu Gln Gly Pro Glu Thr
        35                  40                  45

Asp Gln Ala Thr Val Gln Lys Ile Arg Asp Ala Ile Arg Asp Gln Arg
    50                  55                  60

Glu Ile Thr Val Gln Leu Ile Asn Tyr Thr Lys Ser Gly Lys Lys Phe
65                  70                  75                  80

Trp Asn Leu Leu His Leu Gln Pro Met Arg Asp Gln Lys Gly Glu Leu
                85                  90                  95

Gln Tyr Phe Ile Gly Val Gln Leu Asp Gly
            100                 105

<210> SEQ ID NO 3
<211> LENGTH: 318
<212> TYPE: DNA
<213> ORGANISM: Artificial Sequence
<220> FEATURE:
<223> OTHER INFORMATION: nucleotide

<400> SEQUENCE: 3
atggaaaaaa acttcgtgat ttctgacccg cgcctgccgg ataatccgat catcttcgcc      60
tccgatagct tcctggaact gactgaatac agccgtgagg aaattctggg tcgtaatggc     120
cgtttcctgc agggcccgga aaccgatcaa gcaactgttc agaaaattcg tgatgcaatc     180
cgtgatcaac gtgaaatcac cgtgcagctg attaactata ccaaaagcgg caagaaattc     240
tggaacctgt ttcacctgca gccgatgcgc gatcagaaag gtgagctgca gtacttcatc     300
ggcgttcagc tggatggt                                                  318

<210> SEQ ID NO 4

```
<211> LENGTH: 318
<212> TYPE: DNA
<213> ORGANISM: Artificial Sequence
<220> FEATURE:
<223> OTHER INFORMATION: nucleotide

<400> SEQUENCE: 4
atggagaaaa atttcgtgat aagtgatcca cggctgccag acaatcccat catcttcgca      60
tccgattcct tcctggagct gaccgagtat tccagagagg agatcctggg ccgcaatggc     120
cgctttctgc agggaccaga gacagaccag gccacagtgc agaagattcg cgatgccatt     180
agagatcagc gcgagattac cgtgcagctg ataaactaca caaaaagcgg aagaaattc      240 tggaacctct ttcacctcca gcccatgagg gaccagaagg gtgagctcca gtatttcatc     300
ggagtgcagc tggatgga                                                   318

<210> SEQ ID NO 5
<211> LENGTH: 318
<212> TYPE: DNA
<213> ORGANISM: Artificial Sequence
<220> FEATURE:
<223> OTHER INFORMATION: nucleotide

<400> SEQUENCE: 5
atggaaaaaa gcttcgtgat tactgacccg cgcctgccgg ataatccgat catcttcgcc      60
tccgatggct tcctggaact gactgaatac agccgtgagg aaattctggg tcgtaatggc     120
cgtttcctgc agggcccgga aaccgatcaa gcaactgttc agaaaattcg tgatgcaatc     180
cgtgatcaac gtgaaatcac cgtgcagctg attaactata ccaaaagcgg caagaaattc     240
tggaacctgt tgcacctgca gccgatgcgc gatcagaaag gtgagctgca gtacttcatc     300
ggggttcagc tggatggt                                                   318

<210> SEQ ID NO 6
<211> LENGTH: 318
<212> TYPE: DNA
<213> ORGANISM: Artificial Sequence
<220> FEATURE:
<223> OTHER INFORMATION: nucleotide

<400> SEQUENCE: 6
atggagaaaa gttcgtgat aactgatcca cggctgccag acaatcccat catcttcgca       60
tccgatggct tcctggagct gaccgagtat tccagagagg agatcctggg ccgcaatggc     120
cgctttctgc agggaccaga gacagaccag gccacagtgc agaagattcg cgatgccatt     180
agagatcagc gcgagattac cgtgcagctg ataaactaca caaaaagcgg aagaaattc      240 tggaacctcc tgcacctcca gcccatgagg gaccagaagg gtgagctcca gtatttcatc     300
ggagtgcagc tggatgga                                                   318

<210> SEQ ID NO 7
<211> LENGTH: 106
<212> TYPE: PRT
<213> ORGANISM: Artificial Sequence
<220> FEATURE:
<223> OTHER INFORMATION: LOV domain

<400> SEQUENCE: 7

Ile Glu Lys Asn Phe Val Ile Ser Asp Pro Arg Ile Pro Asp Asn Pro
1               5                   10                  15

Ile Ile Phe Ala Ser Asp Ser Phe Leu Glu Leu Thr Glu Tyr Ser Arg
            20                  25                  30
```

```
Glu Glu Ile Leu Gly Arg Asn Cys Arg Phe Leu Gln Gly Pro Glu Thr
            35                  40                  45

Asp Gln Ala Thr Val Gln Lys Ile Arg Asp Ala Ile Arg Asp Gln Arg
 50                  55                  60

Glu Ile Thr Val Gln Leu Ile Asn Tyr Thr Lys Ser Gly Lys Lys Phe
 65                  70                  75                  80

Trp Asn Leu Phe His Leu Gln Pro Met Arg Asp Gln Lys Gly Glu Leu
                 85                  90                  95

Gln Tyr Phe Ile Gly Val Gln Leu Asp Gly
             100                 105

<210> SEQ ID NO 8
<211> LENGTH: 915
<212> TYPE: PRT
<213> ORGANISM: Artificial Sequence
<220> FEATURE:
<223> OTHER INFORMATION: miniSOG polypeptide

<400> SEQUENCE: 8

Met Glu Arg Pro Arg Ala Pro Pro Ser Pro Leu Asn Asp Ala Glu Ser
 1               5                  10                  15

Leu Ser Glu Arg Arg Ser Leu Glu Ile Phe Asn Pro Ser Ser Gly Lys
             20                  25                  30

Glu Thr His Gly Ser Thr Ser Ser Ser Lys Pro Pro Leu Asp Gly
         35                  40                  45

Asn Asn Lys Gly Ser Ser Ser Lys Trp Met Glu Phe Gln Asp Ser Ala
 50                  55                  60

Lys Ile Thr Glu Arg Thr Ala Glu Trp Gly Leu Ser Ala Val Lys Pro
 65                  70                  75                  80

Asp Ser Gly Asp Asp Gly Ile Ser Phe Lys Leu Ser Ser Glu Val Glu
                 85                  90                  95

Arg Ser Lys Asn Met Ser Arg Arg Ser Ser Glu Glu Ser Thr Ser Ser
            100                 105                 110

Glu Ser Gly Ala Phe Pro Arg Val Ser Gln Glu Leu Lys Thr Ala Leu
        115                 120                 125

Ser Thr Leu Gln Gln Thr Phe Val Val Ser Asp Ala Thr Gln Pro His
130                 135                 140

Cys Pro Ile Val Tyr Ala Ser Ser Gly Phe Phe Thr Met Thr Gly Tyr
145                 150                 155                 160

Ser Ser Lys Glu Ile Val Gly Arg Asn Cys Arg Phe Leu Gln Gly Pro
                165                 170                 175

Asp Thr Asp Lys Asn Glu Val Ala Lys Ile Arg Asp Cys Val Lys Asn
            180                 185                 190

Gly Lys Ser Tyr Cys Gly Arg Leu Leu Asn Tyr Lys Lys Asp Gly Thr
        195                 200                 205

Pro Phe Trp Asn Leu Leu Thr Val Thr Pro Ile Lys Asp Asp Gln Gly
    210                 215                 220

Asn Thr Ile Lys Phe Ile Gly Met Gln Val Glu Val Ser Lys Tyr Thr
225                 230                 235                 240

Glu Gly Val Asn Asp Lys Ala Leu Arg Pro Asn Gly Leu Ser Lys Ser
                245                 250                 255

Leu Ile Arg Tyr Asp Ala Arg Gln Lys Glu Lys Ala Leu Asp Ser Ile
            260                 265                 270

Thr Glu Val Val Gln Thr Ile Arg His Arg Lys Ser Gln Val Gln Glu
        275                 280                 285
```

```
Ser Val Ser Asn Asp Thr Met Val Lys Pro Asp Ser Thr Thr Pro
    290                 295                 300
Thr Pro Gly Arg Gln Thr Arg Gln Ser Asp Glu Ala Ser Lys Ser Phe
305                 310                 315                 320
Arg Thr Pro Gly Arg Val Ser Thr Pro Thr Gly Ser Lys Leu Lys Ser
                325                 330                 335
Ser Asn Asn Arg His Glu Asp Leu Leu Arg Met Glu Pro Glu Glu Leu
            340                 345                 350
Met Leu Ser Thr Glu Val Ile Gly Gln Arg Asp Ser Trp Asp Leu Ser
        355                 360                 365
Asp Arg Glu Arg Asp Ile Arg Gln Gly Ile Asp Leu Ala Thr Thr Leu
    370                 375                 380
Glu Arg Ile Glu Lys Asn Phe Val Ile Ser Asp Pro Arg Leu Pro Asp
385                 390                 395                 400
Asn Pro Ile Ile Phe Ala Ser Asp Ser Phe Leu Glu Leu Thr Glu Tyr
                405                 410                 415
Ser Arg Glu Glu Ile Leu Gly Arg Asn Cys Arg Phe Leu Gln Gly Pro
            420                 425                 430
Glu Thr Asp Gln Ala Thr Val Gln Lys Ile Arg Asp Ala Ile Arg Asp
    435                 440                 445
Gln Arg Glu Ile Thr Val Gln Leu Ile Asn Tyr Thr Lys Ser Gly Lys
450                 455                 460
Lys Phe Trp Asn Leu Phe His Leu Gln Pro Met Arg Asp Gln Lys Gly
465                 470                 475                 480
Glu Leu Gln Tyr Phe Ile Gly Val Gln Leu Asp Gly Ser Asp His Val
                485                 490                 495
Glu Pro Leu Gln Asn Arg Leu Ser Glu Arg Thr Glu Met Gln Ser Ser
            500                 505                 510
Lys Leu Val Lys Ala Thr Ala Thr Asn Val Asp Glu Ala Val Arg Glu
    515                 520                 525
Leu Pro Asp Ala Asn Thr Arg Pro Glu Asp Leu Trp Ala Ala His Ser
530                 535                 540
Lys Pro Val Tyr Pro Leu Pro His Asn Lys Glu Ser Thr Ser Trp Lys
545                 550                 555                 560
Ala Ile Lys Lys Ile Gln Ala Ser Gly Glu Thr Val Gly Leu His His
                565                 570                 575
Phe Lys Pro Ile Lys Pro Leu Gly Ser Gly Asp Thr Gly Ser Val His
            580                 585                 590
Leu Val Glu Leu Lys Gly Thr Gly Glu Leu Tyr Ala Met Lys Ala Met
    595                 600                 605
Glu Lys Thr Met Met Leu Asn Arg Asn Lys Ala His Arg Ala Cys Ile
610                 615                 620
Glu Arg Glu Ile Ile Ser Leu Leu Asp His Pro Phe Leu Pro Thr Leu
625                 630                 635                 640
Tyr Ala Ser Phe Gln Thr Ser Thr His Val Cys Leu Ile Thr Asp Phe
                645                 650                 655
Cys Pro Gly Gly Glu Leu Phe Ala Leu Leu Asp Arg Gln Pro Met Lys
            660                 665                 670
Ile Leu Thr Glu Asp Ser Ala Arg Phe Tyr Ala Ala Glu Val Val Ile
    675                 680                 685
Gly Leu Glu Tyr Leu His Cys Leu Gly Ile Val Tyr Arg Asp Leu Lys
690                 695                 700
```

```
Pro Glu Asn Ile Leu Leu Lys Lys Asp Gly His Ile Val Leu Ala Asp
705                 710                 715                 720

Phe Asp Leu Ser Phe Met Thr Thr Cys Thr Pro Gln Leu Ile Ile Pro
            725                 730                 735

Ala Ala Pro Ser Lys Arg Arg Arg Ser Lys Ser Gln Pro Leu Pro Thr
            740                 745                 750

Phe Val Ala Glu Pro Ser Thr Gln Ser Asn Ser Phe Val Gly Thr Glu
            755                 760                 765

Glu Tyr Ile Ala Pro Glu Ile Ile Thr Gly Ala Gly His Thr Ser Ala
        770                 775                 780

Ile Asp Trp Trp Ala Leu Gly Ile Leu Leu Tyr Glu Met Leu Tyr Gly
785                 790                 795                 800

Arg Thr Pro Phe Arg Gly Lys Asn Arg Gln Lys Thr Phe Ala Asn Ile
            805                 810                 815

Leu His Lys Asp Leu Thr Phe Pro Ser Ser Ile Pro Val Ser Leu Val
            820                 825                 830

Gly Arg Gln Leu Ile Asn Thr Leu Leu Asn Arg Asp Pro Ser Ser Arg
            835                 840                 845

Leu Gly Ser Lys Gly Gly Ala Asn Glu Ile Lys Gln His Ala Phe Phe
850                 855                 860

Arg Gly Ile Asn Trp Pro Leu Ile Arg Gly Met Ser Pro Pro Pro Leu
865                 870                 875                 880

Asp Ala Pro Leu Ser Ile Ile Glu Lys Asp Pro Asn Ala Lys Asp Ile
            885                 890                 895

Lys Trp Glu Asp Asp Gly Val Leu Val Asn Ser Thr Asp Leu Asp Ile
            900                 905                 910

Asp Leu Phe
        915

<210> SEQ ID NO 9
<211> LENGTH: 129
<212> TYPE: PRT
<213> ORGANISM: Artificial Sequence
<220> FEATURE:
<223> OTHER INFORMATION: LOV domain

<400> SEQUENCE: 9

Arg Gln Gly Ile Asp Leu Ala Thr Thr Ile Glu Arg Ile Glu Lys Asn
1               5                   10                  15

Phe Val Ile Ser Asp Pro Arg Leu Pro Asp Asn Pro Ile Ile Phe Ala
            20                  25                  30

Ser Asp Ser Phe Leu Glu Leu Thr Glu Tyr Ser Arg Glu Glu Ile Leu
        35                  40                  45

Gly Arg Asn Cys Arg Phe Leu Gln Gly Pro Glu Thr Asp Gln Ala Thr
    50                  55                  60

Val Gln Lys Ile Arg Asp Ala Ile Arg Asp Gln Arg Glu Ile Thr Val
65                  70                  75                  80

Gln Leu Ile Asn Tyr Thr Lys Ser Gly Lys Lys Phe Trp Asn Leu Phe
                85                  90                  95

His Leu Gln Pro Met Arg Asp Gln Lys Gly Glu Leu Gln Tyr Phe Ile
            100                 105                 110

Gly Val Gln Leu Asp Gly Ser Asp His Val Glu Pro Leu Gln Asn Arg
        115                 120                 125

Leu
```

```
<210> SEQ ID NO 10
<211> LENGTH: 129
<212> TYPE: PRT
<213> ORGANISM: Artificial Sequence
<220> FEATURE:
<223> OTHER INFORMATION: LOV domain

<400> SEQUENCE: 10
```

Arg Gln Gly Ile Asp Leu Ala Thr Thr Leu Glu Arg Ile Glu Lys Asn
1               5                   10                  15

Phe Val Ile Ser Asp Pro Arg Leu Pro Leu Asn Pro Ile Ile Phe Ala
            20                  25                  30

Ser Asp Ser Phe Leu Glu Leu Thr Glu Tyr Thr Arg Glu Glu Ile Leu
        35                  40                  45

Gly Arg Asn Cys Arg Phe Leu Gln Gly Pro Glu Thr Asp Gln Ala Thr
    50                  55                  60

Val Ser Arg Ile Arg Asp Ala Ile Arg Glu Gln Arg Glu Ile Thr Val
65                  70                  75                  80

Gln Leu Ile Asn Tyr Thr Lys Ser Gly Lys Lys Phe Trp Asn Leu Phe
                85                  90                  95

His Leu Gln Pro Met Arg Asp Gln Lys Gly Glu Leu Gln Tyr Phe Ile
            100                 105                 110

Gly Val Gln Leu Asp Gly Ser Asp His Val Glu Pro Leu Lys Asn Arg
        115                 120                 125

Leu

```
<210> SEQ ID NO 11
<211> LENGTH: 129
<212> TYPE: PRT
<213> ORGANISM: Artificial Sequence
<220> FEATURE:
<223> OTHER INFORMATION: LOV domain

<400> SEQUENCE: 11
```

Arg Gln Gly Ile Asp Leu Ala Thr Thr Leu Glu Arg Ile Glu Lys Asn
1               5                   10                  15

Phe Val Ile Ser Asp Pro Arg Leu Pro Asp Asn Pro Ile Ile Phe Ala
            20                  25                  30

Ser Asp Ser Phe Leu Glu Leu Thr Glu Tyr Thr Arg Glu Glu Ile Leu
        35                  40                  45

Gly Arg Asn Cys Arg Phe Leu Gln Gly Pro Glu Thr Asp Gln Thr Thr
    50                  55                  60

Val Gln Lys Ile Arg Asp Ala Ile Lys Glu Gln Arg Asp Ile Thr Val
65                  70                  75                  80

Gln Leu Ile Asn Tyr Thr Lys Ser Gly Arg Lys Phe Trp Asn Leu Phe
                85                  90                  95

His Leu Gln Pro Met Arg Asp Gln Lys Gly Glu Leu Gln Tyr Phe Ile
            100                 105                 110

Gly Val Gln Leu Asp Gly Ser Asp His Val Glu Pro Leu Arg Asn Arg
        115                 120                 125

Leu

```
<210> SEQ ID NO 12
<211> LENGTH: 129
<212> TYPE: PRT
<213> ORGANISM: Artificial Sequence
<220> FEATURE:
<223> OTHER INFORMATION: LOV domain
```

<400> SEQUENCE: 12

Arg Gln Gly Ile Asp Leu Ala Thr Thr Leu Glu Arg Ile Glu Lys Asn
1               5                   10                  15

Phe Val Ile Thr Asp Pro Arg Leu Pro Asp Asn Pro Ile Ile Phe Ala
            20                  25                  30

Ser Asp Ser Phe Leu Glu Leu Thr Glu Phe Thr Arg Glu Glu Ile Leu
        35                  40                  45

Gly Arg Asn Cys Arg Phe Leu Gln Gly Pro Glu Thr Phe Gln Ala Thr
    50                  55                  60

Val Gln Lys Ile Arg Asp Ala Ile Lys Glu Gln Lys Glu Ile Thr Val
65                  70                  75                  80

Gln Leu Ile Asn Tyr Thr Lys Ser Gly Lys Lys Phe Trp Asn Leu Phe
                85                  90                  95

His Leu Gln Pro Met Arg Asp Gln Lys Gly Glu Leu Gln Tyr Phe Ile
            100                 105                 110

Gly Val Gln Leu Asp Gly Ser Asp His Val Arg Pro Leu Arg Asn Arg
        115                 120                 125

Leu

<210> SEQ ID NO 13
<211> LENGTH: 129
<212> TYPE: PRT
<213> ORGANISM: Artificial Sequence
<220> FEATURE:
<223> OTHER INFORMATION: LOV domain

<400> SEQUENCE: 13

Arg Gln Gly Ile Asp Leu Ala Thr Thr Leu Glu Arg Ile Glu Lys Asn
1               5                   10                  15

Phe Val Ile Ser Asp Pro Arg Leu Pro Asp Gln Pro Ile Ile Phe Ala
            20                  25                  30

Ser Asp Ser Phe Leu Glu Leu Thr Glu Tyr Thr Arg Glu Glu Ile Leu
        35                  40                  45

Gly Arg Asn Cys Arg Phe Phe Leu Gln Gly Pro Glu Thr Asp Gln Ala
    50                  55                  60

Thr Val Asn Arg Ile Arg Asp Ala Ile Lys Asp Arg Glu Ile Thr Val
65                  70                  75                  80

Gln Leu Ile Asn Tyr Thr Lys Ser Gly Lys Lys Phe Trp Asn Leu Phe
                85                  90                  95

His Ile Gln Pro Met Arg Asp Gln Lys Gly Glu Leu Gln Tyr Phe Ile
            100                 105                 110

Gly Val Gln Leu Asp Gly Ser Asp His Leu Glu Pro Leu Arg Asn Arg
        115                 120                 125

Leu

<210> SEQ ID NO 14
<211> LENGTH: 129
<212> TYPE: PRT
<213> ORGANISM: Artificial Sequence
<220> FEATURE:
<223> OTHER INFORMATION: LOV domain

<400> SEQUENCE: 14

Arg Gln Gly Ile Asp Leu Ala Thr Thr Leu Glu Arg Ile Glu Lys Asn
1               5                   10                  15

Phe Val Ile Thr Asp Pro Arg Leu Pro Asp Asn Pro Ile Ile Phe Ala
            20                  25                  30

Ser Asp Ser Phe Leu Glu Leu Thr Glu Tyr Thr Arg Glu Glu Ile Leu
        35                  40                  45

Gly Arg Asn Cys Arg Phe Leu Gln Gly Pro Glu Thr Asp Met Ser Thr
    50                  55                  60

Val Asp Lys Ile Arg Glu Ala Ile Arg Glu Gln Lys Glu Ile Thr Val
65                  70                  75                  80

Gln Leu Ile Asn Tyr Thr Lys Ser Gly Lys Lys Phe Trp Asn Leu Phe
                85                  90                  95

His Leu Gln Pro Met Arg Asp Gln Lys Gly Leu Gln Tyr Phe Ile
            100                 105                 110

Gly Val Gln Leu Asp Gly Ser Asp His Val Glu Pro Leu Arg Asn Arg
            115                 120                 125

Leu

<210> SEQ ID NO 15
<211> LENGTH: 129
<212> TYPE: PRT
<213> ORGANISM: Artificial Sequence
<220> FEATURE:
<223> OTHER INFORMATION: LOV domain

<400> SEQUENCE: 15

Arg Gln Gly Ile Asp Leu Ala Thr Thr Leu Glu Arg Ile Glu Lys Asn
1               5                   10                  15

Phe Val Ile Thr Asp Pro Arg Ile Pro Asp Asn Pro Ile Ile Phe Ala
            20                  25                  30

Ser Asp Ser Phe Leu Glu Leu Thr Glu Tyr Thr Arg Glu Glu Ile Leu
        35                  40                  45

Gly Arg Asn Cys Arg Phe Leu Gln Gly Pro Glu Thr Asp Gln Gly Thr
    50                  55                  60

Val Asp Lys Ile Arg Glu Ala Ile Arg Glu Gln Lys Glu Ile Thr Val
65                  70                  75                  80

Gln Leu Ile Asn Tyr Thr Lys Ser Gly Lys Lys Phe Trp Asn Leu Phe
                85                  90                  95

His Leu Gln Pro Met Arg Asp Gln Lys Gly Leu Gln Tyr Phe Ile
            100                 105                 110

Gly Val Gln Leu Asp Gly Ser Asp His Val Glu Pro Leu Arg Asn Arg
            115                 120                 125

Leu

<210> SEQ ID NO 16
<211> LENGTH: 129
<212> TYPE: PRT
<213> ORGANISM: Artificial Sequence
<220> FEATURE:
<223> OTHER INFORMATION: LOV domain

<400> SEQUENCE: 16

Arg Lys Gly Ile Asp Leu Ala Thr Thr Leu Glu Arg Ile Glu Lys Asn
1               5                   10                  15

Phe Val Ile Thr Asp Pro Arg Leu Pro Asp Asn Pro Ile Ile Phe Ala
            20                  25                  30

Ser Asp Ser Phe Leu Glu Leu Thr Glu Tyr Ser Arg Glu Glu Ile Leu
        35                  40                  45

Gly Arg Asn Cys Arg Phe Leu Gln Gly Pro Glu Thr Asp Leu Thr Thr
    50                  55                  60

Val Lys Lys Ile Arg Asn Ala Ile Asp Asn Gln Thr Glu Val Thr Val
65                  70                  75                  80

Gln Leu Ile Asn Tyr Thr Lys Ser Gly Lys Lys Phe Trp Asn Ile Phe
                85                  90                  95

His Leu Gln Pro Met Arg Asp Gln Lys Gly Glu Val Gln Tyr Phe Ile
            100                 105                 110

Gly Val Gln Leu Asp Gly Ser Lys His Val Glu Pro Val Arg Asn Val
        115                 120                 125

Ile

<210> SEQ ID NO 17
<211> LENGTH: 123
<212> TYPE: PRT
<213> ORGANISM: Artificial Sequence
<220> FEATURE:
<223> OTHER INFORMATION: LOV domain

<400> SEQUENCE: 17

Arg Arg Gly Ile Asp Leu Ala Thr Thr Leu Glu Arg Ile Glu Lys Asn
1               5                   10                  15

Phe Val Ile Thr Asp Pro Arg Leu Pro Asp Asn Pro Ile Ile Phe Ala
                20                  25                  30

Ser Asp Ser Phe Leu Gln Leu Thr Glu Tyr Ser Arg Glu Glu Ile Leu
            35                  40                  45

Gly Arg Asn Cys Arg Phe Leu Gln Gly Pro Glu Thr Asp Arg Ala Thr
        50                  55                  60

Val Arg Lys Ile Arg Asp Ala Ile Asp Asn Gln Thr Glu Val Thr Val
65                  70                  75                  80

Gln Leu Ile Asn Tyr Thr Lys Ser Gly Lys Lys Phe Trp Asn Leu Phe
                85                  90                  95

His Leu Gln Pro Met Arg Asp Gln Lys Gly Asp Val Gln Tyr Phe Ile
            100                 105                 110

Gly Val Gln Leu Asp Gly Thr Glu His Val Arg
        115                 120

<210> SEQ ID NO 18
<211> LENGTH: 129
<212> TYPE: PRT
<213> ORGANISM: Artificial Sequence
<220> FEATURE:
<223> OTHER INFORMATION: LOV domain

<400> SEQUENCE: 18

Arg Lys Gly Ile Asp Leu Ala Thr Thr Leu Glu Arg Ile Glu Lys Asn
1               5                   10                  15

Phe Val Ile Thr Asp Pro Arg Leu Pro Asp Asn Pro Ile Ile Phe Ala
                20                  25                  30

Ser Asp Ser Phe Leu Glu Leu Thr Glu Tyr Ser Arg Glu Glu Ile Leu
            35                  40                  45

Gly Arg Asn Cys Arg Phe Leu Gln Gly Pro Glu Thr Asp Pro Ala Thr
        50                  55                  60

Val Lys Lys Ile Arg Gln Ala Ile Asp Asn Gln Thr Asp Val Thr Val
65                  70                  75                  80

Gln Leu Ile Asn Tyr Thr Lys Thr Gly Lys Lys Phe Trp Asn Leu Phe
                85                  90                  95

His Leu Gln Pro Met Arg Asp Gln Lys Gly Glu Val Gln Tyr Phe Ile
            100                 105                 110

-continued

Gly Val Gln Leu Asp Gly Ser Gln His Val Glu Pro Leu Gln Asn Ser
            115                 120                 125
Ile

<210> SEQ ID NO 19
<211> LENGTH: 129
<212> TYPE: PRT
<213> ORGANISM: Artificial Sequence
<220> FEATURE:
<223> OTHER INFORMATION: LOV domain

<400> SEQUENCE: 19

Arg Lys Gly Leu Asp Leu Ala Thr Thr Leu Glu Arg Ile Glu Lys Asn
1               5                   10                  15

Phe Val Ile Thr Asp Pro Arg Leu Pro Asp Asn Pro Ile Ile Phe Ala
            20                  25                  30

Ser Asp Ser Phe Leu Glu Leu Thr Glu Tyr Ser Arg Glu Glu Ile Leu
        35                  40                  45

Gly Lys Asn Cys Arg Phe Leu Gln Gly Pro Glu Thr Asp Pro Ala Thr
    50                  55                  60

Val Arg Lys Ile Arg Glu Ala Ile Asp Asn Gln Thr Glu Val Thr Val
65                  70                  75                  80

Gln Leu Ile Asn Tyr Thr Lys Ser Gly Lys Lys Phe Trp Asn Leu Phe
                85                  90                  95

His Leu Gln Pro Met Arg Asp His Lys Gly Glu Val Gln Tyr Phe Ile
            100                 105                 110

Gly Val Gln Leu Asp Gly Ser Gln His Val Glu Pro Leu His Asn Cys
        115                 120                 125

Ile

<210> SEQ ID NO 20
<211> LENGTH: 129
<212> TYPE: PRT
<213> ORGANISM: Artificial Sequence
<220> FEATURE:
<223> OTHER INFORMATION: LOV domain

<400> SEQUENCE: 20

Arg Arg Gly Ile Asp Leu Ala Thr Thr Leu Glu Arg Ile Glu Lys Asn
1               5                   10                  15

Phe Val Ile Thr Asp Pro Arg Leu Pro Asp Asn Pro Ile Ile Phe Ala
            20                  25                  30

Ser Asp Glu Phe Leu Glu Leu Thr Glu Tyr Thr Arg Glu Glu Ile Leu
        35                  40                  45

Gly Arg Asn Cys Arg Phe Leu Gln Gly Pro Asp Thr Asp Gln Asn Thr
    50                  55                  60

Val Gln Lys Ile Arg Asp Ala Ile Lys Glu Asn Arg Asp Ile Thr Val
65                  70                  75                  80

Gln Leu Leu Asn Tyr Thr Lys Ser Gly Lys Pro Phe Trp Asn Leu Phe
                85                  90                  95

His Leu Gln Ala Met Arg Asp His Lys Gly Glu Leu Gln Tyr Phe Ile
            100                 105                 110

Gly Val Gln Met Asp Gly Ser Glu Tyr Val Glu Pro Thr Arg His Arg
        115                 120                 125

Leu

<210> SEQ ID NO 21

<211> LENGTH: 129
<212> TYPE: PRT
<213> ORGANISM: Artificial Sequence
<220> FEATURE:
<223> OTHER INFORMATION: LOV domain

<400> SEQUENCE: 21

Arg Val Ser Gln Glu Leu Lys Thr Ala Leu Ser Thr Leu Gln Gln Thr
1               5                   10                  15
Phe Val Val Ser Asp Ala Thr Gln Pro His Gln Pro Ile Val Tyr Ala
                20                  25                  30
Ser Ser Gly Phe Phe Thr Met Thr Gly Tyr Ser Ser Lys Glu Ile Val
            35                  40                  45
Gly Arg Asn Cys Arg Phe Leu Gln Gly Pro Asp Thr Asp Lys Asn Glu
        50                  55                  60
Val Ala Lys Ile Arg Asp Gln Val Lys Asn Gly Lys Ser Tyr Cys Gly
65                  70                  75                  80
Arg Leu Leu Asn Tyr Lys Lys Asp Gly Thr Pro Phe Trp Asn Leu Leu
                85                  90                  95
Thr Val Thr Pro Ile Lys Asp Asp Gln Gly Asn Thr Ile Lys Phe Ile
                100                 105                 110
Gly Met Gln Val Glu Val Ser Lys Tyr Thr Glu Gly Val Asn Asp Lys
            115                 120                 125
Ala

<210> SEQ ID NO 22
<211> LENGTH: 129
<212> TYPE: PRT
<213> ORGANISM: Artificial Sequence
<220> FEATURE:
<223> OTHER INFORMATION: LOV domain

<400> SEQUENCE: 22

Arg Val Ser Gln Glu Leu Lys Glu Ala Leu Ala Thr Leu Gln Gln Thr
1               5                   10                  15
Phe Val Val Ser Asp Ala Thr Lys Pro Asp Gln Pro Ile Met Tyr Ala
                20                  25                  30
Ser Ser Gly Phe Phe Ser Met Thr Gly Tyr Ser Ser Lys Glu Ile Ile
            35                  40                  45
Gly Arg Asn Cys Arg Phe Leu Gln Gly Pro Asp Thr Asp Lys Asn Glu
        50                  55                  60
Val Asp Lys Ile Arg Asp Ala Ile Arg Asn Gly Arg Ser Tyr Cys Gly
65                  70                  75                  80
Arg Leu Leu Asn Tyr Lys Lys Asn Gly Thr Pro Phe Trp Asn Leu Leu
                85                  90                  95
Thr Val Thr Pro Ile Lys Asp Asp Lys Gly Asn Thr Ile Lys Phe Ile
                100                 105                 110
Gly Met Gln Val Glu Val Ser Lys Tyr Thr Glu Gly Val Asn Glu Lys
            115                 120                 125
Ala

<210> SEQ ID NO 23
<211> LENGTH: 129
<212> TYPE: PRT
<213> ORGANISM: Artificial Sequence
<220> FEATURE:
<223> OTHER INFORMATION: LOV domain

<400> SEQUENCE: 23

```
Arg Val Ser Gln Asp Leu Lys Asp Ala Leu Ala Thr Leu Gln Gln Thr
1               5                   10                  15

Phe Val Val Ser Asp Ala Thr Lys Pro Asp Gln Pro Ile Val Tyr Ala
            20                  25                  30

Ser Ser Gly Phe Phe Thr Met Thr Gly Tyr Ser Ser Lys Glu Ile Val
        35                  40                  45

Gly Arg Asn Cys Arg Phe Leu Gln Gly Lys Asp Thr Asp Gln Asn Glu
    50                  55                  60

Val Ala Lys Ile Arg Asp Ala Val Lys Thr Gly Lys Ser Tyr Cys Gly
65                  70                  75                  80

Arg Leu Leu Asn Tyr Lys Lys Asn Gly Thr Pro Phe Trp Asn Leu Leu
                85                  90                  95

Thr Val Thr Pro Ile Lys Asp Asp Ser Gly Lys Thr Ile Lys Phe Ile
                100                 105                 110

Gly Met Gln Val Glu Val Ser Lys Tyr Thr Glu Gly Val Asn Glu Lys
            115                 120                 125

Glu
```

<210> SEQ ID NO 24
<211> LENGTH: 129
<212> TYPE: PRT
<213> ORGANISM: Artificial Sequence
<220> FEATURE:
<223> OTHER INFORMATION: LOV domain

<400> SEQUENCE: 24

```
Arg Val Ser Gln Glu Leu Lys Asp Ala Leu Ser Thr Leu Gln Gln Thr
1               5                   10                  15

Phe Val Val Ser Asp Ala Thr Lys Pro Asp Gln Pro Ile Leu Tyr Ala
            20                  25                  30

Ser Ser Gly Phe Phe Ser Met Thr Gly Tyr Ser Ser Lys Glu Val Ile
        35                  40                  45

Gly Arg Asn Cys Arg Phe Leu Gln Gly Pro Glu Thr Asp Gln Asn Glu
    50                  55                  60

Val Ala Lys Ile Arg Asp Ala Thr Lys Asn Gly Lys Ser Tyr Cys Gly
65                  70                  75                  80

Arg Leu Leu Asn Tyr Lys Lys Asn Gly Thr Pro Phe Trp Asn Leu Leu
                85                  90                  95

Thr Val Thr Pro Ile Lys Asp Asp Arg Gly Asn Thr Ile Lys Phe Ile
                100                 105                 110

Gly Met Gln Val Glu Val Ser Lys Tyr Thr Glu Gly Val Asn Glu Lys
            115                 120                 125

Ala
```

<210> SEQ ID NO 25
<211> LENGTH: 129
<212> TYPE: PRT
<213> ORGANISM: Artificial Sequence
<220> FEATURE:
<223> OTHER INFORMATION: LOV domain

<400> SEQUENCE: 25

```
Arg Val Ser Gln Glu Leu Lys Asp Ala Leu Ser Ser Leu Gln Gln Thr
1               5                   10                  15

Phe Val Val Ser Asp Ala Thr Arg Pro Asp Gln Pro Ile Ile Tyr Ala
            20                  25                  30
```

Ser Ala Gly Phe Tyr Thr Met Thr Gly Tyr Thr Pro Lys Glu Val Thr
            35                  40                  45

Gly Arg Asn Cys Arg Phe Leu Gln Gly Pro Asp Thr Asp Met Asn Glu
 50                  55                  60

Val Ala Lys Ile Arg Asp Ala Val Lys Thr Gly Arg Ser Phe Cys Gly
 65                  70                  75                  80

Arg Leu Leu Asn Tyr Arg Lys Asp Gly Thr Pro Phe Trp Asn Met Leu
                 85                  90                  95

Thr Val Thr Pro Ile Arg Asp Asp Asn Gly Lys Val Ile Lys Phe Ile
            100                 105                 110

Gly Met Gln Val Glu Val Ser Lys Tyr Thr Glu Gly Leu Ser Glu Lys
        115                 120                 125

Arg

<210> SEQ ID NO 26
<211> LENGTH: 129
<212> TYPE: PRT
<213> ORGANISM: Artificial Sequence
<220> FEATURE:
<223> OTHER INFORMATION: LOV domain

<400> SEQUENCE: 26

Arg Val Ser Gln Glu Leu Lys Asp Ala Leu Ser Ser Leu Gln Gln Thr
 1               5                  10                  15

Phe Val Val Ser Asp Ala Thr Arg Pro Asp Gln Pro Ile Ile Tyr Ala
             20                  25                  30

Ser Glu Gly Phe Phe Thr Met Thr Gly Tyr Ser Pro Arg Glu Val Val
            35                  40                  45

Gly Arg Asn Cys Arg Phe Leu Gln Gly Pro Asp Thr Asp Ala Ala Glu
 50                  55                  60

Val Ala Lys Ile Arg Asp Ala Val Lys His Gly Arg Ser Phe Cys Gly
 65                  70                  75                  80

Arg Leu Leu Asn Tyr Arg Lys Asp Gly Ala Pro Phe Trp Asn Leu Leu
                 85                  90                  95

Thr Val Thr Pro Ile Arg Asp Asp Asn Gly Lys Val Ile Lys Phe Ile
            100                 105                 110

Gly Met Gln Val Glu Val Ser Lys Tyr Thr Glu Gly Leu Ser Asp Lys
        115                 120                 125

Arg

<210> SEQ ID NO 27
<211> LENGTH: 129
<212> TYPE: PRT
<213> ORGANISM: Artificial Sequence
<220> FEATURE:
<223> OTHER INFORMATION: LOV domain

<400> SEQUENCE: 27

Arg Val Ser Glu Asp Leu Lys Asp Ala Leu Ser Thr Phe Gln Gln Thr
 1               5                  10                  15

Phe Val Val Ser Asp Ala Thr Lys Pro Asp Tyr Pro Ile Met Tyr Ala
             20                  25                  30

Ser Ala Gly Phe Phe Asn Met Thr Gly Tyr Thr Ser Lys Glu Val Val
            35                  40                  45

Gly Arg Asn Cys Arg Phe Leu Gln Gly Ser Gly Thr Asp Ala Asp Glu
 50                  55                  60

Leu Ala Lys Ile Arg Glu Thr Leu Ala Ala Gly Asn Asn Tyr Cys Gly

```
                65                  70                  75                  80
Arg Ile Leu Asn Tyr Lys Lys Asp Gly Thr Ser Phe Trp Asn Leu Leu
                85                  90                  95

Thr Ile Ala Pro Ile Lys Asp Glu Ser Gly Lys Val Leu Lys Phe Ile
            100                 105                 110

Gly Met Gln Val Glu Val Ser Lys His Thr Glu Gly Ala Lys Glu Lys
            115                 120                 125

Ala
```

<210> SEQ ID NO 28
<211> LENGTH: 129
<212> TYPE: PRT
<213> ORGANISM: Artificial Sequence
<220> FEATURE:
<223> OTHER INFORMATION: LOV domain

<400> SEQUENCE: 28

```
Arg Val Ser Glu Glu Leu Arg Ala Ala Leu Ser Ala Phe Gln Gln Thr
 1                5                  10                 15

Phe Val Val Ser Asp Ala Ser Arg Pro Gly His Pro Ile Met Tyr Ala
                20                  25                  30

Ser Ala Gly Phe Phe Asn Met Thr Gly Tyr Thr Ser Lys Glu Val Val
            35                  40                  45

Gly Arg Asn Cys Arg Phe Leu Gln Gly Ser Gly Thr Asp Pro Ala Glu
        50                  55                  60

Ile Ala Lys Ile Arg Gln Ala Leu Ala Asn Gly Ser Asn Tyr Cys Gly
65                  70                  75                  80

Arg Val Leu Asn Tyr Lys Lys Asp Gly Thr Ala Phe Trp Asn Leu Leu
                85                  90                  95

Thr Ile Ala Pro Ile Lys Asp Glu Glu Gly Arg Val Leu Lys Phe Ile
            100                 105                 110

Gly Met Gln Val Glu Val Ser Lys Tyr Thr Glu Gly Asn Lys Asp Thr
            115                 120                 125

Val
```

<210> SEQ ID NO 29
<211> LENGTH: 129
<212> TYPE: PRT
<213> ORGANISM: Artificial Sequence
<220> FEATURE:
<223> OTHER INFORMATION: LOV domain

<400> SEQUENCE: 29

```
Arg Val Ser Glu Asp Leu Arg Asp Ala Leu Ser Thr Phe Gln Gln Thr
 1                5                  10                 15

Phe Val Val Ser Asp Ala Thr Lys Pro Asp Tyr Pro Ile Leu Tyr Ala
                20                  25                  30

Ser Ala Gly Phe Phe Lys Met Thr Gly Tyr Thr Ser Lys Glu Val Ile
            35                  40                  45

Gly Arg Asn Cys Arg Phe Met Gln Gly Ser Gly Thr Asp Pro Glu Asp
        50                  55                  60

Val Ala Thr Ile Arg Glu Ala Leu Gln Ser Gly Ser Tyr Cys Gly
65                  70                  75                  80

Arg Leu Leu Asn Tyr Lys Lys Asp Gly Thr Pro Phe Trp Asn Leu Leu
                85                  90                  95

Thr Ile Ala Pro Ile Lys Asp Asp Ala Gly Lys Val Leu Lys Phe Ile
            100                 105                 110
```

-continued

Gly Met Gln Val Glu Val Ser Lys His Thr Glu Gly Ser Lys Glu Lys
        115                 120                 125
Thr

<210> SEQ ID NO 30
<211> LENGTH: 129
<212> TYPE: PRT
<213> ORGANISM: Artificial Sequence
<220> FEATURE:
<223> OTHER INFORMATION: LOV domain

<400> SEQUENCE: 30

Arg Val Ser Glu Asp Leu Lys Asp Ala Leu Ser Ala Phe Gln Gln Thr
1               5                   10                  15

Phe Val Val Ser Asp Ala Thr Lys Pro Asp Tyr Pro Ile Leu Tyr Ala
            20                  25                  30

Ser Ala Gly Phe Phe Lys Met Thr Gly Tyr Thr Ser Lys Glu Val Ile
        35                  40                  45

Gly Arg Asn Cys Arg Phe Leu Gln Gly Ala Asp Thr Asp Pro Asp Asp
    50                  55                  60

Val Ala Arg Ile Arg Glu Ala Leu Glu Gly Gly Lys Ser Phe Cys Gly
65                  70                  75                  80

Arg Leu Leu Asn Tyr Lys Lys Asp Gly Thr Pro Phe Trp Asn Leu Leu
                85                  90                  95

Thr Ile Ser Pro Ile Lys Asp Asp Gly Asn Val Leu Lys Leu Ile
            100                 105                 110

Gly Met Leu Val Glu Val Asn Lys His Thr Glu Gly Ser Lys Glu Lys
        115                 120                 125
Lys

<210> SEQ ID NO 31
<211> LENGTH: 129
<212> TYPE: PRT
<213> ORGANISM: Artificial Sequence
<220> FEATURE:
<223> OTHER INFORMATION: LOV domain

<400> SEQUENCE: 31

Gln Val Ser Glu Glu Leu Leu Asp Ala Leu Ser Ser Phe Lys Gln Thr
1               5                   10                  15

Phe Val Val Ser Asp Ala Thr Lys Pro Asp Gln Pro Ile Val Tyr Ala
            20                  25                  30

Ser Ala Gly Phe Phe Thr Met Ser Gly Tyr Ser Ala Lys Glu Ile Ile
        35                  40                  45

Gly His Asn Cys Arg Phe Leu Gln Gly Pro Asp Thr Asp Pro Ala Asp
    50                  55                  60

Val Glu Lys Ile Arg His Ala Val Lys Asn Gly Lys Asn Phe Cys Gly
65                  70                  75                  80

Arg Leu Leu Asn Tyr Arg Lys Asp Gly Ser Thr Phe Trp Asn Leu Leu
                85                  90                  95

Thr Ile Thr Pro Ile Lys Asp Glu Asn Asp Lys Val Val Lys Phe Ile
            100                 105                 110

Gly Met Gln Val Glu Val Ser Lys Tyr Thr Glu Gly Ala Lys Ala Val
        115                 120                 125
Ala